United States Patent
Yang et al.

(10) Patent No.: US 12,134,630 B2
(45) Date of Patent: Nov. 5, 2024

(54) COMPOSITIONS AND METHODS FOR LIQUID PHASE OLIGONUCLEOTIDE SYNTHESIS

(71) Applicant: Hongene Biotech Corporation, Union City, CA (US)

(72) Inventors: Gaomai Yang, Davis, CA (US); Jingshe Song, Union City, CA (US); Shengdong Wang, Fremont, CA (US); Yun-Chiao Yao, Union City, CA (US); Hongrong Yang, Union City, CA (US); David Yu, Union City, CA (US); Aldrich N.K. Lau, Palo Alto, CA (US)

(73) Assignee: Hongene Biotech Corporation, Union City, CA (US)

( * ) Notice: Subject to any disclaimer, the term of this patent is extended or adjusted under 35 U.S.C. 154(b) by 48 days.

(21) Appl. No.: 18/337,233

(22) Filed: Jun. 19, 2023

(65) Prior Publication Data
US 2024/0002420 A1    Jan. 4, 2024

Related U.S. Application Data

(60) Provisional application No. 63/354,150, filed on Jun. 21, 2022, provisional application No. 63/382,691, filed on Nov. 7, 2022.

(51) Int. Cl.
| | | |
|---|---|---|
| *C07H 1/00* | (2006.01) | |
| *C08F 120/68* | (2006.01) | |
| *C08F 220/28* | (2006.01) | |
| *C08F 220/56* | (2006.01) | |
| *C08F 265/10* | (2006.01) | |

(52) U.S. Cl.
CPC ............ *C07H 1/00* (2013.01); *C08F 120/68* (2013.01); *C08F 220/286* (2020.02); *C08F 220/56* (2013.01); *C08F 265/10* (2013.01)

(58) Field of Classification Search
CPC ...... C07H 1/00; C08F 120/68; C08F 220/286; C08F 220/65; C08F 265/10
See application file for complete search history.

(56) References Cited

U.S. PATENT DOCUMENTS

| 5,798,210 A | 8/1998 | Canard et al. |
|---|---|---|
| 6,677,120 B2 | 1/2004 | Shanghvi et al. |
| 7,276,599 B2 | 10/2007 | Moore et al. |
| 8,143,369 B2 | 3/2012 | Fujiwara et al. |
| 8,450,504 B2 | 5/2013 | Hedrick et al. |
| 8,664,357 B2 | 3/2014 | Livingston |
| 10,544,456 B2 | 1/2020 | Esfandyarpour et al. |
| 11,725,073 B2 | 8/2023 | Lau et al. |
| 2002/0120096 A1 | 8/2002 | Tsuchida et al. |
| 2002/0123609 A1 | 9/2002 | Frechet et al. |
| 2013/0225789 A1 | 8/2013 | Sun et al. |
| 2013/0231260 A1 | 9/2013 | Lau et al. |
| 2014/0287945 A1 | 9/2014 | Lau et al. |
| 2015/0056139 A1* | 2/2015 | Luo .................... A61K 49/0054 424/9.1 |
| 2015/0306034 A1* | 10/2015 | Gao ..................... A61K 9/1075 514/315 |
| 2018/0023122 A1 | 1/2018 | Crameri et al. |
| 2018/0100190 A1 | 4/2018 | Esfandyarpour et al. |
| 2023/0212209 A1 | 7/2023 | Yang et al. |

FOREIGN PATENT DOCUMENTS

| EP | 0 850 949 | 7/1998 |
|---|---|---|
| EP | 1 710 249 | 1/2005 |
| FR | 2623510 | 5/1989 |
| WO | WO 02/079215 | 10/2002 |
| WO | WO 03/093346 | 11/2003 |
| WO | WO 05/123139 | 12/2005 |
| WO | WO 16/160475 | 10/2016 |

OTHER PUBLICATIONS

Bonora et al., 1990, HELP (high efficiency liquid phase) new oligonucleotide synthesis on soluble polymeric support, Nucleic Acids Research, 18(11)3155-3159.
Feng et al., 2001, Synthesis and characterization of new block copolymers with poly(ethylene oxide) and poly[3(S)-sec butylmorphoine-2,5-dione] sequences, Macromol. Biosci., 1:30-39.
Zhang et al., 2015, Tuning multiple arms for camptothecin and folate conjugations on star-shaped copolymers to enhance glutathione-mediated intracellular drug delivery, Polymer Chemistry, 6:2192-2203.
International Search Report and Written Opinion dated Sep. 25, 2023 in international application No. PCT/US2023/025655.
Atdbio, 2021, Solid State Oligonucleotide Synthesis, https://www.atdbio.com/content/17/Solid-phase-oligonucleotide-synthesis, 26 pp.
Beaucage et al., 1992, Advances in the synthesis of oligonucleotides by the phosphoramidite approach, Tetrahedron, 48(12):2223-2311.
Bonora et al., 1993, Large scale, liquid phase synthesis of oligonucleotides by the phosphoramidite approach, Nucleic Acids Research, 21(5):1213-1217.
Carey, 1992, Organic Chemistry, 2d ed., McGraw-Hill, Inc., New York, pp. 328-331.
Creusen et al., 2020, Scalable one-pot-liquid-phase oligonucleotide synthesis for model network hydrogels, ChemRxiv., preprint. https://doi.org/10.26434/chemrxiv.12327569.v1.
Gorelov et al., 1979, Thermal decomposition of poly(phenyl- and poly(pentafluorophenyl acrylates)), Vysokomolekularnye Soedineniya, Seriya B: Bratkie Soobshcheniya, 21(6):410-413 (abstract).

(Continued)

*Primary Examiner* — Robert D Harlan
(74) *Attorney, Agent, or Firm* — Knobbe, Martens, Olson & Bear, LLP

(57) ABSTRACT

Embodiments of the present application relate to polymers used as polymeric polyvalent hubs for liquid phase oligonucleotide synthesis. Methods for making an oligonucleotide by liquid phase oligonucleotide synthesis using the polymers are also provided.

38 Claims, 10 Drawing Sheets

(56) References Cited

OTHER PUBLICATIONS

Gravert et al., 1997, Organic synthesis on soluble polymer supports: liquid-phase methodologies, Chem. Rev., 97:489-509.

Greene et al., 1999, Protective Groups in Organic Synthesis, 3rd Ed., John Wiley & Sons, New York (TOC).

Katayama et al., 2018, Liquid-phase synthesis of oligonucleotides, in Synthesis of Therapeutic Oligonucleotides, Obika et al., eds., Springer Nature Singapore Pte Ltd., pp. 83-95.

Kim et al., 2013, Liquid-phase RNA synthesis by using alkyl-chain-soluble support, Chem. Eur. J., 19:8615-8620.

Livingston, Jan. 2, 2020, Liquid phase oligonucleotide synthesis, Oxford Global, Biologics Series, 2 pp.

McMurry, 2000, Organic Chemistry, 5th ed., Brooks/Cole, Pacific Grove, CA, pp. 398 and 408.

McOmie, ed., 1973, Protective Groups in Organic Chemistry, Plenum Press (TOC).

Merrifield, Jul. 20, 1963, Solid phase peptide synthesis. I. The synthesis of a tetrapeptide, J. Am. Chem. Soc., 85(14):2149-2154.

Merrifield, Oct. 8, 1965, Automated synthesis of peptides: solid-phase peptide synthesis, a simple and rapid synthetic method, has now been automates, Science, 150(3693):178-185.

Molina et al., 2019, Liquid-phase oligonucleotide synthesis: past, present, and future predictions, Current Protocols in Nucleic Acid Chemistry, 77:e82, 17 pp.

Scheit, 1980, Nucleotide analogs: Synthesis and biological function. New York: John Wiley & Sons (TOC).

Streitwieser et al., 1981, Introduction to Organic Chemistry, 2d ed., Macmillan Publishing Co., Inc., New York, pp. 169-171.

Takahashi et al., 2012, Development of an efficient liquid-phase peptide synthesis protocol using a novel fluorene-derived anchor support compound with Fmoc chemistry; AJIPHASE®, Tetrahedron Lett., 53:1936-1939.

Takahashi et al., 2012, Novel diphenylmethyl-derived amide protecting group for efficient liquid-phase peptide synthesis: AJIPHASE, Organic Lett., 14:4514-4517.

Takahashi et al., 2017, AJIPHASER®: a highly efficient synthetic method for one-pot peptide elongation in the solution phase by an Fmoc strategy, Angew. Chem. Int. Ed., 56:7803-7807.

Uhlman et al., Jun. 1990, Antisense oligonucleotides: a new therapeutic principle, Chemical Reviews, 90(4):543-584.

Wang et al., 2016, Recent advances in regenerated cellulose materials, Progress in Polymer Science, 53:169-206.

\* cited by examiner

COMPOSITIONS AND METHODS FOR LIQUID PHASE OLIGONUCLEOTIDE SYNTHESIS

BACKGROUND

The present disclosure relates to methods and compositions for liquid phase oligonucleotide synthesis employing the use of a polymer having pendant poly(ethylene glycol) arms.

DESCRIPTION OF THE RELATED ART

Oligonucleotide-based drugs have become a powerful epitome having ability to treat various diseases. Currently, the demand for oligonucleotides can be fulfilled by conventional solid phase oligonucleotide synthesis (SPOS). There are certain advantages of SPOS, such as simple product isolation and the use of anhydrous synthetic environment. However, the SPOS generally has low overall yield after multiple steps for an oligo sequence and high cost for reagents, solid support and waste management. In addition, SPOS may result in mismatched oligo sequences which leads to difficulty in purification. The increasing demand for metric ton quantities of oligonucleotides far exceeds the production capacity of solid phase oligonucleotide synthesis.

Liquid phase oligonucleotide synthesis (LPOS) is a technology with the potential to provide the production capacity that will be required. One of the major advantages of LPOS over SPOS is the absence of the heterogeneous nature of the process, i.e., insoluble solid supports are not present. The use of a soluble scaffold or support employed in LPOS allows each step of the synthesis to be performed in the liquid phase with improved kinetics.

Polyethylene glycol (PEG) is one of the most widely used soluble polymer supports which has received considerable attention. *Current Protocol in Nucleic Acid Chemistry* (2019) 77, e82. First, the cost of the PEG process is low. Second, PEG platform is great beneficial for large-scale production due to its high coupling efficiency and possibilities of using a convergent synthesis. Therefore, further exploration on PEG based platform shows great prospects for LPOS development.

SUMMARY

Some aspects of the present disclosure relate to a polymer for liquid phase oligonucleotide synthesis having the structure of Formula (I):

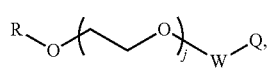

wherein:

R is H, or unsubstituted or substituted $C_1$-$C_6$ alkyl;

W is $C_1$-$C_{20}$ alkylene, a 2 to 20 membered heteroalkylene, or a bond;

Q is

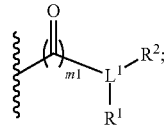

$L^1$ is $C_1$-$C_{20}$ alkylene, 2 to 20 membered heteroalkylene, optionally substituted phenylene, optionally substituted 5 to 6 membered heteroarylene, optionally substituted 3 to 10 membered heterocyclylene, or optionally substituted $C_3$-$C_{10}$ cycloalkylene, or $C_1$-$C_{20}$ alkylene or 2 to 20 membered heteroalkylene in which one or more methylene repeating units is each independently replaced by a group selected from the group consisting of optionally substituted phenylene, optionally substituted 5 to 6 membered heteroarylene, optionally substituted 3 to 10 membered heterocyclylene, optionally substituted $C_3$-$C_{10}$ cycloalkylene, —C(=O)—, —CH=CH—, and —C≡C—;

each of $R^1$ and $R^2$ is independently —$OR^3$ or —$NR^{4a}R^{4b}$;

$R^3$ is H, $C_1$-$C_6$ alkyl, a hydroxy protecting group, or

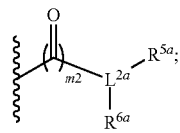

each of $R^{4a}$ and $R^{4b}$ is H, optionally substituted $C_1$-$C_6$ alkyl, —C(=O)($C_1$-$C_6$ alkyl), —C(=O)phenyl, an amino protecting group, or

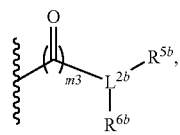

or $R^{4a}$ and $R^{4b}$ taken together is a divalent amino protecting group;

each of $L^{2a}$ and $L^{2b}$ is independently $C_1$-$C_{20}$ alkylene, 2 to 20 membered heteroalkylene, optionally substituted phenylene, optionally substituted 5 to 6 membered heteroarylene, optionally substituted 3 to 10 membered heterocyclylene, or optionally substituted $C_3$-$C_{10}$ cycloalkylene, or $C_1$-$C_{20}$ alkylene or 2 to 20 membered heteroalkylene in which one or more methylene repeating units is each independently replaced by a group selected from the group consisting of optionally substituted phenylene, optionally substituted 5 to 6 membered heteroarylene, optionally substituted 3 to 10 membered heterocyclylene, optionally substituted $C_3$-$C_{10}$ cycloalkylene, —C(=O)—, —CH=CH—, and —C≡C—;

each of $R^{5a}$, $R^{5b}$, $R^{6a}$ and $R^{6b}$ is independently H, —$OR^7$ or —$NR^{8a}R^{8b}$;

each of $R^7$ is independently H, $C_1$-$C_6$ alkyl, a hydroxy protecting group, or

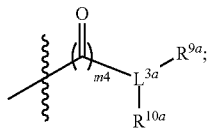

each of $R^{8a}$ and $R^{8b}$ is independently H, optionally substituted $C_1$-$C_6$ alkyl, —C(=O)($C_1$-$C_6$ alkyl), —C(=O)phenyl, an amino protecting group, or

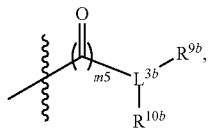

or $R^{8a}$ and $R^{8b}$ taken together is a divalent amino protecting group;

each of $L^{3a}$ and $L^{3b}$ is independently $C_1$-$C_{20}$ alkylene, 2 to 20 membered heteroalkylene, optionally substituted phenylene, optionally substituted 5 to 6 membered heteroarylene, optionally substituted 3 to 10 membered heterocyclylene, or optionally substituted $C_3$-$C_{10}$ cycloalkylene, or $C_1$-$C_{20}$ alkylene or 2 to 20 membered heteroalkylene in which one or more methylene repeating units is each independently replaced by a group selected from the group consisting of optionally substituted phenylene, optionally substituted 5 to 6 membered heteroarylene, optionally substituted 3 to 10 membered heterocyclylene, optionally substituted $C_3$-$C_{10}$ cycloalkylene, —C(=O)—, —CH=CH—, and —C≡C—;

each of $R^{9a}$, $R^{9b}$, $R^{10a}$ and $R^{10b}$ is independently H, —$OR^{11}$ or —$NR^{12a}R^{12b}$;

each of $R^{11}$ is independently H, $C_1$-$C_6$ alkyl, a hydroxy protecting group, or

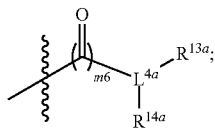

each of $R^{12a}$ and $R^{12b}$ is independently H, optionally substituted $C_1$-$C_6$ alkyl, —C(=O)($C_1$-$C_6$ alkyl), —C(=O)phenyl, an amino protecting group, or

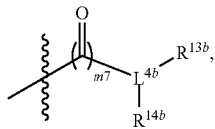

or $R^{12a}$ and $R^{12b}$ taken together is a divalent amino protecting group;

each of $L^{4a}$ and $L^{4b}$ is independently $C_1$-$C_{20}$ alkylene, 2 to 20 membered heteroalkylene, optionally substituted phenylene, optionally substituted 5 to 6 membered heteroarylene, optionally substituted 3 to 10 membered heterocyclylene, or optionally substituted $C_3$-$C_{10}$ cycloalkylene, or $C_1$-$C_{20}$ alkylene or 2 to 20 membered heteroalkylene in which one or more methylene repeating units is each independently replaced by a group selected from the group consisting of optionally substituted phenylene, optionally substituted 5 to 6 membered heteroarylene, optionally substituted 3 to 10 membered heterocyclylene, optionally substituted $C_3$-$C_{10}$ cycloalkylene, —C(=O)—, —CH=CH—, and —C≡C—;

each of $R^{13a}$, $R^{13b}$, $R^{14a}$ and $R^{14b}$ is independently H, —OH, protected hydroxy, —NH (optionally substituted $C_1$-$C_6$ alkyl), —$NH_2$, or protected amino;

each of m1, m2, m3, m4, m5, m6 and m7 is independently 0 or 1; and j is an integer from 15 to 1500.

In some embodiments of the polymer of Formula (I), R is —$CH_3$. In some other embodiment, R is H. In some embodiments, W is —$CH_2CH_2NH$—. In other embodiments, W is —$CH_2CH_2O$—. In some embodiments, W is $C_2$-$C_6$ alkylene, such as —$CH_2CH_2$—. In another embodiment, W is a bond.

In some embodiments of the polymer of Formula (I), $L^1$ is $C_2$-$C_6$ alkylene. In other embodiments $L^1$ is a 3 to 12 or 3 to 6 membered heteroalkylene containing one, two or three heteroatoms selected from N, O or S. In further embodiment, the heteroalkylene contains one or two nitrogen atoms.

In some embodiments of the polymer of Formula (I), $R^1$ is —OH or a protected hydroxy. In other embodiments, $R^1$ is —$NH_2$, —NH (optionally substituted $C_1$-$C_6$ alkyl), —NHC(=O)$CH_3$ (—NHAc), or a protected amino. In still other embodiments, $R^1$ is

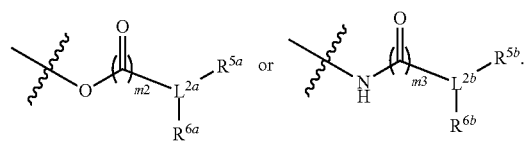

In some embodiments of the polymer of Formula (I), $R^2$ is —OH or a protected hydroxy. In other embodiments, $R^2$ is —$NH_2$, —NH (optionally substituted $C_1$-$C_6$ alkyl), —NHC(=O)$CH_3$, or a protected amino. In still other embodiments, $R^2$ is

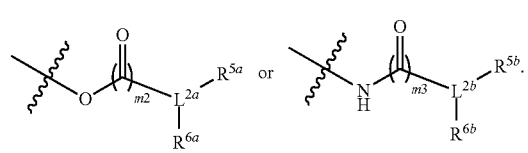

In some embodiments, each of $L^{2a}$ and $L^{2b}$ is independently a $C_2$-$C_6$ alkylene. In other embodiments, each of $L^{2a}$ and $L^{2b}$ is independently an optionally substituted phenylene. In some embodiments, each of $R^{5a}$, $R^{5b}$, $R^{6a}$ and $R^{6b}$ is independently H, —OH, a protected hydroxy, —$NH_2$, —NH (optionally substituted $C_1$-$C_6$ alkyl), —NHC(=O)$CH_3$, or a protected amino. In some further embodiments, each of m2 and m3 is 1. In other embodiments, m2 is 0 and m3 is 1. In other embodiments, m2 is 1 and m3 is 0. In other embodiments, both m2 and m3 are 0.

In some embodiments of the polymer of Formula (I), Q is selected from the group consisting of

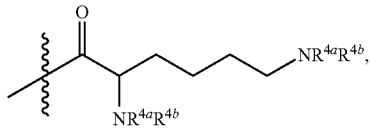

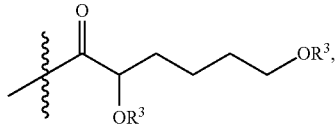

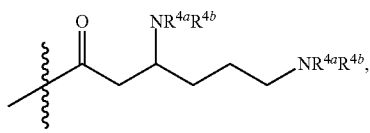

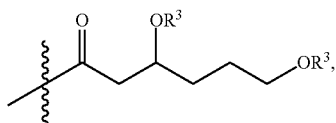

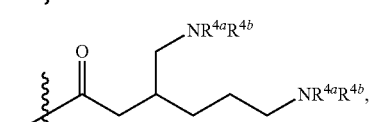

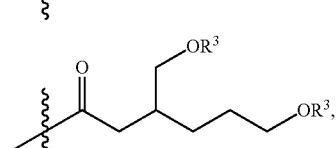

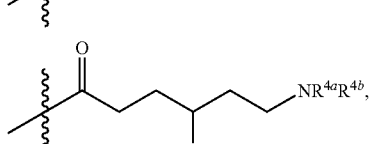

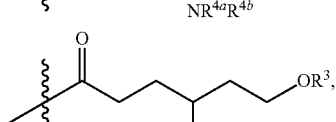

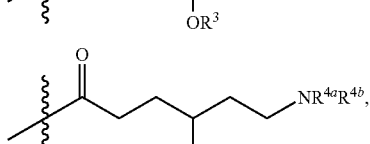

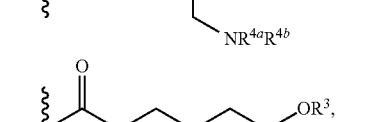

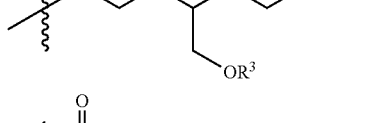

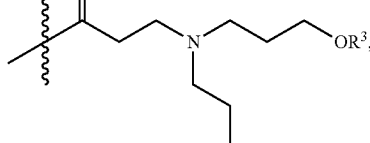, and

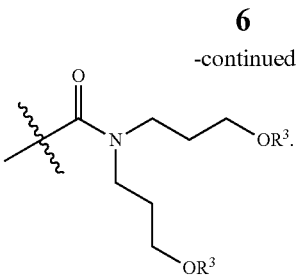

In some embodiments of the polymer of Formula (I), each $R^3$ is independently H or a hydroxy protecting group, each $R^{4a}$ and $R^{4b}$ is independently H, optionally substituted $C_1$-$C_6$ alkyl, —C(=O)CH$_3$, or an amino protecting group. In some other embodiments, each $R^{4a}$ is H, each $R^{4b}$ is independently H, —C(=O)(C$_1$-C$_6$ alkyl), —C(=O)phenyl, an amino protecting group, or

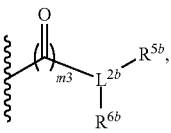

or the hydrogen in —NHR$^{4b}$ is absent, and R$^{4b}$ is a divalent amino protecting group. In some such embodiments, R$^3$ is

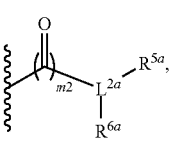

$R^{4a}$ is H, and $R^{4b}$ is

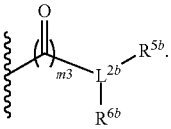

In still other embodiments, $R^3$ is H, $R^{4a}$ is H, and $R^{4b}$ is

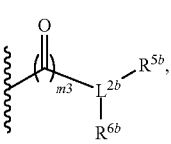

or $R^{4a}$ and $R^{4b}$ are each H, and $R^3$ is

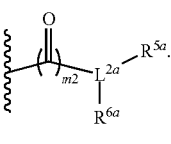

In some further embodiments, each of m2 and m3 is 1. In other embodiments, m2 is 0 and m3 is 1. In other embodiments, m2 is 1 and m3 is 0. In other embodiments, both m2 and m3 are 0.

In some further embodiments of the polymer of Formula (I) or (I'), Q is selected from the group consisting of:

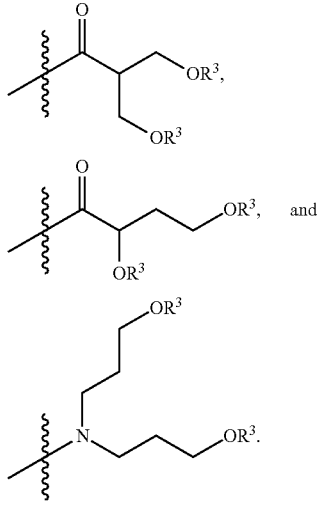

In some such embodiments, each $R^3$ is independently H or a hydroxy protecting group. In some other embodiments, each $R^3$ is

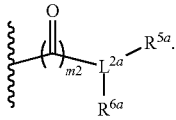

In still other embodiments, one of $R^3$ is H and the other $R^3$ is

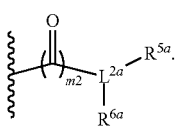

In some further embodiments, m2 is 1. In other embodiments, m2 is 0.

In some embodiments of the polymer of Formula (I) or any substructure described herein, each of $L^{2a}$ and $L^{2b}$ is independently $C_1$-$C_{10}$ alkylene or 2 to 10 membered heteroalkylene; each of $R^{5a}$, $R^{5b}$, $R^{6a}$ and $R^{6b}$ are independently H, —$OR^7$ or —$NR^{8a}R^{8b}$; each of $R^7$ is independently H, $C_1$-$C_6$ alkyl, a hydroxy protecting group, or

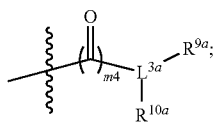

and each of $R^{8a}$ and $R^{8b}$ is independently H, optionally substituted $C_1$-$C_6$ alkyl, —C(=O)($C_1$-$C_6$ alkyl), —C(=O)phenyl, an amino protecting group, or

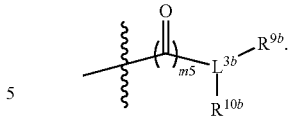

In some embodiments, $L^{2a}$ is a $C_2$-$C_6$ alkylene linker. In other embodiments, $L^{2a}$ is a 3 to 12 or 3 to 6 membered heteroalkylene linker containing one, two or three heteroatoms selected from O, S or N. In further embodiment, the heteroalkylene contains one or two nitrogen atoms. In some embodiments, $L^{2b}$ is a $C_2$-$C_6$ alkylene linker. In other embodiments, $L^{2b}$ is a 2 to 6 membered heteroalkylene linker containing one, two or three heteroatoms selected from O, S or N. In further embodiment, the heteroalkylene contains one or two nitrogen atoms. In other embodiments, each of $L^{2a}$ and $L^{2b}$ is independently optionally substituted phenylene; or $C_2$-$C_6$ alkylene or 3 to 12 membered heteroalkylene, wherein one methylene unit is replaced by an optionally substituted phenylene. In some embodiments, each $R^{8a}$ is H, and each of $R^{5a}$, $R^{5b}$, $R^{6a}$ and $R^{6b}$ is independently H, —$OR^7$ or —$NHR^{8b}$, each $R^{8b}$ is independently H, —C(=O)($C_1$-$C_6$ alkyl), —C(=O)phenyl, an amino protecting group, or

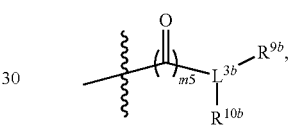

or the hydrogen in —$NHR^{8b}$ is absent, and $R^{8b}$ is a divalent amino protecting group. In some embodiments, each of $R^{5a}$, $R^{5b}$, $R^{6a}$ and $R^{6b}$ is independently H, —OH, a protected hydroxy, —$NH_2$, —NH (optionally substituted $C_1$-$C_6$ alkyl), —NHC(=O)$CH_3$, or a protected amino. In some further embodiments, each of $R^{5a}$, $R^{5b}$, $R^{6a}$ and $R^{6b}$ is independently —$OR^7$ or —$NR^{8a}R^{8b}$; and wherein at least one of $R^7$ is

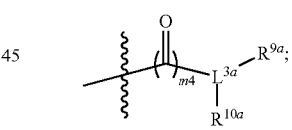

and at least one of $R^{8a}$ and $R^{8b}$ is

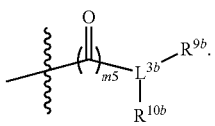

In some other embodiments, each of $R^7$ is independently

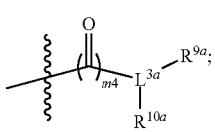

and each of $R^{8a}$ and $R^{8b}$ is independently

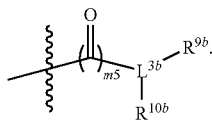

In some specific embodiments, $R^{8a}$ is H, $R^{8b}$ is H or an amino protecting group (e.g., Ac), and each of $R^{5a}$, $R^{5b}$, $R^{6a}$ and $R^{6b}$ is independently —NH$_2$, —NH (optionally substituted C$_1$-C$_6$ alkyl), or —NHC(=O)CH$_3$. In other embodiments, at least one of $R^{5a}$, $R^{5b}$, $R^{6a}$ and $R^{6b}$ is H. In other embodiments, $R^7$ is H, and each of $R^{5a}$, $R^{5b}$, $R^{6a}$ and $R^{6b}$ is —OH. In other embodiments, $R^7$ is

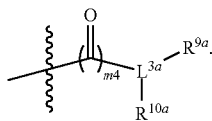

In other embodiments, $R^{8a}$ is H and $R^{8b}$ is

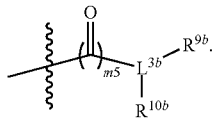

In some further embodiments, each of m4 and m5 is 1. In other embodiments, m4 is 0 and m5 is 1. In other embodiments, m4 is 1 and m5 is 0. In other embodiments, both m4 and m5 are 0. In some further embodiments, each of $L^{3a}$ and $L^{3b}$ is independently C$_1$-C$_{10}$ alkylene or 2 to 10 membered heteroalkylene; each of $R^{9a}$, $R^{9b}$, $R^{10a}$ and $R^{10b}$ are independently H, —OR$^{11}$ or —NR$^{12a}$R$^{12b}$; each of $R^{11}$ is independently H, C$_1$-C$_6$ alkyl, a hydroxy protecting group, or

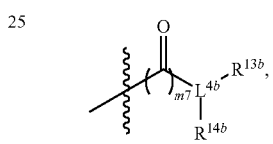

and each of $R^{12a}$ and $R^{12b}$ is independently H, optionally substituted C$_1$-C$_6$ alkyl, —C(=O)(C$_1$-C$_6$ alkyl), —C(=O) phenyl, an amino protecting group, or

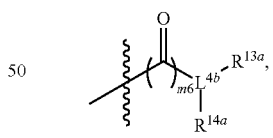

In some further embodiments, each of m6 and m7 is 1. In other embodiments, m6 is 0 and m7 is 1. In other embodiments, m6 is 1 and m7 is 0. In other embodiments, both m6 and m7 are 0. In some further embodiments, $L^{3a}$ is C$_2$-C$_6$ alkylene. In other embodiments, $L^{3a}$ is 3 to 12 or 3 to 6 membered heteroalkylene containing one, two or three heteroatoms selected from O, S or N. In further embodiment, the heteroalkylene contains one or two nitrogen atoms. In some embodiments, $L^{3b}$ is a C$_2$-C$_6$ alkylene linker. In other embodiments, $L^{3b}$ is 3 to 12 or 3 to 6 membered heteroalkylene containing one, two or three heteroatoms selected from O, S or N. In further embodiment, the heteroalkylene contains one or two nitrogen atoms. In other embodiments, each of $L^{3a}$ and $L^{3b}$ is independently optionally substituted phenylene; or C$_2$-C$_6$ alkylene or 3 to 12 membered heteroalkylene, wherein one methylene unit is replaced by an optionally substituted phenylene. In some further embodiments, each $R^{12a}$ is H, and each of $R^{9a}$, $R^{9b}$, $R^{10a}$ and $R^{10b}$ is independently H, —OR$^{11}$ or —NHR$^{12b}$, each $R^{12b}$ is independently H, —C(=O)(C$_1$-C$_6$ alkyl), —C(=O)phenyl, an amino protecting group, or

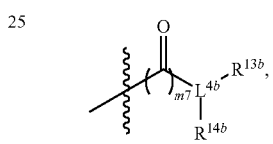

or the hydrogen in —NHR$^{12b}$ is absent, and $R^{12b}$ is a divalent amino protecting group. In some specific embodiments, $R^{12a}$ is H and $R^{12b}$ is H or an amino protecting group (e.g., Ac), and each of $R^{9a}$, $R^{9b}$, $R^{10a}$ and $R^{10b}$ is independently —NH$_2$, NH (optionally substituted C$_1$-C$_6$ alkyl), or —NHC(=O)CH$_3$. In other embodiments, $R^{11}$ is H and each of $R^{9a}$, $R^{9b}$, $R^{10a}$ and $R^{10b}$ is —OH. In other embodiments, at least one of $R^{9a}$, $R^{9b}$, $R^{10a}$ and $R^{10b}$ is H. In other embodiments, $R^{11}$ is

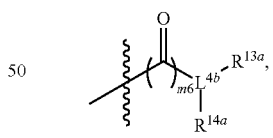

In other embodiments, $R^{12a}$ is H and $R^{12b}$ is

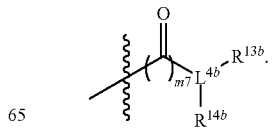

In some embodiments, $L^{4a}$ is $C_2$-$C_6$ alkylene. In other embodiments, $L^{4a}$ is 3 to 12 or 3 to 6 membered heteroalkylene containing one, two or three heteroatoms selected from O, S, or N. In further embodiment, the heteroalkylene contains one or two nitrogen atoms. In some embodiments, $L^{4b}$ is $C_2$-$C_6$ alkylene. In other embodiments, $L^{4b}$ is 3 to 12 or 3 to 6 membered heteroalkylene linker containing one, two or three heteroatoms selected from O, S or N. In further embodiment, the heteroalkylene contains one or two nitrogen atoms. In other embodiments, each of $L^{4a}$ and $L^{4b}$ is independently optionally substituted phenylene. In some such embodiments, each of $R^{13a}$, $R^{13b}$, $R^{14a}$ and $R^{14b}$ is independently H, hydroxy, or a protected hydroxy. In some other embodiments, each of $R^{13a}$, $R^{13b}$, $R^{14a}$ and $R^{14b}$ is independently H, —$NH_2$, —NH (optionally substituted $C_1$-$C_6$ alkyl), or a protected amino. In still other embodiments, at least one of $R^{13a}$, $R^{13b}$, $R^{14a}$ and $R^{14b}$ is H.

In some embodiments, the polymer of Formula (I) has the structure of Formula (Ia):

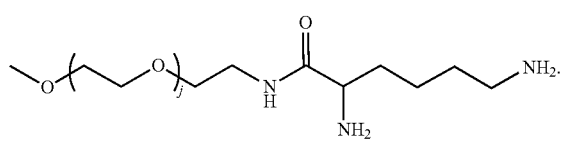
(Ia)

In other embodiments, the polymer of Formula (I) or (Ia) has the structure of Formula (Ib), (Ib-1), (Ic) or (Ic-1):

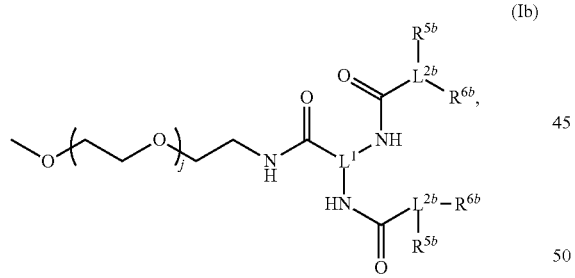
(Ib)

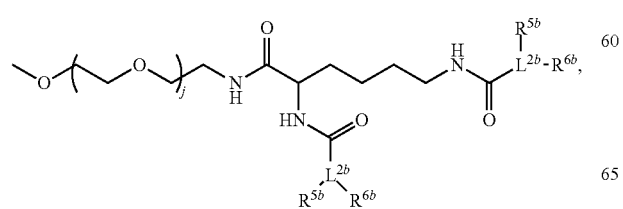
(Ib-1)

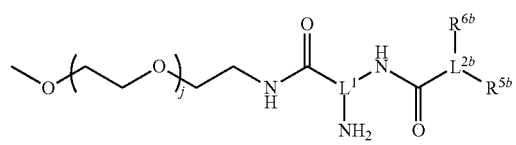
(Ic)

or

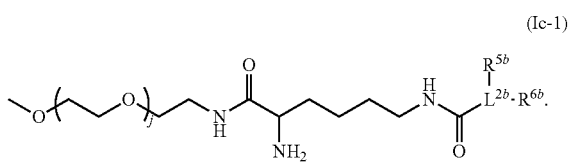
(Ic-1)

In some such embodiments, each of $R^{5b}$ and $R^{6b}$ is independently —$NH_2$ or —NHAc. In other embodiments, each of $R^{5b}$ and $R^{6b}$ is —OH. In still other embodiments, at least one of $R^{5b}$ and $R^{6b}$ is H. In further embodiments, the structure of Formula (Ib-1) also has the structure of Formula (Ib-2) or (Ib-3):

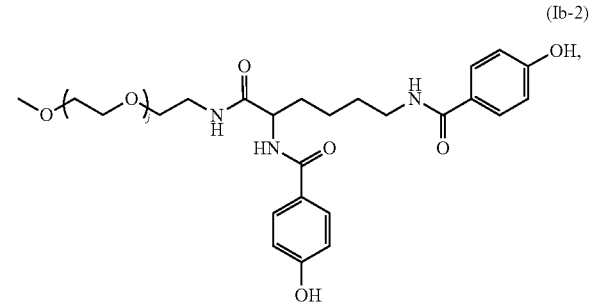
(Ib-2)

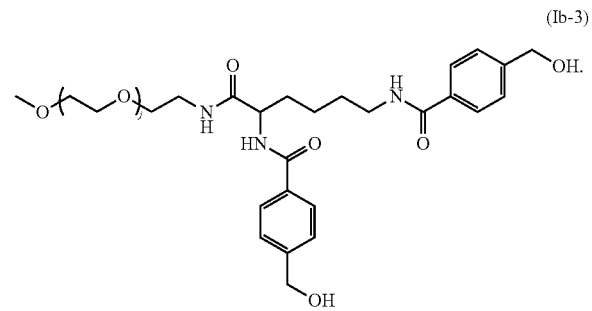
(Ib-3)

In further embodiments, the structure of Formula (Ib-1) also has the structure of Formula (Ib-4):

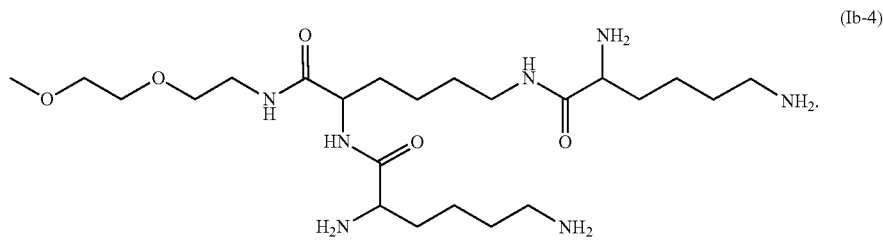 [SMILES: COCCOCCNC(=O)C(CCCCNC(=O)C(N)CCCCN)NC(=O)C(N)CCCCN]

(Ib-4)

In some embodiments, the polymer of Formula (I) has the structure of Formula (Id), (Ie), or (If)

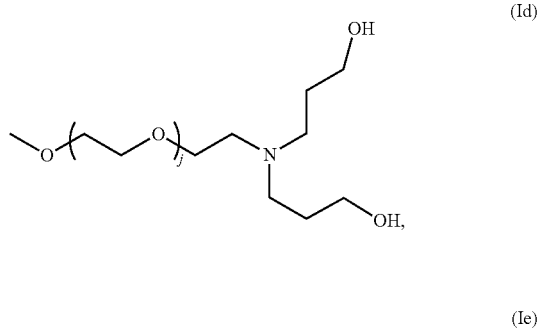

In some embodiments of the polymer of Formula (I) or any substructure thereof, j is an integer from about 50 to 1000, from about 100 to about 800, from about 200 to about 700, from from about 300 to about 600, or from about 400 to about 500. In some embodiments, the polymer has an average molecular weight of from about 5 kDa to about 100 kDa, from about 10 kDa to about 75 kDa, from about 12.5 kDa to about 50 kDa, or from about 15 kDa to about 30 kDa. In some specific embodiments, the polymer has a molecular weight of about 20 kDa.

Another aspect of the present disclosure relates to a polymer for liquid phase oligonucleotide synthesis, having the structure of Formula (II):

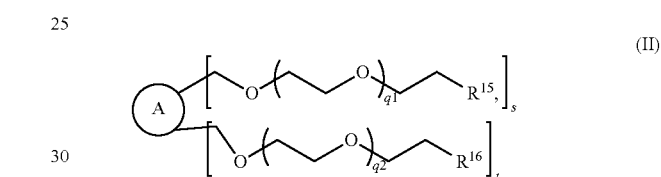

(II)

wherein:
A is selected from the group consisting of a carbon atom, a $C_2$ to $C_{20}$ alkylene; a 2 to 20 membered heteroalkylene, phenylene, 5-10 membered heteroarylene, $C_{5-10}$ cycloalkylene, and 5-10 membered heterocycloalkylene;
each $R^{15}$ is independently selected from the group consisting of —O—$C_1$-$C_6$ alkyl, —OC(O)($C_1$-$C_6$ alkyl), —OC(O)phenyl, —NHC(O)($C_1$-$C_6$ alkyl), —NHC(O) phenyl, —NHC(O)phenylene-acetoxymethyl, a protected hydroxy, or a protected amino;
each $R^{16}$ is independently —OH, —$NH_2$, or —NH (optionally substituted $C_1$-$C_6$ alkyl);
each of $q^1$ and $q^2$ is independently an integer from 10 to 500; and
each of s and t is independently an integer from 1 to 4, provided that s+t is equal to or greater than 2.

In some embodiments of the polymer of Formula (II), s+t is 4. In some specific embodiments, s is 2 and t is 2. In some embodiments, the polymer of Formula (II) has the structure of (IIa):

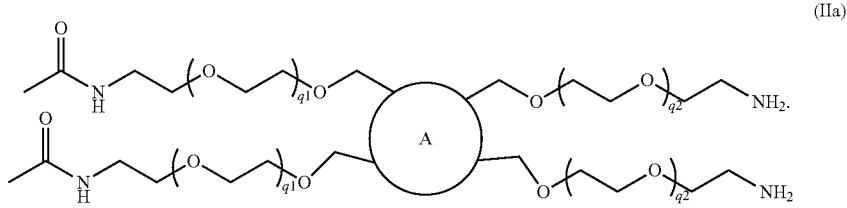

(IIa)

In some embodiments, A is a carbon atom or a phenylene. In some specific embodiments, A is a carbon atom.

In some other embodiments of the polymer of Formula (II), A is a $C_6$ to $C_{12}$ alkylene. In some such embodiments, s+t is 8. In some specific embodiments, each of s and t s 4. In other embodiments, s is 5 and t is 3, or s is 3 and t is 5. In some embodiments, the polymer of Formula (II) has the structure of Formula (IIb):

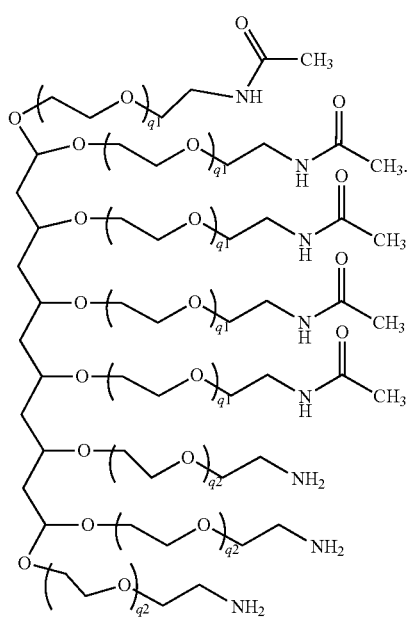

(IIb)

In some embodiments the polymer of Formula (II) (including Formula (IIa) and (IIb)), each $q^1$ is independently from about 20 to about 150, about 40 to about 100, or about 50 to about 75. In some embodiments, each $q^2$ is independently from about 30 to about 150, about 40 to about 100, or about 50 to about 75. In some embodiments, the average molecular weight of the polymer is from about 2 kDa to about 60 kDa, from about 5 kDa to about 50 kDa, from about 10 kDa to about 50 kDa, from about 15 kDa to about 30 kDa, or about 20 kDa.

Another aspect of the present disclosure relates to a method for preparing an oligonucleotide by liquid phase oligonucleotide synthesis, comprising:
  dissolving the polymer described herein in a first solvent to form a reaction matrix; and
  reacting the polymer with one or more nucleoside analogs to form a first bioconjugate comprising a structure of Formula (III):

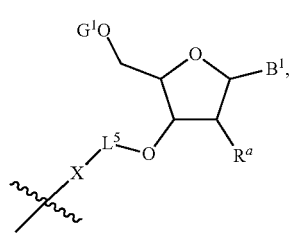

(III)

wherein
  $B^1$ is a nitrogenous base;
  $G^1$ is a 5' hydroxy blocking group;
  X is O or $NR^{20}$;
  $R^{20}$ is H or $C_1$-$C_6$ alkyl;
  $R^a$ is —H, —OH, halogen, —O—($C_1$-$C_6$ alkyl), —O—($C_1$-$C_6$ haloalkyl), or —OY, where Y is a 2' hydroxy protecting group; and
  $L^5$ is a cleavable heteroalkylene linker where one or more carbon atoms is replaced by O, S, N, C(=O) or C(=S).

In some embodiments of the method described herein, the structure of Formula (III) is also represented by Formula (IIIa):

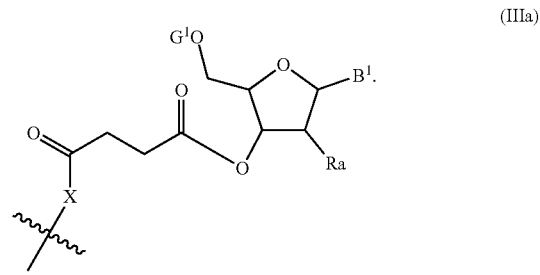

(IIIa)

In some embodiments, $B^1$ is independently optionally protected adenine, optionally protected deaza adenine, optionally protected cytosine, optionally protected guanine, optionally protected deaza guanine, optionally protected thymine or optionally protected uracil. In some embodiments, $B^1$ is

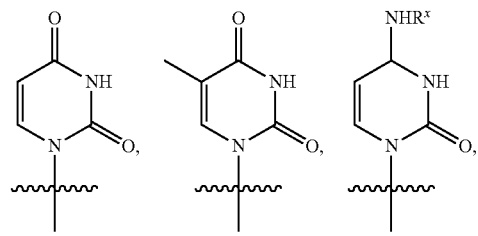

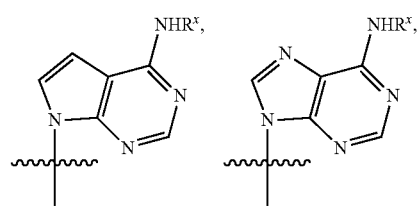

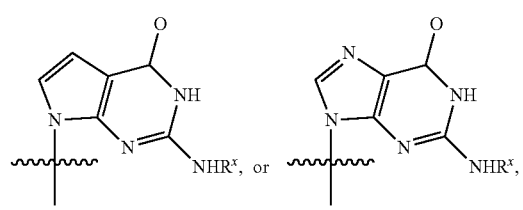

wherein R$^x$ is H, unsubstituted or substituted C$_1$-C$_6$ alkyl, or an amino protecting group, or the hydrogen in —NHR$^x$ is absent and R$^x$ is a divalent amino protecting group. In some embodiments, G$^1$ is a trityl type of hydroxy protecting group selected from the group consisting of (4-methoxyphenyl) diphenylmethyl, bis(4-methoxyphenyl)phenylmethyl, tris (4-methoxyphenyl)methyl, 9-phenylxanthen-9-yl, and 9-(4-methoxyphenyl)xanthen-9-yl. In some specific embodiments, G$^1$ is bis(4-methoxyphenyl)phenylmethyl.

In some embodiments of the method described herein, the polymer has an average molecular weight from about 10 kDa about 50 kDa, from about 15 kDa to about 30 kDa, or about 20 kDa.

In some embodiments, the method described herein further comprises: removing the 5' hydroxy blocking group (G$^1$) to form a 5' unblocked first bioconjugate; and isolating the 5' unblocked first bioconjugate. In some embodiments, the isolation of the 5' unblocked first bioconjugate is achieved by precipitation, dialysis or filtration. In some specific embodiments, the isolation of the 5' unblocked first bioconjugate is achieved by precipitation. In some such specific embodiments, the precipitation is achieved in diethyl ether. In other such specific embodiments, the precipitation is achieved in isopropanol.

In some embodiments, the method described herein further comprises:

(a) reacting the 5' unblocked first bioconjugate with one or more nucleoside phosphoramidite analogs in a second solvent to form a second bioconjugate comprising the structure of Formula (IV):

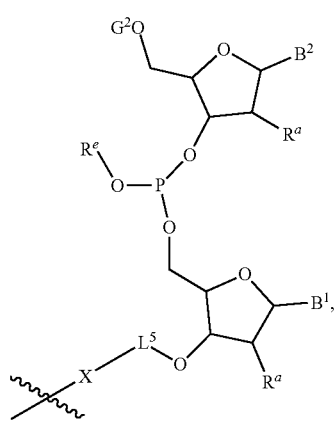

(IV)

wherein

G$^2$ is a 5' hydroxy blocking group;

B$^2$ is a nitrogenous base; and

R$^e$ is a phosphite protecting group;

(b) oxidizing the phosphite moiety in Formula (IV);

(c) removing the 5' blocking group G$^2$ to form a 5' unblocked second bioconjugate comprising the structure of Formula (IV'):

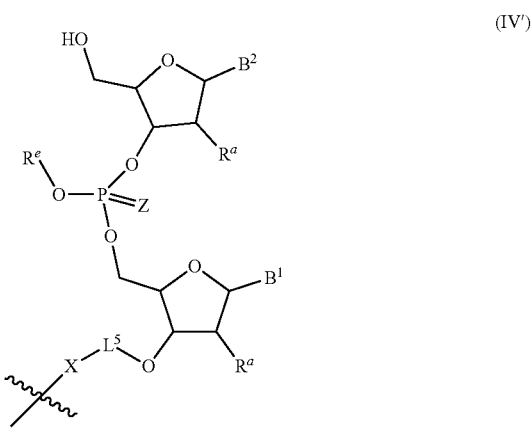

(IV')

wherein Z is O or S; and (d) isolating the 5' unblocked second bioconjugate.

In some embodiments, the structure of Formula (IV) is also represented by (IVa) and the Formula (IV') is also represented by Formula (IV'a):

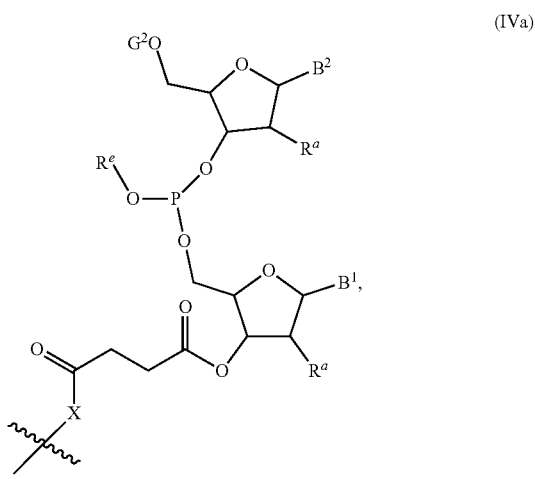

(IVa)

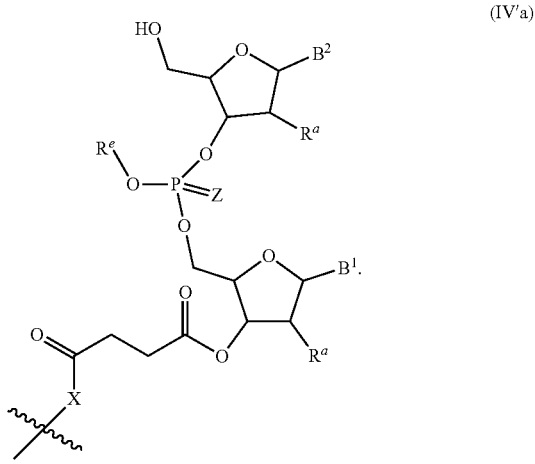

(IV'a)

In some embodiments of the method described herein, the method described herein further comprises blocking unreacted 5' hydroxy group in the 5' unblocked first bioconjugate prior to step (b). In some embodiments, B$^2$ is independently optionally protected adenine, optionally protected deaza adenine, optionally protected cytosine, optionally protected guanine, optionally protected deaza guanine, optionally protected thymine, or optionally protected uracil. In some embodiments, B² is

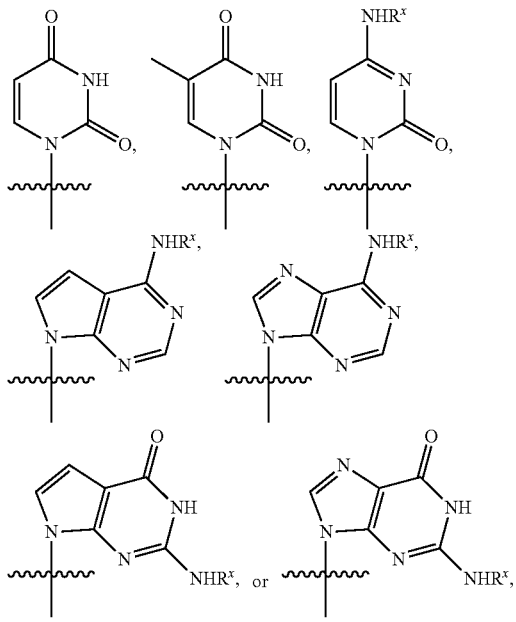

wherein $R^x$ is H, unsubstituted or substituted $C_1$-$C_6$ alkyl, or an amino protecting group, or the hydrogen in —$NHR^x$ is absent and $R^x$ is a divalent amino protecting group. In some embodiments, $G^2$ is a trityl type of hydroxy protecting group selected from the group consisting of (4-methoxyphenyl) diphenylmethyl, bis(4-methoxyphenyl)phenylmethyl, tris (4-methoxyphenyl)methyl, 9-phenylxanthen-9-yl, and 9-(4-methoxyphenyl)xanthen-9-yl. In some specific embodiments, $G^2$ is bis(4-methoxyphenyl)phenylmethyl.

In some embodiments, the isolation of the 5' unblocked second bioconjugate is achieved by precipitation, filtration, or dialysis. In some preferred embodiments, the isolation of the 5' unblocked second bioconjugate is achieved by precipitation. In some preferred embodiments, the precipitation is in diethyl ether. In other preferred embodiments, the precipitation is in isopropanol.

In some embodiments of the method described herein, steps (a)-(d) are repeated multiple cycles until one or more desired length of oligonucleotides have been synthesized. In some embodiments, steps (a)-(d) of the method described herein are repeated at least about 10 cycles. In some embodiments, the method described herein further comprises removing the oligonucleotides from the polymer.

In some embodiments, the first solvent and the second solvent comprise one or more non-protic polar solvents, or combinations thereof. In some embodiments, the one or more non-protic polar solvents comprise acetonitrile, tetrahydrofuran (THF), dimethylformamide (DMF), dimethyl sulfoxide (DMSO), dichloromethane (DCM), sulfolane, or combinations thereof. In some specific embodiments, the one or more non-protic polar solvents is acetonitrile.

A further aspect of the present disclosure relates to an oligonucleotide prepared by the methods described herein.

DETAILED DESCRIPTION

Figure 1:
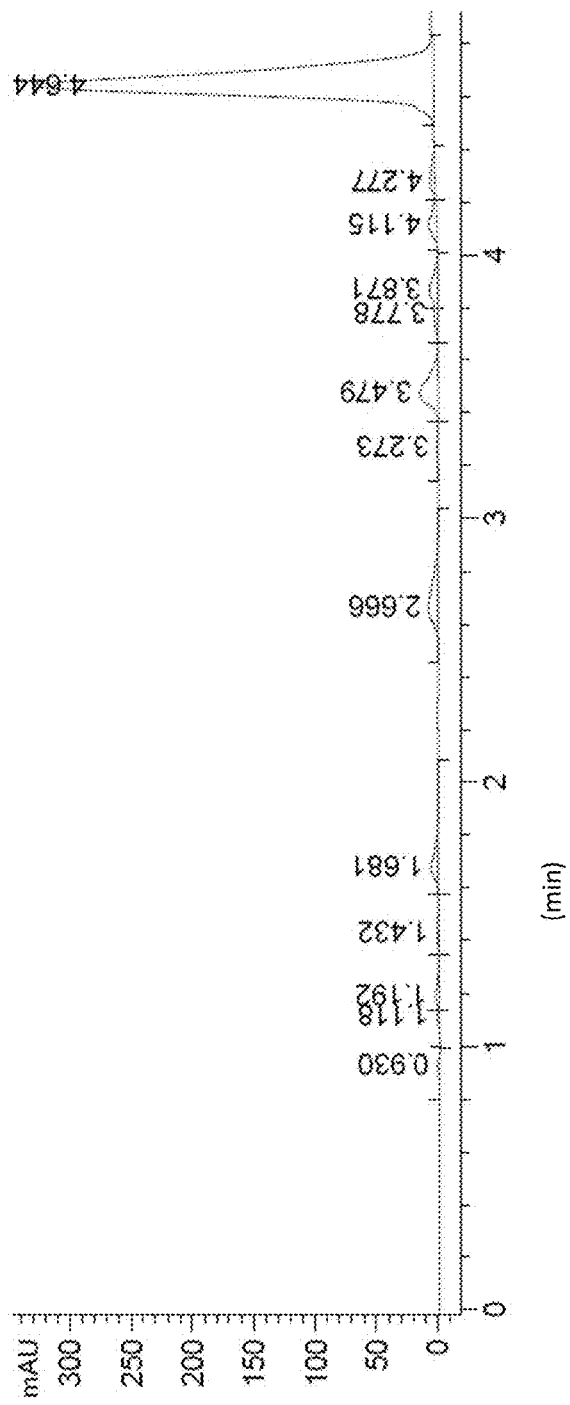
FIG. 1 is an HPLC profile of an eight dT oligonucleotide conjugate synthesized with polymer (1a) having an average molecular weight of about 20 kDa by the liquid phase method disclosed herein according to an embodiment of the present application.

Solid phase oligonucleotide synthesis enable oligo synthesis at the solid support-liquid interface. The solid support is insoluble in the liquid medium (e.g., organic solvent). Examples of solid support include particles of controlled pore glass (CPG) and porous crosslink polystyrene. In contrast, liquid phase oligo synthesis (LPOS) relies on a soluble organic compound as support (hub) to carry out oligo synthesis in solution. Conventional LPOS typically utilizes soluble supports that have one or several functional groups as anchors to conjugate and synthesize oligos. Embodiments of the present disclosure relate to methods for liquid phase oligonucleotide synthesis by using a soluble polymer that has a plurality of functional groups as anchors for oligo synthesis. For example, the polymers described herein may contain, e.g., reactive amino groups that allows for efficient conjugation with nucleoside or nucleotide analogs with improved yield compared to known liquid phase oligonucleotide synthesis and solid phase oligonucleotide synthesis. The polymers described herein include one or more polyethylene groups, the lengths of which may be controlled to efficiently reduce the trapping and non-specific adsorption of impurities in the polymer, which can result in improved performance using these polymers for liquid phase oligo synthesis. The methods described herein is amenable for multi-kilogram oligonucleotide synthesis and good loading capacity and oligo yield.

Definitions

The section headings used herein are for organizational purposes only and are not to be construed as limiting the subject matter described.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components. By "consisting of" is meant including, and limited to, whatever follows the phrase "consisting of." By "consisting essentially of" is meant including any elements listed after the phrase, and limited to other elements that do not interfere with or contribute to the activity or action specified in the disclosure for the listed elements.

As used herein, the term "average molecular weight" is the weight-average molecular weight (Mw) of a sample population made up of polymer species having a multiplicity of molecular weights. This quantity is defined by the equation:

$$M_w = \left(\sum_{i=1} n_i \times (M_i)^2\right) \bigg/ \sum_{i=1} n_i \times M_i$$

where $n_i$ indicates the number of molecules of species i and $M_i$ is the molecular weight of $i^{th}$ species. As used herein, the term "molecular weight" refers to weight average molecular weight, unless otherwise specified.

As used herein, the term "polymer" used herein in its traditional sense, is a large molecule composed of smaller monomeric or oligomeric subunits covalently linked together to form a chain. A "homopolymer" is a polymer made up of only one monomeric repeating unit. A "copolymer" refers to a polymer made up of two or more kinds of monomeric repeating unit. Linear polymers are composed of monomeric subunits linked together in one continuous length to form polymer chains. Branched polymers are similar to linear polymers but have side chains protruding from various branch points along the main polymer. Star-shaped polymers are similar to branched polymers except that multiple side branches radiate from a single branch site, resulting in a star-shaped or wheel-and-spoke appearance.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

As used herein, "alkenyl" refers to a straight or branched hydrocarbon chain containing one or more double bonds. The alkenyl group may have 2 to 20 carbon atoms. By way of example only, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2-dienyl, and buta-1,2-dien-4-yl. Typical alkenyl groups include, but are in no way limited to, ethenyl, propenyl, butenyl, pentenyl, and hexenyl, and the like. The alkenyl group may be substituted or unsubstituted.

As used herein, "alkynyl" refers to a straight or branched hydrocarbon chain containing one or more triple bonds. The alkynyl group may have 2 to 20 carbon atoms. By way of example only, "$C_2$-$C_4$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like. The alkynyl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 10 atoms in the ring(s), 3 to 8 atoms in the ring(s), or 3 to 6 atoms in the ring(s). A cycloalkyl group may be unsubstituted or substituted. Examples of monocyclic cycloalkyl groups include, but are in no way limited to, cyclopropyl, cyclobutyl, cyclopentyl, cyclohexyl, cycloheptyl and cyclooctyl. Examples of bicyclic fused cycloalkyl groups are decahydronaphthalenyl, dodecahydro-1H-phenalenyl and tetradecahydroanthracenyl; examples of bicyclic bridged cycloalkyl groups are bicyclo[1.1.1]pentyl, adamantanyl and norbornanyl; and examples of bicyclic spiro cycloalkyl groups include spiro[3.3]heptane and spiro[4.5]decane.

As used herein, "carbocyclyl" refers to a non-aromatic a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$ aryl group, or a $C_{10}$ aryl group. Examples of aryl groups include, but are not limited to, benzene and naphthalene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 5 to 10 atoms in the ring(s), 6 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, and ten-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., heterocyclyl groups are not aromatic). The heteroatom(s) is an element other than carbon including, but not limited to, oxygen, sulfur and nitrogen. A heterocycle may further contain one or more carbonyl functionalities, so as to make the definition include oxo-systems such as lactams, lactones, and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 10 atoms in the ring(s), 3 to 8 atoms in the ring(s), 3 to 6 atoms in the ring(s), or 5 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogen in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "alkylene" refers to a branched, or straight chain fully saturated di-radical chemical group containing only carbon and hydrogen that is attached to the rest of the molecule via two points of attachment. By way of example only, "$C_1$-$C_{10}$ alkylene" indicates that there are one to ten carbon atoms in the alkylene chain. Non-limiting examples include ethylene (—$CH_2CH_2$—), propylene (—$CH_2CH_2CH_2$—), butylene (—$CH_2CH_2CH_2CH_2$—), and pentylene (—$CH_2CH_2CH_2CH_2CH_2$—).

As used herein, "alkenylene" refers to a straight or branched chain di-radical chemical group containing only carbon and hydrogen and containing at least one carbon-carbon double bond that is attached to the rest of the molecule via two points of attachment. The alkenylene group may be designated as "$C_2$-$C_{10}$ alkenylene" or similar designations. By way of example only, "$C_2$-$C_{10}$ alkenylene" indicates that there are two to ten carbon atoms in the alkenylene chain.

As used herein, "alkynylene" refers to a straight or branched chain di-radical chemical group containing only carbon and hydrogen and containing at least one carbon-carbon triple bond that is attached to the rest of the molecule via two points of attachment. The alkynylene group may be designated as "$C_2$-$C_{10}$ alkenylene" or similar designations. By way of example only, "$C_2$-$C_{10}$ alkynylene" indicates that there are two to ten carbon atoms in the alkynylene chain.

As used herein, "heteroalkylene" refers to an alkylene group, as defined herein, containing one or more heteroatoms in the carbon back bone (i.e., an alkylene group in which one or more carbon atoms is replaced with a heteroatom, for example, nitrogen atom, oxygen atom or sulfur atom). For example, a —$CH_2$— may be replaced with —O—, —S—, or —NH—, or a —CH(R)— can be replaced with —N(R)—. Heteroalkylene groups include, but are not limited to ether, thioether, amino-alkylene, and alkylene-amino-alkylene moieties. In some embodiments, the heteroalkylene may include one, two, three, four, or five —$CH_2CH_2O$— unit(s). Alternatively and/or additionally, one or more carbon atoms (for example, a —$CH_2$—) can also be substituted with an oxo (=O) to become a carbonyl- C(=O)—, or be substituted with (=S) to become thiocarbonyl —C(=S)—.

As used herein, "aralkyl" and "(aryl)alkyl" refer to an aryl group, as defined above, connected, as a substituent, via an alkylene group, as described above. The alkylene and aryl group of an aralkyl may be substituted or unsubstituted. Examples include but are not limited to benzyl, 2-phenylalkyl, 3-phenylalkyl, and naphthylalkyl. In some embodiments, the alkylene is an unsubstituted straight chain containing 1, 2, 3, 4, 5, or 6 methylene unit(s).

As used herein, "heteroaralkyl" and "(heteroaryl)alkyl" refer to a heteroaryl group, as defined above, connected, as a substituent, via an alkylene group, as defined above. The alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs. In some embodiments, the alkylene is an unsubstituted straight chain containing 1, 2, 3, 4, 5, or 6 methylene unit(s).

As used herein, "(heterocyclyl)alkyl" refer to a heterocyclic or a heterocyclyl group, as defined above, connected, as a substituent, via an alkylene group, as defined above. The alkylene and heterocyclyl groups of a (heterocyclyl)alkyl may be substituted or unsubstituted. Examples include but are not limited to (tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl. In some embodiments, the alkylene is an unsubstituted straight chain containing 1, 2, 3, 4, 5, or 6 methylene unit(s).

As used herein, "cycloalkylalkyl" and "(cycloalkyl)alkyl" refer to a cycloalkyl group (as defined herein) connected, as a substituent, via an alkylene group. Examples include but are not limited to cyclopropylmethyl, cyclobutylmethyl, cyclopentylethyl, and cyclohexylpropyl. In some embodiments, the alkylene is an unsubstituted straight chain containing 1, 2, 3, 4, 5, or 6 methylene unit(s).

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "amino" refer to a —$NH_2$ group. The term "mono-substituted amino group" as used herein refers to an amino (—$NH_2$) group where one of the hydrogen atoms is replaced by a substituent. The term "di-substituted amino group" as used herein refers to an amino (—$NH_2$) group where each of the two hydrogen atoms is replaced by a substituent. The term "optionally substituted amino," as used herein refer to a —$NR_AR_B$ group where $R_A$ and $R_B$ are independently hydrogen, alkyl, cycloalkyl, aryl, heteroaryl, heterocyclyl, aralkyl, or heterocyclyl(alkyl), as defined herein.

As used herein, "alkylamino" or "(alkyl)amino" refers to a —$NR_AR_B$ group where $R_A$ and $R_B$ are hydrogen or alkyl as defined above, and at least one of $R_A$ and $R_B$ is alkyl. The alkyl portion of the (alkyl)amine, includes, for example, $C_1$-$C_6$ alkyl groups.

As used herein, "aminoalkyl" or "(amino)alkyl" refers to an alkyl group in which one or more of the hydrogen atoms are replaced by an amino group or "—$NR_AR_B$" group as defined herein. The alkyl portion of the aminoalkyl, includes, for example, $C_1$-$C_6$ alkyl.

The term "halogen atom" or "halogen" as used herein, means any one of the radio-stable atoms of column 7 of the Periodic Table of the Elements, such as, fluorine, chlorine, bromine, and iodine.

As used herein, "alkoxyalkyl" or "(alkoxy)alkyl" refers to an alkoxy group connected via an alkylene group, such as $C_2$-$C_8$ alkoxyalkyl, or ($C_1$-$C_6$ alkoxy)$C_1$-$C_6$ alkyl, for example, —$(CH_2)_{1-3}$—$OCH_3$.

As used herein, "—O-alkoxyalkyl" or "—O-(alkoxy)alkyl" refers to an alkoxy group connected via an —O-(alkylene) group, such as —O—($C_1$-$C_6$ alkoxy)$C_1$-$C_6$ alkyl, for example, —O—$(CH_2)_{1-3}$—$OCH_3$.

As used herein, "aryloxy" and "arylthio" refers to RO— and RS—, in which R is an aryl, as defined above, such as but not limited to phenyl. Both an aryloxy and arylthio may be substituted or unsubstituted.

A "sulfenyl" group refers to an "—SR" group in which R can be hydrogen, alkyl, alkenyl, alkynyl, carbocyclyl, aryl, heteroaryl, heterocyclyl, aralkyl, or heterocyclyl(alkyl), as defined above. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, carbocyclyl, aryl, heteroaryl, heterocyclyl, aralkyl, or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester or C-carboxy may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2N(R)$—" group wherein X is a halogen and R is hydrogen, alkyl, alkenyl, alkynyl, carbocyclyl, aryl, heteroaryl, heterocyclyl, aralkyl, or heterocyclyl(alkyl), as defined herein.

A "mercapto" group refers to an "—SH" group.

An "S-sulfonamido" group refers to a "—$SO_2N(R_AR_B)$" group in which $R_A$ and $R_B$ can be independently hydrogen, alkyl, alkenyl, alkynyl, carbocyclyl, aryl, heteroaryl, heterocyclyl, aralkyl, or heterocyclyl(alkyl) as defined herein. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, carbocyclyl, aryl, heteroaryl, heterocyclyl, aralkyl, or heterocyclyl(alkyl), as defined herein. An N-sulfonamido may be substituted or unsubstituted.

An "O-carbamyl" group refers to a "—OC(=O)N($R_AR_B$)" group in which $R_A$ and $R_B$ can be the same as defined with respect to S-sulfonamido. An O-carbamyl may be substituted or unsubstituted.

An "N-carbamyl" group refers to an "ROC(=O)N($R_A$)—" group in which R and $R_A$ can be the same as defined with respect to N-sulfonamido. An N-carbamyl may be substituted or unsubstituted.

An "O-thiocarbamyl" group refers to a "—OC(=S)—N($R_AR_B$)" group in which $R_A$ and $R_B$ can be the same as defined with respect to S-sulfonamido. An O-thiocarbamyl may be substituted or unsubstituted.

An "N-thiocarbamyl" group refers to an "ROC(=S)N($R_A$)—" group in which R and $R_A$ can be the same as defined with respect to N-sulfonamido. An N-thiocarbamyl may be substituted or unsubstituted.

A "C-amido" group refers to a "—C(=O)N($R_AR_B$)" group in which $R_A$ and $R_B$ can be the same as defined with respect to S-sulfonamido. A C-amido may be substituted or unsubstituted.

An "N-amido" group refers to a "RC(=O)N($R_A$)—" group in which R and $R_A$ can be the same as defined with respect to N-sulfonamido. An N-amido may be substituted or unsubstituted.

Where the numbers of substituents are not specified (e.g., haloalkyl), there may be one or more substituents present. For example, "haloalkyl" may include one or more of the same or different halogens.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition, it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns. Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

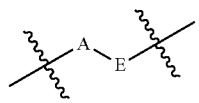

includes the substituent being oriented such that the A is attached at the leftmost attachment point of the molecule as well as the case in which A is attached at the rightmost attachment point of the molecule. In addition, if a group or substituent is depicted as

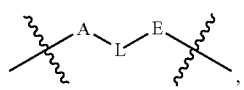

and when L is defined as a bond or absent; such group or substituent is equivalent to

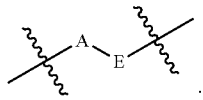

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, crystalline forms, amorphous form, solvated forms, enantiomeric forms, tautomeric forms, and the like).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl (Bn); substituted benzyl; alkylcarbonyls (e.g., t-butoxycarbonyl (BOC), acetyl (i.e., —C(=O)CH$_3$ or Ac), or isobutyryl (iBu); arylalkylcarbonyls (e.g., benzyloxycarbonyl or benzoyl (i.e., —C(=O)Ph or Bz)); substituted methyl ether (e.g., methoxymethyl ether (MOM)); substituted ethyl ether (e,g, methoxyethyl ether (MOE); a substituted benzyl ether; tetrahydropyranyl ether; silyl ethers (e.g., trimethylsilyl (TMS), triethylsilyl, triisopropylsilyl, t-butyldimethylsilyl (TBDMS), tri-iso-propylsilyloxymethyl (TOM), or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

The term "leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof, such as deazapurine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, deazapurine, 7-deazapurine, adenine, 7-deaza adenine, guanine, 7-deaza guanine, hypoxanthine, xanthine, alloxanthine, 7-alkylguanine (e.g., 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, "derivative" or "analogue" means a synthetic nucleoside or nucleotide derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate, phosphoramidite, and phosphoramidate linkages. "Derivative" and "analog" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

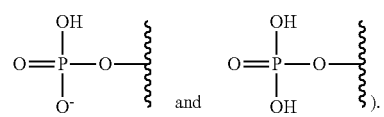 [SMILES: *OP(=O)([O-])O ; *OP(=O)(O)O]

As used herein, the terms "monophosphate," "diphosphate," and "triphosphate" are used in their ordinary sense as understood by those skilled in the art, and include protonated forms.

As used herein, "loading capacity" or "load" is expressed in mmol or µmol of a nucleoside bound to the polymer described herein per gram of polymer (i.e., mmol/g).

Polymers for Liquid Phase Oligonucleotide Synthesis

Several aspects of the present application relate to a polymer for liquid phase synthesis. In some embodiments, the liquid phase synthesis comprises liquid phase oligonucleotide synthesis, liquid phase peptide synthesis, liquid phase polynucleotide (i.e., nucleic acid), synthesis or liquid phase small molecule synthesis. In some embodiments, the polymer comprises or is a polymer for liquid phase oligonucleotide synthesis. The polymer may include poly(ethylene glycol) (PEG) pendant arms with reactive groups, including but not limited to amine, alcohol, azide or alkyne groups or combinations thereof, that allows for reaction with nucleoside or nucleotide analogs. The average molecular weight of the polymer may be controlled by controlling the length of the pendant PEG arms. The length of the PEG arms can be modulated in a manner to reduce trapping of impurities, allowing for improved performance of these structures for liquid phase oligo synthesis.

Polymer of Formula (I) or (I')

Some embodiments of the present disclosure relate to a polymer for liquid phase oligonucleotide synthesis, having the structure of Formula (I):

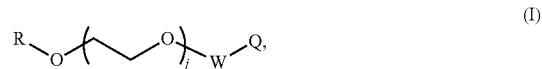

wherein:
R is H, or unsubstituted or substituted $C_1$-$C_6$ alkyl;
W is $C_1$-$C_{20}$ alkylene, a 2 to 20 membered heteroalkylene, or a bond;
Q is

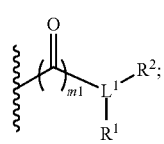

$L^1$ is $C_1$-$C_{20}$ alkylene, 2 to 20 membered heteroalkylene, optionally substituted phenylene, optionally substituted 5 to 6 membered heteroarylene, optionally substituted 3 to 10 membered heterocyclylene, or optionally substituted $C_3$-$C_{10}$ cycloalkylene, or $C_1$-$C_{20}$ alkylene or 2 to 20 membered heteroalkylene in which one or more methylene repeating units is each independently replaced by a group selected from the group consisting of optionally substituted phenylene, optionally substituted 5 to 6 membered heteroarylene, optionally substituted 3 to 10 membered heterocyclylene, optionally substituted $C_3$-$C_{10}$ cycloalkylene, —C(=O)—, —CH=CH—, and —C≡C—;

each of $R^1$ and $R^2$ is independently —$OR^3$ or —$NR^{4a}R^{4b}$;

$R^3$ is H, $C_1$-$C_6$ alkyl, a hydroxy protecting group, or

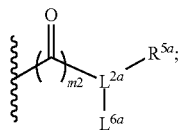

each of $R^{4a}$ and $R^{4b}$ is H, optionally substituted $C_1$-$C_6$ alkyl, —C(=O)($C_1$-$C_6$ alkyl), —C(=O)phenyl, an amino protecting group, or

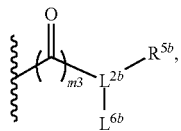

or $R^{4a}$ and $R^{4b}$ taken together is a divalent amino protecting group;

each of $L^{2a}$ and $L^{2b}$ is independently $C_1$-$C_{20}$ alkylene, 2 to 20 membered heteroalkylene, optionally substituted phenylene, optionally substituted 5 to 6 membered heteroarylene, optionally substituted 3 to 10 membered heterocyclylene, or optionally substituted $C_3$-$C_{10}$ cycloalkylene, or $C_1$-$C_{20}$ alkylene or 2 to 20 membered heteroalkylene in which one or more methylene repeating units is each independently replaced by a group selected from the group consisting of optionally substituted phenylene, optionally substituted 5 to 6 membered heteroarylene, optionally substituted 3 to 10 membered heterocyclylene, optionally substituted $C_3$-$C_{10}$ cycloalkylene, —C(=O)—, —CH=CH—, and —C≡C—;

each of $R^{5a}$, $R^{5b}$, $R^{6a}$ and $R^{6b}$ is independently H, —$OR^7$ or —$NR^{8a}R^{8b}$;

each of $R^7$ is independently H, $C_1$-$C_6$ alkyl, a hydroxy protecting group, or

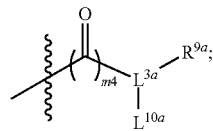

each of $R^{8a}$ and $R^{8b}$ is independently H, optionally substituted $C_1$-$C_6$ alkyl, —C(=O)($C_1$-$C_6$ alkyl), —C(=O)phenyl, an amino protecting group, or

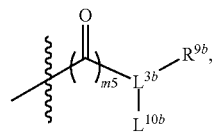

or $R^{8a}$ and $R^{8b}$ taken together is a divalent amino protecting group;

each of $L^{3a}$ and $L^{3b}$ is independently $C_1$-$C_{20}$ alkylene, 2 to 20 membered heteroalkylene, optionally substituted phenylene, optionally substituted 5 to 6 membered heteroarylene, optionally substituted 3 to 10 membered heterocyclylene, or optionally substituted $C_3$-$C_{10}$ cycloalkylene, or $C_1$-$C_{20}$ alkylene or 2 to 20 membered heteroalkylene in which one or more methylene repeating units is each independently replaced by a group selected from the group consisting of optionally substituted phenylene, optionally substituted 5 to 6 membered heteroarylene, optionally substituted 3 to 10 membered heterocyclylene, optionally substituted $C_3$-$C_{10}$ cycloalkylene, —C(=O)—, —CH=CH—, and —C≡C—;

each of $R^{9a}$, $R^{9b}$, $R^{10a}$ and $R^{10b}$ is independently H, —$OR^{11}$ or —$NR^{12a}R^{12b}$;

each of $R^{11}$ is independently H, $C_1$-$C_6$ alkyl, a hydroxy protecting group, or

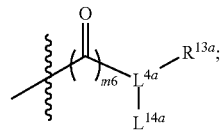

each of $R^{12a}$ and $R^{12b}$ is independently H, optionally substituted $C_1$-$C_6$ alkyl, —C(=O)($C_1$-$C_6$ alkyl), —C(=O)phenyl, an amino protecting group, or

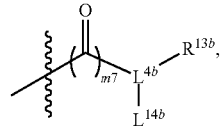

or $R^{12a}$ and $R^{12b}$ taken together is a divalent amino protecting group;

each of $L^{4a}$ and $L^{4b}$ is independently $C_1$-$C_{20}$ alkylene, 2 to 20 membered heteroalkylene, optionally substituted phenylene, optionally substituted 5 to 6 membered heteroarylene, optionally substituted 3 to 10 membered heterocyclylene, or optionally substituted $C_3$-$C_{10}$ cycloalkylene, or $C_1$-$C_{20}$ alkylene or 2 to 20 membered heteroalkylene in which one or more methylene repeating units is each independently replaced by a group selected from the group consisting of optionally substituted phenylene, optionally substituted 5 to 6 membered heteroarylene, optionally substituted 3 to 10 membered heterocyclylene, optionally substituted $C_3$-$C_{10}$ cycloalkylene, —C(=O)—, —CH=CH—, and —C≡C—;

each of $R^{13a}$, $R^{13b}$, $R^{14a}$ and $R^{14b}$ is independently H, —OH, protected hydroxy, —$NH_2$, —NH (optionally substituted $C_1$-$C_6$ alkyl), or protected amino;

each of m1, m2, m3, m4, m5, m6 and m7 is independently 0 or 1; and j is an integer from 15 to 1500. In some embodiments, each $R^{4a}$ is H, each $R^{4b}$ is independently H, —C(=O)(C$_1$-C$_6$ alkyl), —C(=O)phenyl, an amino protecting group, or

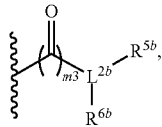

or the hydrogen in —NHR$^{4b}$ is absent, and R$^{4b}$ is a divalent amino protecting group; each $R^{8a}$ is H, and each of $R^{5a}$, $R^{5b}$, $R^{6a}$ and $R^{6b}$ is independently H, —OR$^7$ or —NHR$^{8b}$, each $R^{8b}$ is independently H, —C(=O)(C$_1$-C$_6$ alkyl), —C(=O)phenyl, an amino protecting group, or

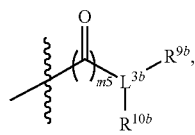

or the hydrogen in —NHR$^{8b}$ is absent, and R$^{8b}$ is a divalent amino protecting group; each $R^{12a}$ is H, and each of $R^{9a}$, $R^{9b}$, $R^{10a}$ and $R^{10b}$ is independently H, —OR$^{11}$ or —NHR$^{12b}$, each $R^{12b}$ is independently H, —C(=O)(C$_1$-C$_6$ alkyl), —C(=O)phenyl, an amino protecting group, or

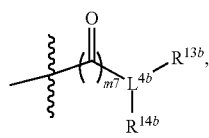

or the hydrogen in —NHR$^{12b}$ is absent, and R$^{12b}$ is a divalent amino protecting group.

In some embodiments of the polymer of Formula (I), R is unsubstituted C$_1$-C$_6$ alkyl (e.g., —CH$_3$). In other embodiments, R is substituted C$_1$-C$_6$ alkyl (e.g., methyl, ethyl, n-propyl, isopropyl, n-butyl, t-butyl independently substituted with azido or alkyne group). In some other embodiment, R is H. In some embodiments, W is —CH$_2$CH$_2$NH—. In other embodiments, W is —CH$_2$CH$_2$O—. In some embodiments, W is C$_2$-C$_6$ alkylene, such as —CH$_2$CH$_2$—. In another embodiment, W is a bond.

In some embodiments of the polymer described herein, the polymer of Formula (I) may also be represented by structure of Formula (I'):

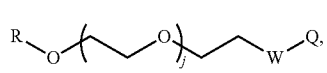
(I')

wherein:
R is C$_1$-C$_6$ alkyl;
W is —NH— or —O—;
Q is

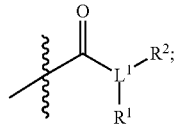

L$^1$ is a C$_1$-C$_{10}$ alkylene linker or 2 to 10 membered heteroalkylene linker;
each of R$^1$ and R$^2$ is independently —OR$^3$ or —NR$^{4a}$R$^{4b}$;
R$^3$ is H, C$_1$-C$_6$ alkyl, a hydroxy protecting group,

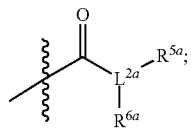

each of R$^{4a}$ and R$^{4b}$ is H, optionally substituted C$_1$-C$_6$ alkyl, —C(=O)(C$_1$-C$_6$ alkyl), —C(=O)phenyl, an amino protecting group, or

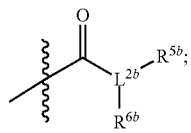

or R$^{4a}$ and R$^{4b}$ taken together is a divalent amino protecting group;
each of L$^{2a}$ and L$^{2b}$ is independently a C$_1$-C$_{10}$ alkylene linker or a 2 to 10 membered heteroalkylene linker;
each of R$^{5a}$, R$^{5b}$, R$^{6a}$ and R$^{6b}$ is independently hydrogen, —OR$^7$ or —NR$^{8a}$R$^{8b}$;
each of R$^7$ is independently H, C$_1$-C$_6$ alkyl, a hydroxy protecting group, or

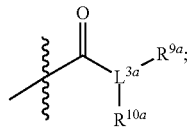

each of R$^{8a}$ and R$^{8b}$ is independently H, optionally substituted C$_1$-C$_6$ alkyl, —C(=O)(C$_1$-C$_6$ alkyl), —C(=O)phenyl, an amino protecting group, or

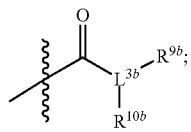

or R$^{8a}$ and R$^{8b}$ taken together is a divalent amino protecting group;
each of L$^{3a}$ and L$^{3b}$ is independently a C$_1$-C$_{10}$ alkylene linker or a 2 to 10 membered heteroalkylene linker;

each of $R^{9a}$, $R^{9b}$, $R^{10a}$ and $R^{10b}$ are independently —$OR^{11}$ or —$NR^{12a}R^{12b}$;

each of $R^{11}$ is independently H, $C_1$-$C_6$ alkyl, a hydroxy protecting group, or

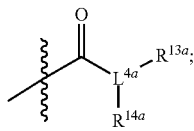

each of $R^{12a}$ and $R^{12b}$ is independently H, optionally substituted $C_1$-$C_6$ alkyl, —C(=O)($C_1$-$C_6$ alkyl), —C(=O)phenyl, an amino protecting group, or

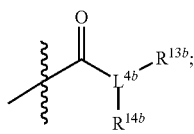

or $R^{12a}$ and $R^{12b}$ taken together is a divalent amino protecting group;

each of $L^{4a}$ and $L^{4b}$ is independently a $C_1$-$C_{10}$ alkylene linker or a 2 to 10 membered heteroalkylene linker;

each of $R^{13a}$, $R^{13b}$, $R^{14a}$ and $R^{14b}$ is independently H, —OH, a protected hydroxy, —$NH_2$, —NH (optionally substituted $C_1$-$C_6$ alkyl), or a protected amino; and j is an integer from 15 to 1500. In some embodiments, each $R^4$ is H, each $R^b$ is independently H, —C(=O)($C_1$-$C_6$ alkyl), —C(=O)phenyl, an amino protecting group, or

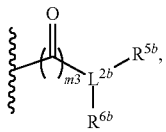

or the hydrogen in —$NHR^{4b}$ is absent, and $R^{4b}$ is a divalent amino protecting group; each $R^{8a}$ is H, and each of $R^{5a}$, $R^{5b}$, $R^{6a}$ and $R^{6b}$ is independently H, —$OR^7$ or —$NHR^{8b}$, each $R^{8b}$ is independently H, —C(=O)($C_1$-$C_6$ alkyl), —C(=O)phenyl, an amino protecting group, or

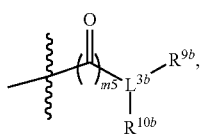

or the hydrogen in —$NHR^{8b}$ is absent, and $R^{8b}$ is a divalent amino protecting group; each $R^{12a}$ is H, and each of $R^{9a}$, $R^{9b}$, $R^{10a}$ and $R^{10b}$ is independently H, —$OR^{11}$ or —$NHR^{12b}$, each $R^{12b}$ is independently H, —C(=O)($C_1$-$C_6$ alkyl), —C(=O)phenyl, an amino protecting group, or

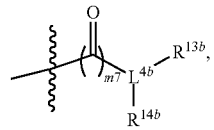

or the hydrogen in —$NHR^{12b}$ is absent, and $R^{12b}$ is a divalent amino protecting group. In some such embodiments of the polymer of Formula (I'), R is methyl. In one embodiment, W is —NH—. In another embodiment, W is —O—.

In some such embodiments of the polymer of Formula (I) or (I'), $L^1$ is $C_2$-$C_6$ alkylene. In some embodiments of the polymer of Formula (I), $L^1$ is a 3 to 12, 3 to 8, 3 to 6, or 4 to 6 membered heteroalkylene containing one, two or three heteroatoms selected from N, O, S, C(=O) or C(=S). In further embodiment, the heteroalkylene contains one or two nitrogen atoms.

In some further embodiments of the polymer of Formula (I) or (I'), Q is

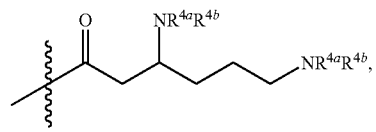

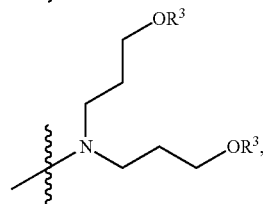

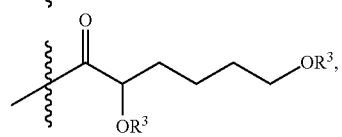

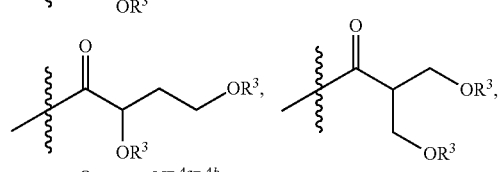

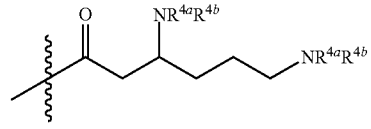

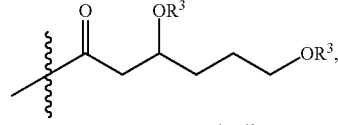

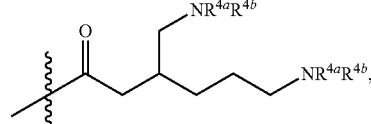

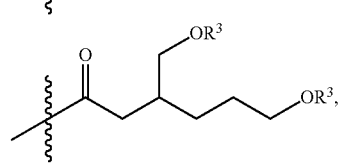

-continued

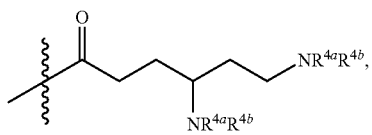

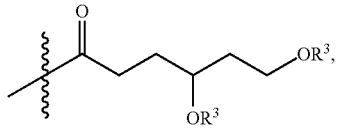

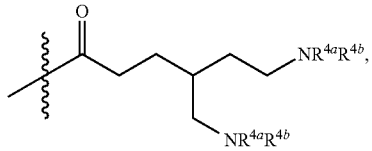

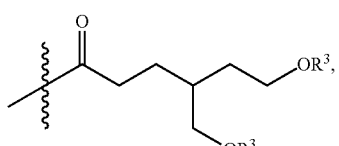

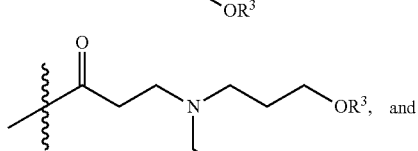, and

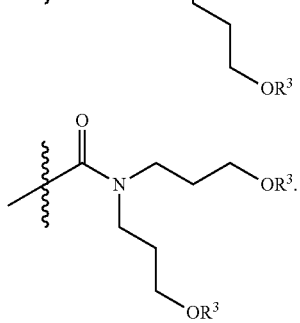

In some such embodiments, each $R^3$ is independently H or a hydroxy protecting group. In some embodiments, each $R^{4a}$ is H. In some embodiments, each $R^{4a}$ and $R^{4b}$ is H, optionally substituted $C_1$-$C_6$ alkyl, —C(=O)CH$_3$, or an amino protecting group. In some embodiments of the polymer of Formula (I), one of $R^3$ is H and the other $R^3$ is

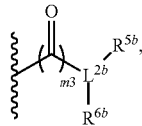

In some embodiments, $R^{4a}$ is H and $R^{4b}$ is

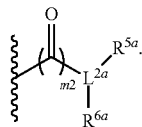

In other embodiments, $R^3$ is H, $R^{4a}$ is H, and $R^{4b}$ is

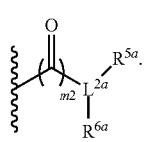

or $R^{4a}$ is H, $R^{4b}$ is H, and $R^3$ is

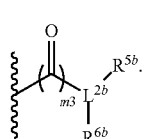

In other embodiments, each of $R^3$ is independently

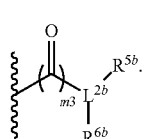

In still other embodiments, each of $R^{4a}$ and $R^{4b}$ is independently

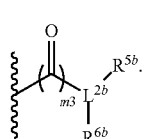

In some further embodiments, each of m2 and m3 is 1. In other embodiments, m2 is 0 and m3 is 1. In other embodiments, m2 is 1 and m3 is 0. In other embodiments, both m2 and m3 are 0. In some embodiments of the polymer of Formula (I'), one of $R^3$ is H and the other $R^3$ is

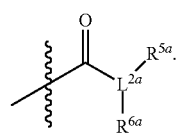

In some embodiments, $R^{4a}$ is H and $R^{4b}$ is

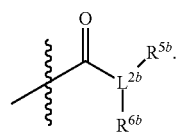

In other embodiments, $R^3$ is H $R^{4a}$ is H, and $R^{4b}$ is

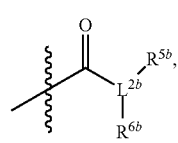

or $R^{4a}$ is H, $R^{4b}$ is H, and $R^3$ is

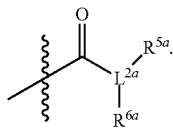

In other embodiments, each of $R^3$ is independently

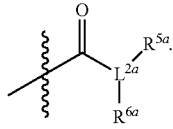

In still other embodiments, each of $R^{4a}$ and $R^{4b}$ is independently

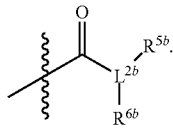

In some further embodiments of the polymer of Formula (I) or (I'), Q is selected from the group consisting of

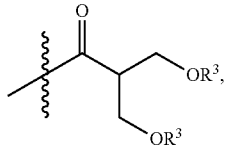

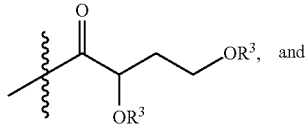

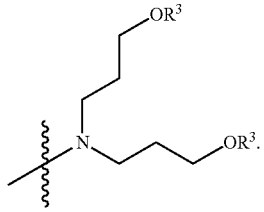

In some such embodiments, each $R^3$ is independently H or a hydroxy protecting group. In some other embodiments, each $R^3$ is

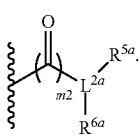

In still other embodiments, one of $R^3$ is H and the other $R^3$ is

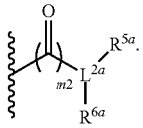

In some further embodiments, m2 is 1. In other embodiments, m2 is 0.

In some embodiments of the polymer of Formula (I) or (I'), each of $L^{2a}$ and $L^{2b}$ is independently a $C_1$-$C_{10}$ alkylene linker or a 2 to 10 membered heteroalkylene linker. In some other embodiments, each of $L^{2a}$ and $L^{2b}$ is independently 3 to 12, 3 to 8, 3 to 6, or 4 to 6 membered heteroalkylene containing one, two or three heteroatoms selected from N, O, S, C(=O) or C(=S). In further embodiment, the heteroalkylene contains one or two nitrogen atoms. In other embodiments of the polymer of Formula (I), each of $L^{2a}$ and $L^{2b}$ is independently an optionally substituted phenylene; or a $C_2$-$C_6$ alkylene or 3 to 12 membered heteroalkylene wherein one methylene unit is replaced by an optionally substituted phenylene.

In some embodiments of the polymer of Formula (I), each of $R^{5a}$, $R^{5b}$, $R^{6a}$ and $R^{6b}$ is independently hydrogen, —OH, a protected hydroxy, —NH$_2$, —NH (optionally substituted $C_1$-$C_6$ alkyl), —NHC(=O)CH$_3$, or a protected amino. In some such embodiment, at least one of $R^{5a}$, $R^{5b}$, $R^{6a}$ and $R^{6b}$ is H. In some embodiments of the polymer of Formula (I'), each of $R^{5a}$, $R^{5b}$, $R^{6a}$ and $R^{6b}$ is independently —OH, a protected hydroxy, —NH$_2$, —NH (optionally substituted $C_1$-$C_6$ alkyl), —NHC(=O)CH$_3$, or a protected amino (such as —NHAc). In some embodiments of the polymer of Formula (I) or (I'), each of $R^{5a}$, $R^{5b}$, $R^{6a}$ and $R^{6b}$ is a hydroxy or protected hydroxy. In other embodiments, each of $R^{5a}$, $R^{5b}$, $R^{6a}$ and $R^{6b}$ is —NH$_2$, —NH (optionally substituted $C_1$-$C_6$ alkyl), or protected amino (such as —NHAc). In other embodiments of the polymer of Formula (I), at least one of $R^7$ is

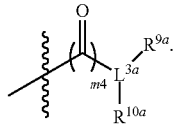

In still other embodiments, at least one of $R^{8a}$ and $R^{8b}$ is

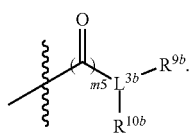

In other embodiments, each of $R^7$ is independently

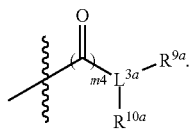

In other embodiments, each $R^{8a}$ is H and each of $R^{8b}$ is independently

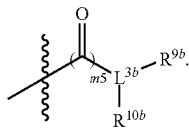

In some further embodiments, each of m4 and m5 is 1. In other embodiments, m4 is 0 and m5 is 1. In other embodiments, m4 is 1 and m5 is 0. In other embodiments, both m4 and m5 are 0. In other embodiments of the polymer of Formula (I) or Formula (I'), at least one of $R^{5a}$, $R^{5b}$, $R^{6a}$ and $R^{6b}$ is independently —$OR^7$ and at least one of $R^7$ is

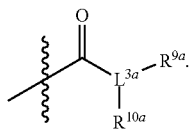

In still other embodiments, at least one of $R^{5a}$, $R^{5b}$, $R^{6a}$ and $R^{6b}$ is independently —$NR^{8a}R^{8b}$ and at least one of $R^{8a}$ and $R^{8b}$ is

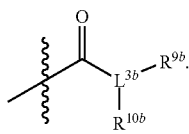

In other embodiments, each one of $R^{5a}$, $R^{5b}$, $R^{6a}$ and $R^{6b}$ is independently —$OR^7$ and each of $R^7$ is independently

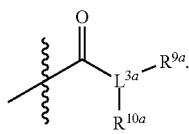

In other embodiments, each $R^{8a}$ is H and each one of $R^{5a}$, $R^{5b}$, $R^{6a}$ and $R^{6b}$ is independently —$NHR^{8b}$, and each of $R^{8b}$ is independently

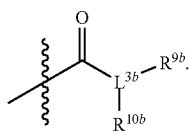

In some such embodiments of the polymer of Formula (I) or (I'), $L^{3a}$ is $C_2$-$C_6$ alkylene. In other embodiments, $L^{3a}$ is 3 to 12, 3 to 8, 3 to 6, or 4 to 6 membered heteroalkylene containing one, two or three heteroatoms selected from N, O, S, C(=O) or C(=S). In further embodiment, the heteroalkylene contains one or two nitrogen atoms. In some embodiments, $L^{3b}$ is $C_2$-$C_6$ alkylene. In other embodiments, $L^{3b}$ is 3 to 12, 3 to 8, 3 to 6, or 4 to 6 membered heteroalkylene containing one, two or three heteroatoms selected from N, O, S, C(=O) or C(=S). In further embodiment, the heteroalkylene contains one or two nitrogen atoms. In other embodiments of the polymer of Formula (I), each of $L^{3a}$ and $L^{3b}$ is independently an optionally substituted phenylene; or a $C_2$-$C_6$ alkylene or 3 to 12 membered heteroalkylene wherein one methylene unit is replaced by an optionally substituted phenylene. In some embodiments of the polymer of Formula (I), each $R^{9a}$, $R^{9b}$, $R^{10a}$ and $R^{10b}$ is independently H, —OH, a protected hydroxy, —$NH_2$, —NH (optionally substituted $C_1$-$C_6$ alkyl), —NHC(=O)$CH_3$, or a protected amino (such as —NHAc). In some such embodiments, at least one of $R^{9a}$, $R^{9b}$, $R^{10a}$ and $R^{10b}$ is H. In some embodiments of the polymer of Formula (I'), each of $R^{9a}$, $R^{9b}$, $R^{10a}$ and $R^{10b}$ is independently —OH, a protected hydroxy, —$NH_2$, —NH (optionally substituted $C_1$-$C_6$ alkyl), —NHC(=O)$CH_3$, or a protected amino. In some embodiments of the polymer of Formula (I) or (I'), each of $R^{9a}$, $R^{9b}$, $R^{10a}$ and $R^{10b}$ is a hydroxy or protected hydroxy. In other embodiments, each of $R^{9a}$, $R^{9b}$, $R^{10a}$ and $R^{10b}$ is —$NH_2$, —NH (optionally substituted $C_1$-$C_6$ alkyl), or protected amino (such as —NHAc). In other embodiments of the polymer of Formula (I) or (I'), at least one of $R^{9a}$, $R^{9b}$, $R^{10a}$ and $R^{10b}$ is independently —$OR^{11}$ and at least one of $R^{11}$ is

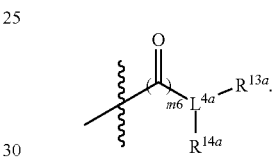

In still other embodiments, at least one of $R^{9a}$, $R^{9b}$, $R^{10a}$ and $R^{10b}$ is independently $NR^{12a}R^{12b}$ and at least one $R^{12a}$ and $R^{12b}$ is

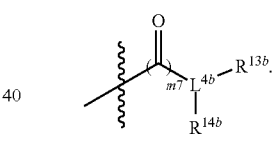

In other embodiments, each one of $R^{9a}$, $R^{9b}$, $R^{10a}$ and $R^{10b}$ is independently —$OR^{11}$ and each of $R^{11}$ is independently

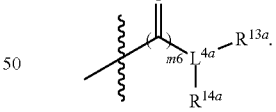

In other embodiments, each of $R^{12a}$ is H and each one of $R^{9a}$, $R^{9b}$, $R^{10a}$ and $R^{10b}$ is —$NHR^{12b}$ and each of $R^{12b}$ is independently

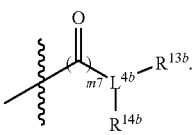

In some further embodiments, each of m6 and m7 is 1. In other embodiments, m6 is 0 and m7 is 1. In other embodiments, m6 is 1 and m7 is 0. In other embodiments, both m6 and m7 are 0. In other embodiments of the polymer of Formula (I'), at least one of $R^{11}$ is

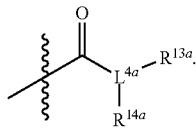

In still other embodiments, at least one $R^{12a}$ and $R^{12b}$ is

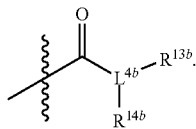

In other embodiments, each of $R^{11}$ is independently

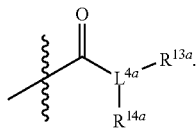

In other embodiments, each $R^{12a}$ is H and each $R^{12b}$ is independently

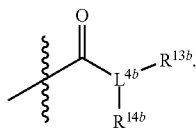

In some such embodiments of the polymer of Formula (I) or (I'), $L^{4a}$ is $C_2$-$C_6$ alkylene. In other embodiments, $L^{4a}$ is 3 to 12, 3 to 8, 3 to 6, or 4 to 6 membered heteroalkylene containing one, two or three heteroatoms selected from N, O, S, C(=O) or C(=S). In further embodiment, the heteroalkylene contains one or two nitrogen atoms. In some embodiments, $L^{4b}$ is $C_2$-$C_6$ alkylene. In other embodiments, $L^{4b}$ is 3 to 12, 3 to 8, 3 to 6, or 4 to 6 membered heteroalkylene containing one, two or three heteroatoms selected from N, O, S, C(=O) or C(=S). In further embodiment, the heteroalkylene contains one or two nitrogen atoms. In other embodiments of the polymer of Formula (I), each of $L^{4a}$ and $L^{4b}$ is independently an optionally substituted phenylene; or a $C_2$-$C_6$ alkylene or 3 to 12 membered heteroalkylene wherein one methylene unit is replaced by an optionally substituted phenylene. In some such embodiments, each of $R^{13a}$, $R^{13b}$, $R^{14a}$ and $R^{14b}$ independently H, —OH or a protected hydroxy, provided that the polymer contains at least one, two, three, four, five or six terminal hydroxy or protected hydroxy functional group. In some other embodiments, each of $R^{13a}$, $R^{13b}$, $R^{14a}$ and $R^{14b}$ independently H, —NH$_2$, —NH (optionally substituted $C_1$-$C_6$ alkyl), or a protected amino group, provided that the polymer contains at least one, two, three, four, five or six terminal amino, —NH (optionally substituted $C_1$-$C_6$ alkyl), or protected amino functional group (such as —NHAc).

In some embodiments, the polymer of Formula (I) or (I') has the structure of Formula (Ia):

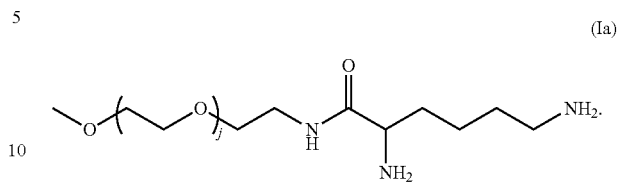

In some embodiments, the polymer of Formula (I) or (I') has the structure of Formula (Ia'):

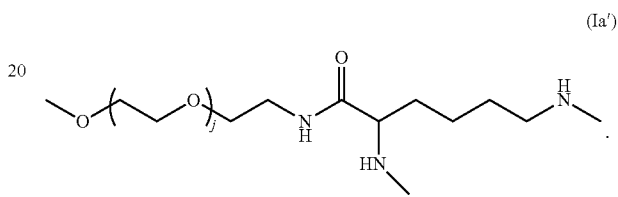

In some other embodiments, the polymer of Formula (I) or (I') has the structure of Formula (Ib), (Ib-1), (Ic) or (Ic-1):

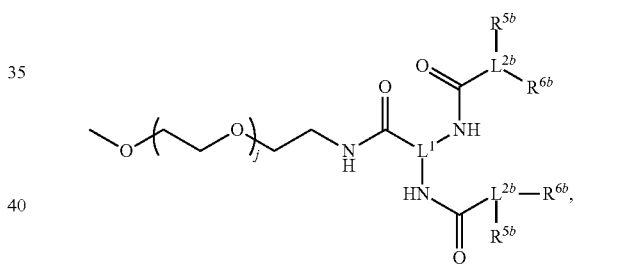

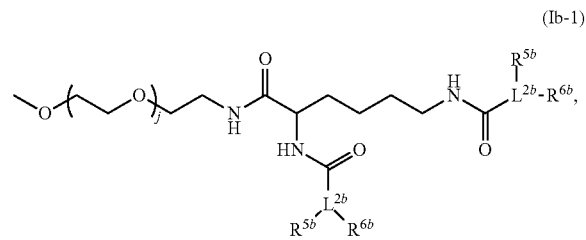

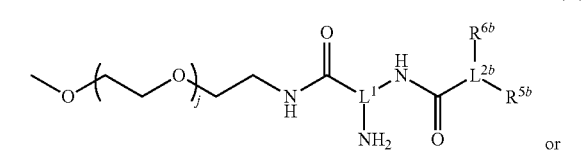

or

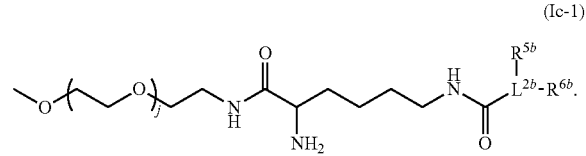

In some embodiments, the polymer of Formula (I) has the structure

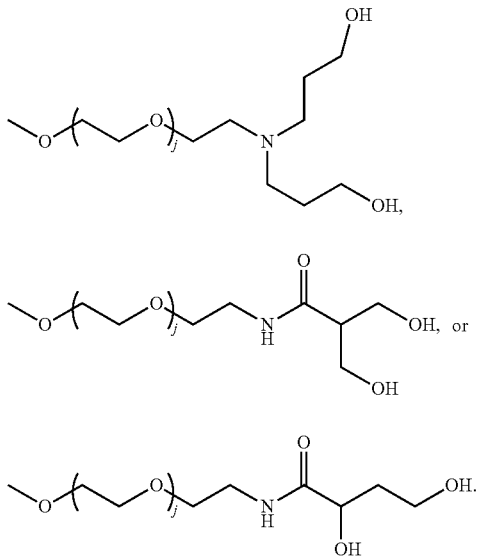

(Id)

(Ie)

(If)

In some embodiments, the polymer of Formula (I) has the structure

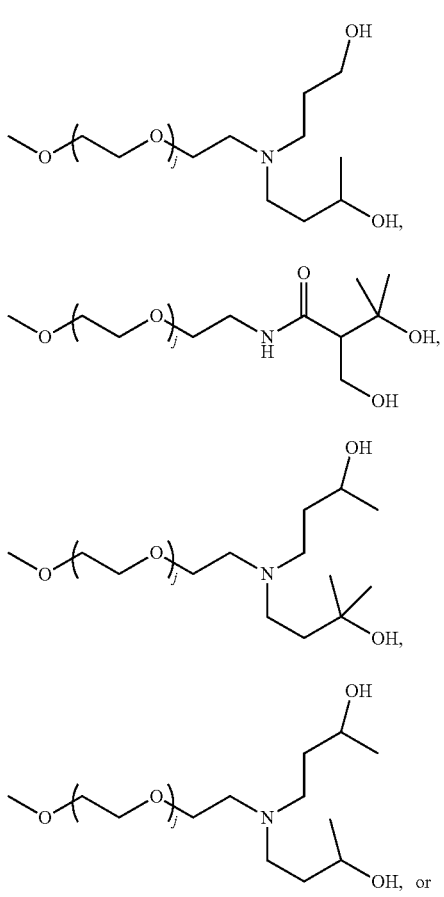

(Ig)

(Ih)

(Ij)

(Ik)

-continued

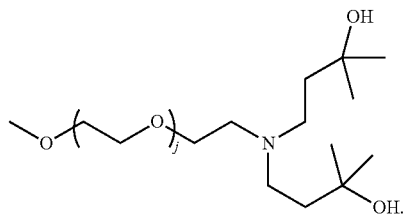

(II)

In some such embodiments, $L^{2b}$ is $C_2$-$C_6$ alkylene. In other embodiments, $L^{2b}$ is 3 to 12 or 4 to 8 membered heteroalkylene containing one or more oxygen or nitrogen atoms. In other embodiments $L^{2b}$ is an optionally substituted phenylene. In other embodiments, $L^{2b}$ is $C_2$-$C_6$ alkylene in which one methylene unit is replaced by an optionally substituted ring structure described herein (e.g., an optionally substituted phenylene). In still other embodiments, $L^{2b}$ is 3 to 12 or 4 to 8 membered heteroalkylene containing one or more oxygen or nitrogen atoms, in which a methylene unit is replaced by an optionally substituted ring structure described herein (e.g., an optionally substituted phenylene). In some such embodiments, each of R and R* is independently —$NH_2$ or —NHAc. In other such embodiments, each of $R^{5b}$ and $R^{6b}$ is —OH or a protected hydroxy. In further embodiments, at least one of $R^{5b}$ and $R^{6b}$ is —$OR^7$, and $R^7$ is

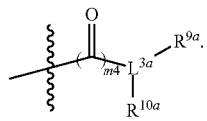

In further embodiments, each one of $R^{5b}$ and $R^{6b}$ is

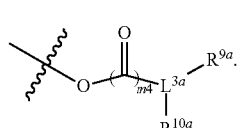

In some embodiments, m4 is 1. In other embodiments, m4 is 0. In other embodiments, at least one of $R^{5b}$ and $R^{6b}$ is —$NHR^8$, and $R^8$ is

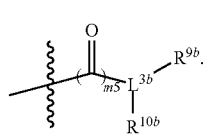

In further embodiments, each one of $R^{5b}$ and $R^{6b}$ is

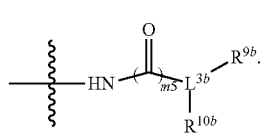

In some embodiments, m5 is 1. In other embodiments, m5 is 0. In other embodiments, at least one of one of $R^{5b}$ and $R^{6b}$ is H. In some such embodiments, each of $L^{3a}$ and $L^{3b}$ is a $C_2$-$C_6$ alkylene linker. In other embodiments, each of $L^{3a}$ and $L^{3b}$ is a 3 to 12 or 4 to 8 membered heteroalkylene linker containing one or more oxygen or nitrogen atoms. In further embodiments, at least one of $R^{9a}$, $R^{9b}$, $R^{10a}$ and $R^{10b}$ is H. In further embodiments, at least one of $R^{9a}$, $R^{9b}$, $R^{10a}$ and $R^{10b}$ is —$OR^{11}$, and $R^{11}$ is

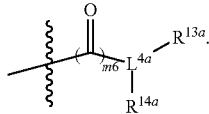

In further embodiments, each one of $R^{9a}$, $R^{9b}$, $R^{10a}$ and $R^{10b}$ is

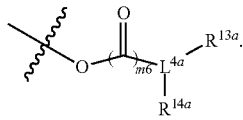

In some embodiments, m6 is 1. In other embodiments, m6 is 0. In some such embodiments, each one of $R^{13a}$ and $R^{14a}$ is —OH. In other embodiments, at least one of $R^{13a}$ and $R^{14a}$ is H. In other embodiments, at least one of $R^{9a}$, $R^{9b}$, $R^{10a}$ and $R^{10b}$ is —$NHR^{12}$, and $R^{12}$ is

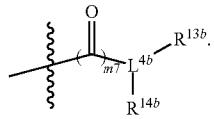

In further embodiments, each one of $R^{9a}$, $R^{9b}$, $R^{10a}$ and $R^{10b}$ is

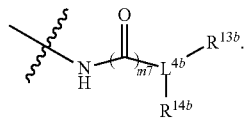

In some embodiments, m7 is 1. In other embodiments, m7 is 0. In some such embodiments, each of $R^{13b}$ and $R^{14b}$ is independently —$NH_2$ or —NHAc. In other embodiments, at least one of $R^{13b}$ and $R^{14b}$ is H. In some further embodiments, the structure of Formula (Ib-1) has the structure of Formula (Ib-2) or (Ib-3):

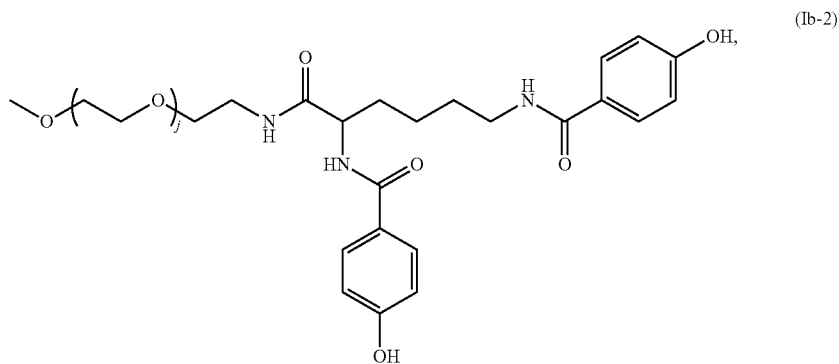

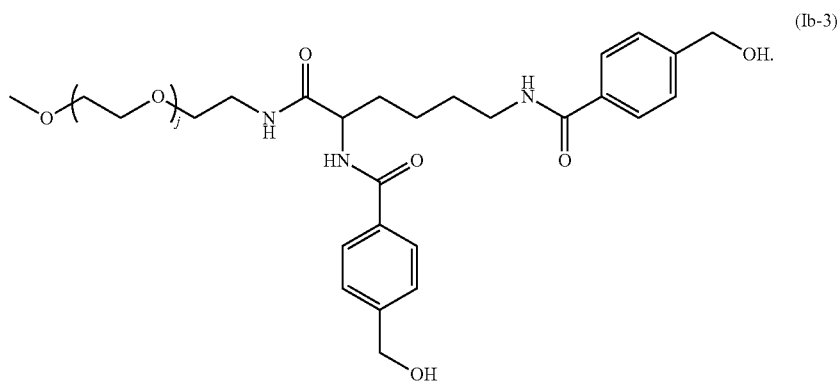

In some further embodiments, the structure of Formula (Ib-1) has the structure of Formula (Ib-4):

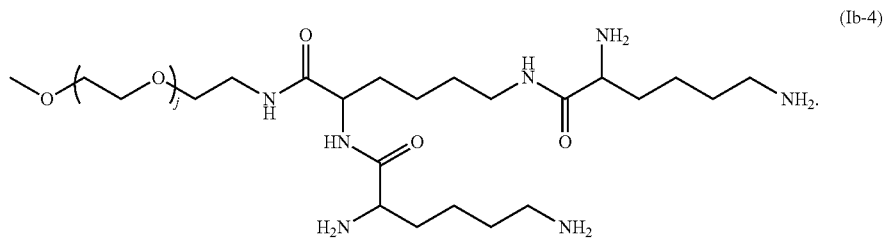

(Ib-4)

In some further embodiments, the structure of Formula (Ib-1) has the structure of Formula (Ib-5):

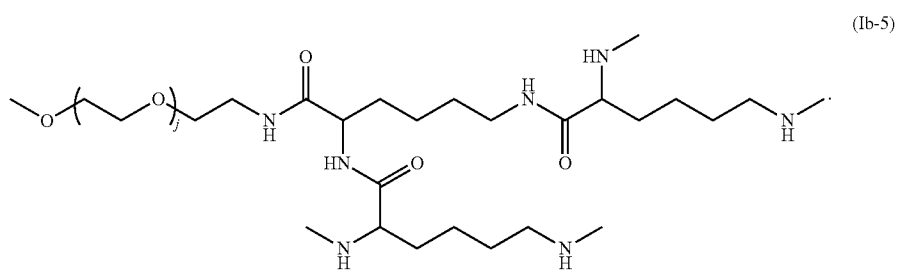

(Ib-5)

structure of Formula (Ib-1) has the structure of Formula (Ib-6):

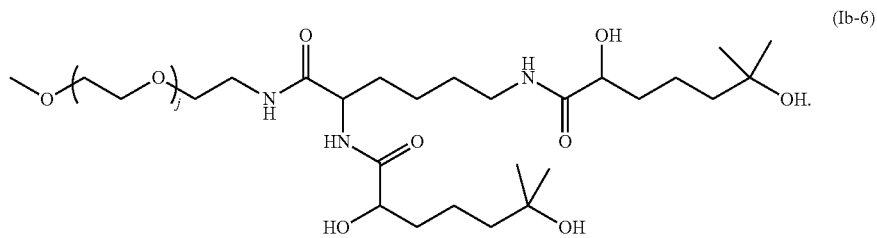

(Ib-6)

In some embodiments of the polymer of Formula (I), (I'), (Ia), (Ia'), (Ib), (Ib-1), (Ib-2), (Ib-3), (Ib-4), (Ib-5), (Ib-6), (Ic), (Ic-1), (Id), (Ie), (If), (Ig), (Ih) (Ij), (Ik), or (II) is from about 50 to about 1000, from about 200 to about 800, or from about 300 to about 600. In some embodiments j is about 15, 20, 30, 40, 50, 60, 70, 80, 90, 100, 150, 200, 250, 300, 350, 400, 450, 500, 550, 600, 650, 700, 750, 800, 850, 900, 950, 1000, 1100, 1200, 1300, 1400, 1500, or within a range defined by any of the aforementioned values. In some embodiments, the polymer of Formulas (I), (Ia), (Ia'), (Ib), (Ib-1), (Ib-2), (Ib-3), (Ib-4), (Ib-5), (Ib-6), (Ic), (Ic-1), (Id), (Ie), (If), (Ig), (Ih) (Ij), (Ik), or (II) has an average molecular weight of from about 2 kDa to about 60 kDa. For example, the polymer of Formulas (I), (Ia), (Ia'), (Ib), (Ib-1), (Ib-2), (Ib-3), (Ib-4), (Ib-5), (Ib-6), (Ic), (Ic-1), (Id), (Ie), (If), (Ig), (Ih) (Ij), (Ik), or (II) may have an average molecular weight of about 2 kDa, 5 kDa, 10 kDa, 15 kDa, 16 kDa, 17 kDa, 18, kDa, 19 kDa, 20 kDa, 21 KDa, 22 kDa, 23 kDa, 24 kDa. 25 kDa, 26 kDa, 27 kDa, 28 kDa, 29 kDa, 30 kDa, 32 kDa, 34 kDa, 36 kDa, 38 kDa, 40 kDa, 42 kDa, 44 kDa, 46 kDa, 48 kDa, 50 kDa, 52 kDa, 54 kDa, 58 kDa, or 60 kDa, or within a range defined by any of the aforementioned values. For example, the polymer of Formulas (I), (Ia), (Ia'), (Ib), (Ib-1), (Ib-2), (Ib-3), (Ib-4), (Ib-5), (Ib-6), (Ic), (Ic-1), (Id), (Ie), (If), (Ig), (Ih) (Ij), (Ik), or (II) has an average molecular weight of from about 2 to about 60 kDa, about 5 to about 50 kDa, about 5 to about 30 kDa, about 10 to about 40 kDa, about 15 to 30 kDa, or about 15 to 25 kDa.

Polymer of Formula (II)

In some embodiments of the polymer described herein, the polymer is a compound having the structure of Formula (II):

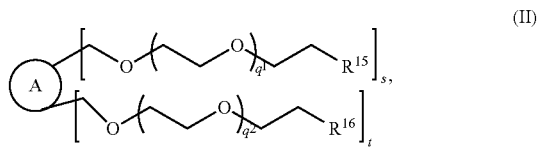

(II)

wherein: A is selected from the group consisting of a carbon atom, a $C_2$ to $C_{20}$ alkylene; a 2 to 20 membered heteroalkylene, phenylene, 5-10 membered heteroarylene, $C_{5-10}$ cycloalkylene, and 5-10 membered heterocycloalkylene; each $R^{15}$ is independently selected from the group consisting of —O—$C_1$-$C_6$ alkyl, —OC(O)($C_1$-$C_6$ alkyl), —OC(O)phenyl, —NHC(O)($C_1$-$C_6$ alkyl), —NHC(O)phenyl, —NHC(O)phenylene-acetoxymethyl

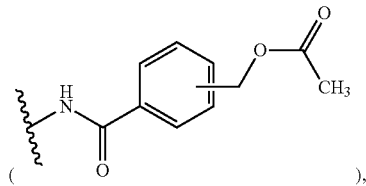

a protected hydroxy, or a protected amino; each $R^{16}$ is independently —OH or —$NH_2$; each of $q^1$ and $q^2$ is independently an integer from 10 to 500; and each of s and t is independently an integer from 1 to 4, provided that s+t is equal to or is greater than 2. In some such embodiments, A is a carbon atom. In other such embodiments, A is a phenylene. In yet other such embodiments, A is a $C_2$ to $C_{20}$ alkylene.

In some embodiments of the polymer of Formula (II), s+t is 4. In other embodiments, s+t is 8. In some embodiments, s+t is 5, 6, or 7. In some specific embodiments, s is 2 and t is 2 or one of s and t is 1, and the other s and t is 3. In other specific embodiments, s is 4 and t is 4. In yet other specific embodiments, one of s and t is 5 and the other s and t is 3. In one embodiment, s is 5 and t is 3. In another embodiment, s is 3 an t is 1. In another embodiment, s is 3 and t is 3. In yet another, s is 3 and t is 5. In additional embodiments, s is 2 and t is 4 or s is 4 and t is 2. In yet additional embodiments, s is 2 and t is 5 or s is 5 and t is 2, or s is 3 and t is 4, or s is 4 and t is 3.

In some embodiments, the polymer of Formula (II) has the structure of Formula (IIa):

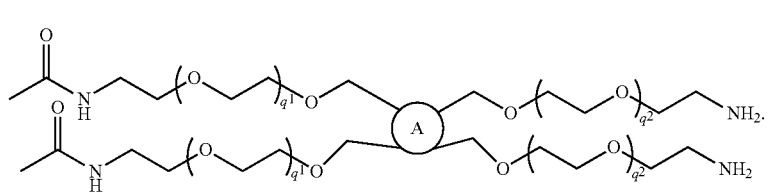

In some such embodiments, A is a carbon atom. In other such embodiments, A is a phenylene. For example, the polymer of Formula (IIa) may also be represented by Formula (IIa-1) or (IIa-2):

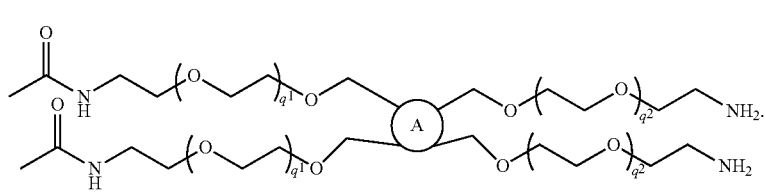

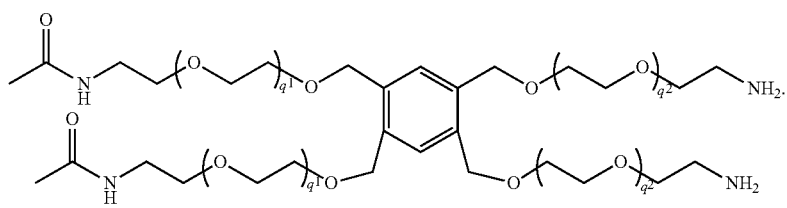

In some embodiments, the polymer of Formula (II) has the structure of Formula (IIa'):

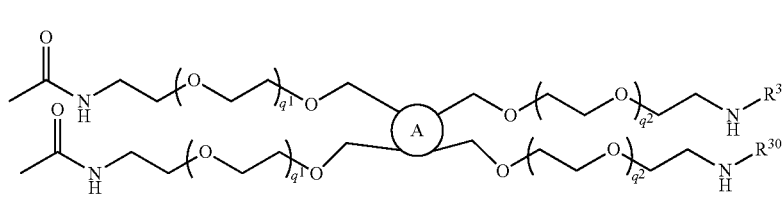

wherein each $R^{30}$ is independently optionally substituted $C_{1-6}$ alkyl. In some such embodiments, A is a carbon atom. In other such embodiments, A is a phenylene. For example, the polymer of Formula (IIa') may also be represented by Formula (IIa'-1) or (IIa'-2):

has a protected amino group that is incapable as being used as an anchor for liquid phase synthesis. Alternative embodiments to the polymer of Formula (IIb') may also include those with two, four or five free amino groups and one, two, three, or four protected amino groups (e.g., acetyl or Ac

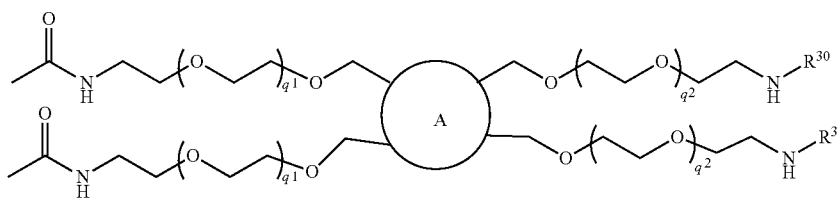

(IIa'-1)

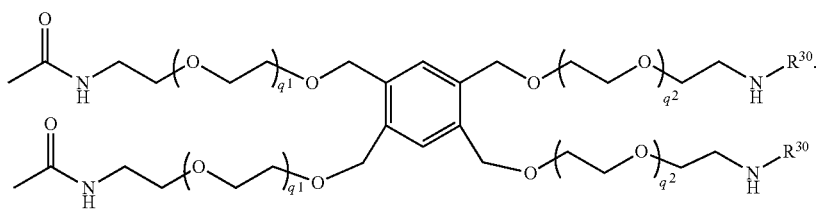

(IIa'-2)

Alternative embodiments to the polymer of Formula (IIa'), (IIa'-1) and (Ia'-2) may include those with one or three free amino group and three or one protected amino group (e.g., acetyl or Ac group). In addition to the Ac group, other common amino protecting groups such as Bz may also be used. In some other embodiments, A is a $C_2$ to $C_{20}$ alkylene and the polymer of Formula (II) has the structure of Formula (IIb'):

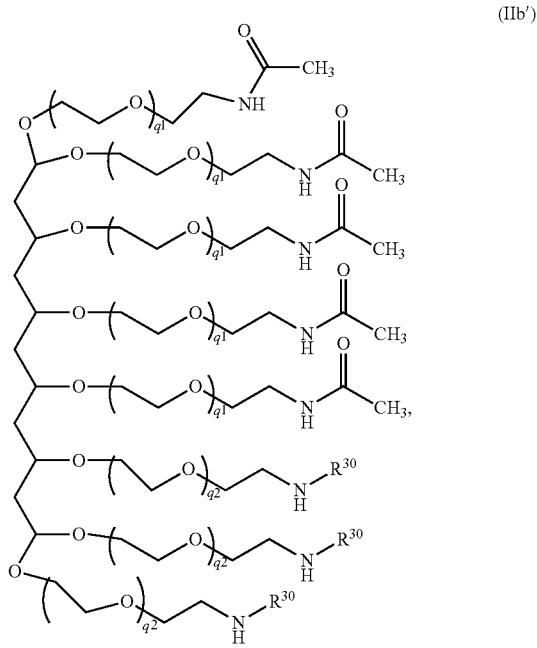

(IIb')

which has eight PEG pendant arms. Alternative embodiments to the polymer of Formula (IIb') may include those with three, four, five, six, or seven PEG pendant arms where at least one pendant PEG arm has a free amino group. In some further embodiments, at least one pendent PEG arm group). In addition to the Ac group, other common amino protecting groups such as Bz may also be used. In still other embodiment, A is a 3 to 20, 5 to 15 or 6 to 12 membered heteroalkylene containing one or more O, N, S, C(=O) or C(=S).

In some embodiments of the polymer of Formula (II), (IIa), (IIa'), (IIa-1), (IIa-2), (IIa'-1), (IIa'-2) (IIb), or (IIb'), the number of polyethylene units (PEG) $q^1$ and $q^2$ may be controlled to modulate the properties of the polymer. In some embodiments, each of $q^1$ and $q^2$ is independently an integer from 10 to 500. For example, in some embodiments, each of $q^1$ and $q^2$ may be 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500, or within a range defined by any two of the aforementioned values. For example, in some embodiments, each $q^1$ is independently from about 30 to about 150, about 40 to about 100, or about 50 to about 75. In some embodiments, each $q^2$ is independently from about 30 to about 150, about 40 to about 100, or about 50 to about 75. In some embodiments, $q^1$ and $q^2$ may have the same value. In other embodiments, $q^1$ and $q^2$ may have different values. In some embodiments, it is preferable to control the length of $q^1$ and $q^2$ such that the average molecular weight of the polymer is from about 2 kDa to about 60 kDa, from about 5 kDa to about 50 kDa, from about 10 kDa to about 50 kDa, from about 15 kDa to about 30 kDa, or about 20 kDa.

In any embodiments of the polymer described herein, when the polymer comprises two or more PEG pedant arms, at least one of the PEG pendent arms has a reactive terminal group (e.g., —NH$_2$ or —OH) that can be used as an anchor for liquid phase synthesis. In further embodiments, when the polymer contains two, three or more PEG pedant arms, at least one of the PEG pendent arms has a non-reactive terminal group (e.g., a protected amino or a protected hydroxy group) such that pendant arm cannot be used as an anchor for liquid phase synthesis.

Method of Preparing Oligonucleotide by Liquid Phase Oligonucleotide Synthesis (LPOS)

Another aspect of the present application relates to a method for making a compound by liquid phase synthesis. The compound may be an oligonucleotide, a peptide, a polynucleotide (i.e., nucleic acid), or a small molecule. In certain embodiments, the method is for making an oligonucleotide by liquid phase oligonucleotide synthesis.

In some embodiments of the method described herein, the method includes dissolving a polymer as described herein in a first solvent to form a reaction matrix, contacting, or otherwise reacting, the polymer with one or more nucleoside analogs to form a first bioconjugate comprising a structure of Formula (III):

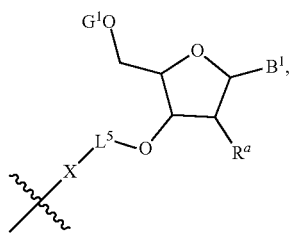
(III)

wherein $B^1$ is a nitrogenous base; $G^1$ is a 5' hydroxy blocking group; X is O or $NR^{20}$; R is —H, —OH, halogen, —O—($C_1$-$C_6$ alkyl), —O—($C_1$-$C_6$ haloalkyl), or —OY, where Y is a 2' hydroxy protecting group; and $L^5$ is a cleavable heteroalkylene linker where one or more carbon atoms is replaced by O, S, N, C(=O) or C(=S). In some such embodiments, the nitrogenous base comprises a purine base, a deazapurine base, or a pyrimidine base. In some embodiments, the structure of Formula (III) is also represented by Formula (IIIa) or (IIIb):

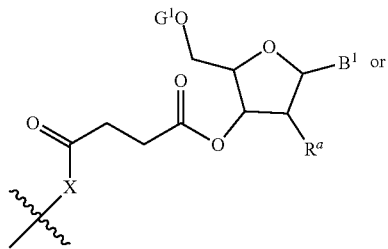
(IIIa)

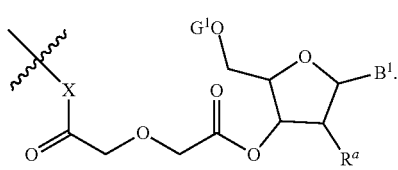
(IIIb)

In some embodiments, X is O. In other embodiments, X is $NR^{20}$, and $R^{20}$ is H. In some embodiments, the amide bond —$NR^{20}$—C(=O)— may be formed from the terminal amino group of the polymer reacting with a first nucleoside analog containing a 3' succinate (which contains a free carboxy group). In other embodiments, the amide bond —$NR^{20}$—C(=O)— may be formed from a linker bound to the 3' position of the first nucleoside analog. Other alternative linker may include hydroquinone-O,O'-diacetic acid (HQDA or Q-linker).

In some embodiments of the method described herein, $B^1$ is independently optionally protected adenine, optionally protected deaza adenine, optionally protected cytosine, optionally protected guanine, optionally protected deaza guanine, optionally protected thymine or optionally protected uracil. In some embodiments, $B^1$ is

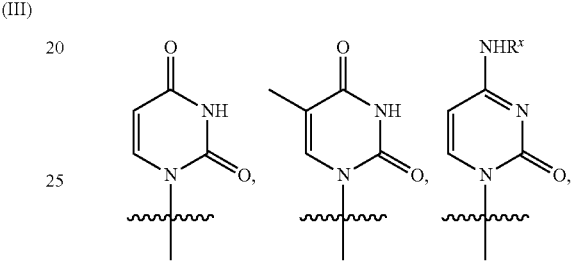

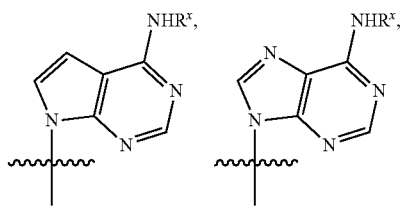

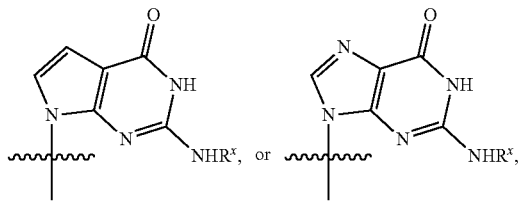

wherein $R^x$ is hydrogen, unsubstituted or substituted $C_1$-$C_6$ alkyl, or an amino protecting group, or the hydrogen in —$NHR^x$ is absent and $R^x$ is a divalent amino protecting group. In some embodiments, $G^1$ is a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl. In some embodiments, $G^1$ is bis(4-methoxyphenyl)phenylmethyl (DMT).

In some embodiments, the polymer has an average molecular weight from about 2 kDa to about 1000 kDa, from about 5 kDa to about 1000 kDa, or from about 10 kDa to about 1000 kDa, or from about 20 kDa to about 500 kDa, or from about 30 kDa to about 100 kDa, or from about 15 kDa to about 30 kDa. In some embodiments, the polymer has the average molecular weight from about 10 kDa to about 100 kDa. Without being bound by any particular theory, the polymer having an average molecular weight of about 20 KDa may provide an optimal balance of reaction yield and product purity.

In some embodiments of the method described herein, the method further comprises: removing the 5' hydroxy blocking group ($G^1$) to form a 5' unblocked first bioconjugate; and isolating the 5' unblocked first bioconjugate. In some such embodiments, isolation of the 5' unblocked first bioconjugate is achieved by precipitation, dialysis or filtration.

In some embodiments, the isolation is achieved by precipitation. In some embodiments, the precipitation of the 5' unblocked first bioconjugate is done by adding the solution comprising the bioconjugate to a solvent comprising pentane, hexane, heptane, dialkyl ethers (e.g., diethyl ether, t-butyl methyl ether, etc.), toluene, isopropyl acetate, dichloromethane, dimethyl sulfoxide, ethyl acetate, alkanols (e.g., methanol, ethanol, isopropanol), or alkenols, or a combination thereof. In some such embodiments, the solvent is diethyl ether. In other such embodiments, the solvent is isopropanol. In other embodiments, the isolation is achieved by a filtration step. The filtration step may include dialysis, filtration, nanofiltration, ultrafiltration, or any known filtration technology suitable for use herein, and combinations thereof. In some embodiments, the filtration step comprises dialysis or filtration. In further embodiments, filtration step includes the use of a membrane. The membrane may comprise a cellulose acetate, a glass fiber, a carbon-based polymer, a regenerated cellulose and combinations thereof. In certain embodiments, the regenerated cellulose has an electrostatic charge. In some embodiments, the regenerated cellulose membrane is negatively charged. In some embodiments, the regenerated cellulose comprises the structure:

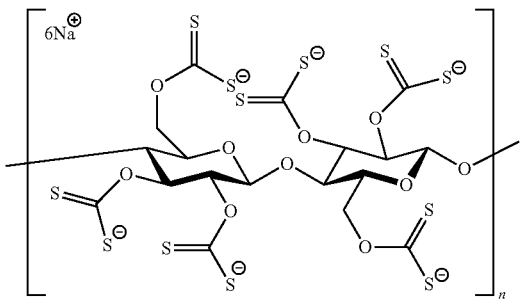

In some embodiments, the regenerated cellulose has a molecular weight cutoff (MWCO) from about 5 kDa to about 50 kDa, from about 6 kDa to about 40 kDa, about 7 kDa to about 30 kDa, or about 8 kDa to about 12 kDa. The regenerated cellulose membrane is capable of retaining the PVH containing bioconjugate as an alternative to the expensive nanofiltration membranes prepared with polyimide. The negatively charged membrane capable of reducing non-specific adsorption of negatively charged biomolecules. In some embodiments, the regenerated cellulose is treated in a process including carbon disulfide followed by an aqueous metal hydroxide. In some embodiments, the regenerated cellulose comprises dithiolate groups and metal cations. In some embodiments, the metal cations comprise group 1 metals (i.e., group IA metals or alkali metals), group 2 metals (i.e., group IIA metals or alkaline earth metals) and combinations thereof. In some embodiments, the metal cations comprise sodium cations.

In some embodiments of the method described herein, the method further comprises: (a) reacting the 5' unblocked first bioconjugate with one or more nucleoside phosphoramidite analogs in a second solvent to form a second bioconjugate comprising the structure of Formula (IV):

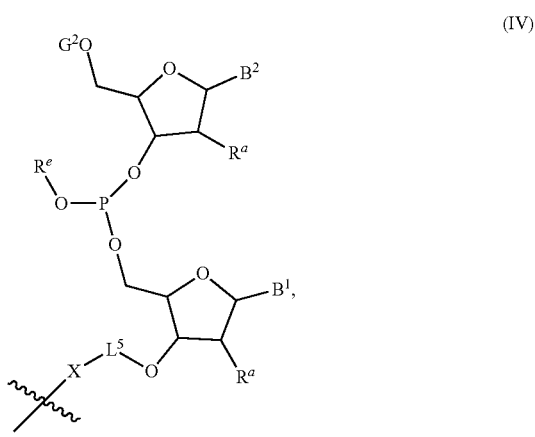

wherein $G^2$ is a 5' hydroxy blocking group; $B^2$ is a nitrogenous base; and R is a phosphite protecting group;

(b) oxidizing the phosphite moiety in Formula (IV);

(c) removing the 5' blocking group $G^2$ to form a 5' unblocked second bioconjugate comprising the structure of Formula (IV'):

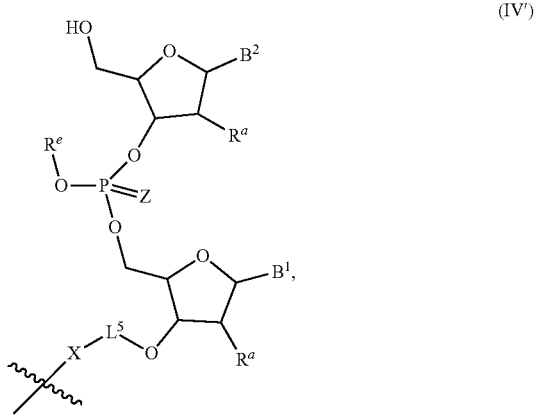

wherein Z is O or S; and (d) isolating the 5' unblocked second bioconjugate. In some such embodiments, the structure of Formula (IV) is also represented by (IVa) and the Formula (IV') is also represented by Formula (IV'a):

(IVa)

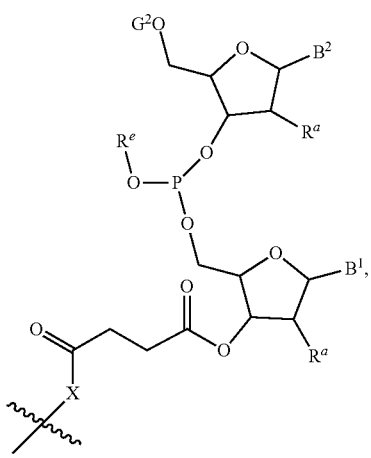

(IV'a)

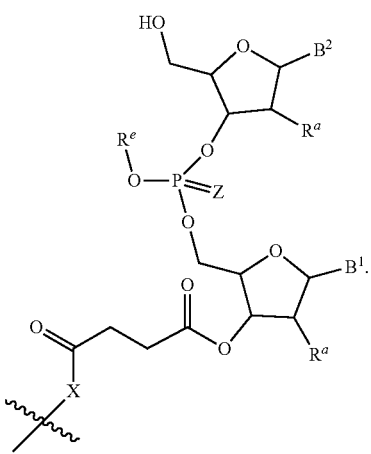

In some such embodiments, $R^e$ is unsubstituted $C_1$-$C_6$ alkyl or substituted $C_1$-$C_6$ alkyl. A nonlimiting example of a substituted $C_1$-$C_6$ alkyl suitable for use as R includes —$CH_2CH_2CN$. In some embodiments, the method further comprises blocking unreacted 5' hydroxy group in the 5' unblocked first bioconjugate prior to step (b). In some such embodiments, X is $NR^{20}$, and $R^{20}$ is H.

In some embodiments of the method described herein, $B^2$ is independently optionally protected adenine, optionally protected deaza adenine, optionally protected cytosine, optionally protected guanine, optionally protected deaza guanine, optionally protected thymine, or optionally protected uracil. In some embodiments, $B^2$ is

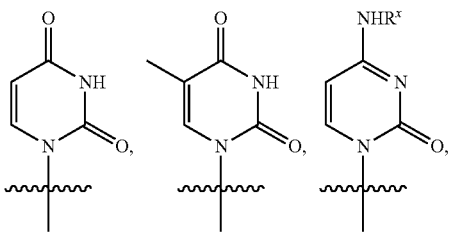

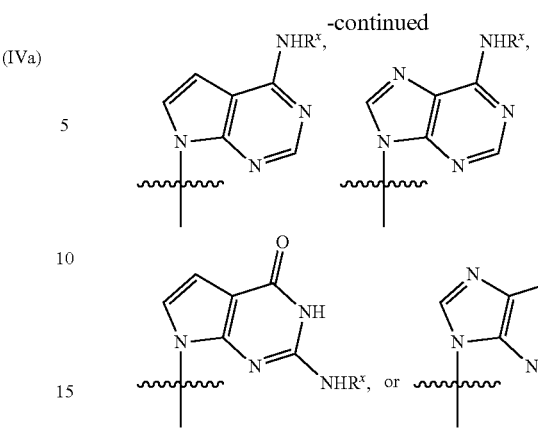

wherein $R^x$ is hydrogen, unsubstituted or substituted $C_1$-$C_6$ alkyl, or an amino protecting group, or the hydrogen in —$NHR^x$ is absent and $R^x$ is a divalent amino protecting group. In some embodiments of the method described herein, $G^2$ is a trityl type of hydroxy protecting group selected from the group consisting of (4-methoxyphenyl) diphenylmethyl, bis(4-methoxyphenyl)phenylmethyl, tris (4-methoxyphenyl)methyl, 9-phenylxanthen-9-yl, and 9-(4-methoxyphenyl)xanthen-9-yl. In some embodiments, $G^2$ is bis(4-methoxyphenyl)phenylmethyl (DMT).

In some embodiments of the method described herein, the method further comprises blocking unreacted 5' hydroxy group in the 5' unblocked first bioconjugate prior to step (b). In some such embodiment, said blocking is performed by reacting the 5' hydroxy group with acetic anhydride ($Ac_2O$).

In some embodiments of the method described herein, isolation or purification of the 5' unblocked second bioconjugate is achieved by precipitation, filtration, or dialysis. In some embodiments, the isolation is achieved by precipitation. In some embodiments, the precipitation of the 5' unblocked second bioconjugate is done by adding the solution comprising the bioconjugate to a solvent comprising pentane, hexane, heptane, diethyl ether, t-butyl methyl ether, toluene, isopropyl acetate, dichloromethane, dimethyl sulfoxide, ethyl acetate, methanol, ethanol, isopropanol, or a combination thereof. In some such embodiments, the solvent is diethyl ether. In other such embodiments, the solvent is isopropanol. In other embodiments, the isolation/purification uses a regenerated cellulose membrane having a molecular weight cutoff (MWCO) from about 5 kDa to about 50 kDa, from about 6 kDa to about 40 kDa, about 7 kDa to about 30 kDa, or about 8 kDa to about 12 kDa. In some further embodiments, steps (a)-(d) are repeated multiple cycles until a desired length of oligonucleotide has been synthesized.

In some embodiments of the method described herein, steps (a)-(d) are repeated multiple cycles until one or more desired length of oligonucleotides have been synthesized. In some such embodiments, steps (a)-(d) are repeated at least about 2, 3, 4, 5, 6, 7, 8, 9, 10, 11, 12, 13, 14, 15, 16, 17, 18, 19 or 20 cycles. In some such embodiments, the oligonucleotide synthesized may comprises at least 2, 3, 4, 5, 6, 7, 8, 9, 10, 11, 12, 13, 14, 15, 16, 17, 18, 19 or 20 bases.

In some embodiments, the loading capacity of the polymers described herein is about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 μmol nucleotide per gram of polymer, or within a range defined by any two of the aforementioned loading capacities.

In some embodiments of the method described herein, the method further comprises removing the oligonucleotides from the polymer. In some such embodiments, the removing step includes a step of covalent chemical bond scission. In some embodiments, the removing step includes hydrolysis. In certain embodiments, the removing includes hydrolysis at a temperature from about 0° C. to about 80° C., or about 10° C. to about 60° C., or about 15° C. to about 30° C. In further embodiments, when the first nucleoside is covalently attached to the polymer through reaction of the 3'-succinic acid reacting with the amino group of the polymer, the amide bond formed between the first nucleoside and the polymer may be cleaved by hydrolysis.

In some embodiments of the method described herein, each of the first solvent and the second solvent comprise one or more non-protic polar solvents, or combinations thereof. In some embodiments, the one or more non-protic polar solvents comprise acetonitrile, tetrahydrofuran (THF), dimethylformamide (DMF), dimethyl sulfoxide (DMSO), dichloromethane (DCM), sulfolane, or combinations thereof. In one embodiment, the first solvent and/or the second solvent comprises acetonitrile. In another embodiment, the first solvent and/or the second solvent comprises a mixture of acetonitrile and sulfolane.

Additional embodiments of the present application relate to an oligonucleotide prepared by any of the methods described herein.

EXAMPLES

Some aspects of the embodiments discussed above are disclosed in further detail in the following examples, which are not in any way intended to limit the scope of the present disclosure. Those in the art will appreciate that many other embodiments also fall within the scope of the compositions, kits and methods of the present application, as is described herein above and in the claims.

General Procedure for DMT Loading Measurement

An UV/Vis spectrophotometric method is used to determine the DMT loading (μmol/g) of a 5'-DMT protected nucleotide conjugated on a Polyvalent Hub (PVH). The sample is dissolved in acetonitrile (AcN) containing toluenesulfonic acid (TSA). The acid cleaves off the DMT protective group and its loading is quantitatively determined. Agilent 8453 UV-Visible spectrophotometer, Agilent UV-Visible ChemStation software Rev. A.10.0, and Agilent UV-Visible rectangular cell 10 mm, 3.5 mL (P/N 5061-3387) are used for the measurement.

- A master batch of TSA solution in AcN is prepared by dissolving 8.0 g of TSA in 500 mL of HPLC grade AcN. The resulting solution is stable under ambient temperature for 4 weeks.
- Launch the Agilent UV-Visible ChemStation software and select Fixed Wavelength(s) of 498 nm.
- Acquire a blank spectrum using the TSA/AcN solution.
- Accurately weigh out 20.0-26.0 mg of the nucleotide-conjugated polymer sample and transfer it into 100 mL of TSA/AcN solution.
- Vortex for 2 minutes and allow any insoluble materials settle to the bottom in 10-15 minutes.
- Transfer the supernatant to a dry cuvette (Agilent UV-Visible rectangular cell 10 mm, 3.5 mL).
- Scan the sample solution and take the absorbance value at 498 nm.

DMT loading on the CPG support is determined using the following equation:

$$\text{Loading (μ mole/gram)} = \frac{\text{Absorbance (498 nm)} \times \text{Sample Volume (mL)}}{76.5 \, (\text{mL} * \text{cm}^{-1} * \mu \, \text{mole}^{-1}) \times \text{Sample Weight (g)}}$$

Use the 5-digit number from the 498 nm Absorbance value.

Sample Volume is 100 mL.

The extinction coefficient E for DMT is estimated 76.5 mL/cm*μmole.

Convert sample weight from mg to gram.

Example 1. General Procedure for the Synthesis of Polymer (1a)

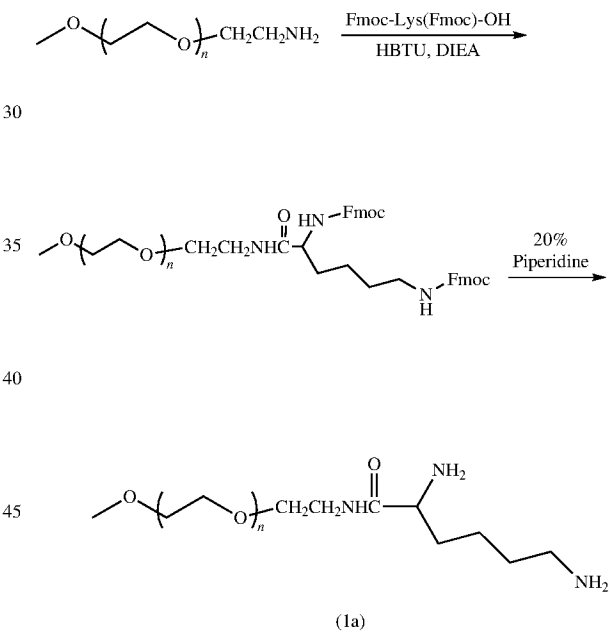

(1a)

An aliquot of 2 g commercially available of MeO-PEG-amine (MW=20 kDa, Nanosoft Polymer Inc.), 178 mg Fmoc-Lys(Fmoc)-OH (AAPPTec), 126 mg (2-(1H-benzotriazol-1-yl)-1,1,3,3-tetramethyluronium hexafluorophosphate (HBTU) (AK Scientific) and 56 mg diisopropylethylamine (TCI Chemicals) were dissolved in 10 mL dry acetonitrile (Sigma Aldrich). The reaction mixture was stirred for 2 h. The mixture was then added into stirring diethyl ether to precipitate Fmoc-Lys(Fmoc)-OH modified PEG. To the dry precipitate was added 20 mL 20% piperidine in dimethylformamide (DMF) and stirred for 1 hour to remove the Fmoc group, resulting in polymer (1a) that was isolated by precipitation in diethyl ether to give 1.88 g of polymer (1a) (Yield: 93.5%).

Example 2. Synthesis of Polymer (1a)-DMT-dT-3'-Succinate Conjugate

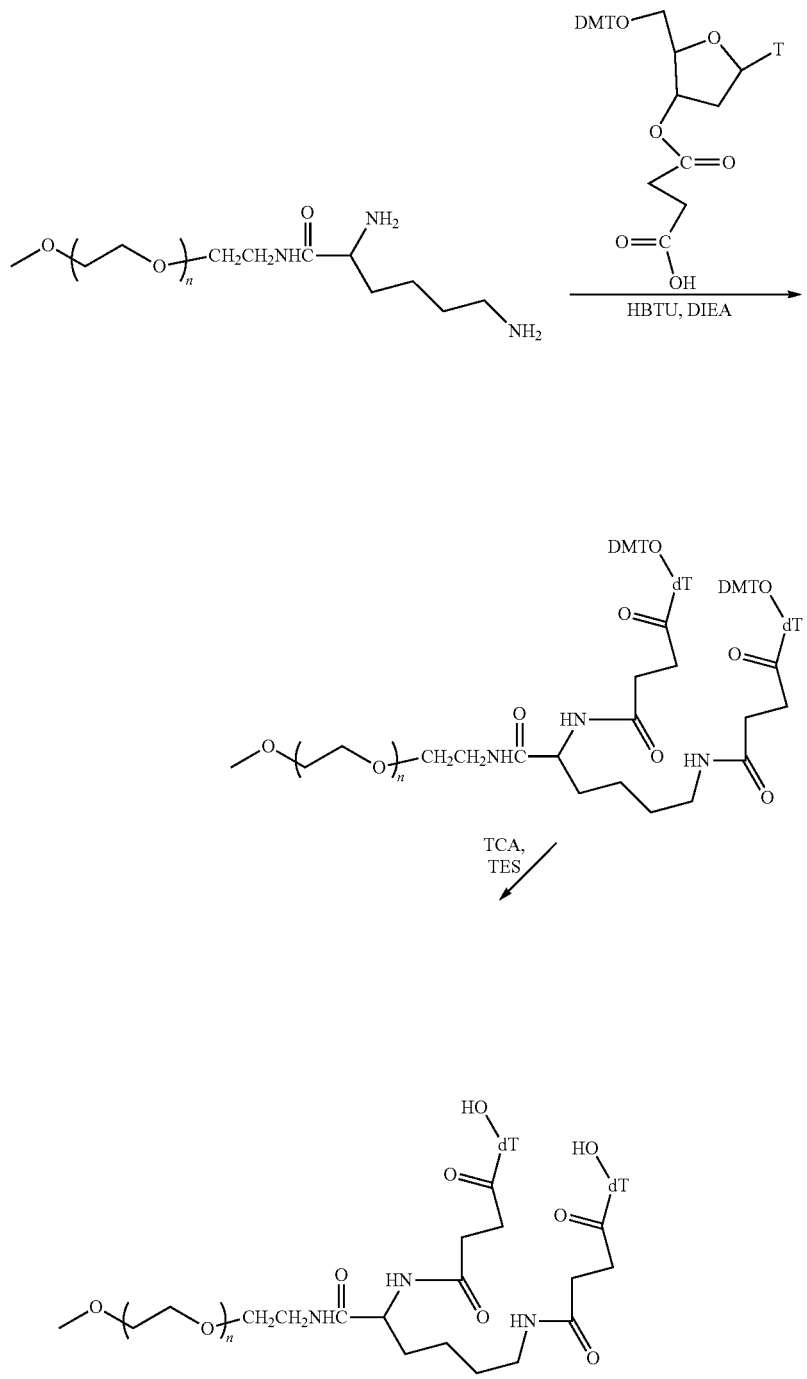

Polymer (1a) (1.88 g) was dissolved in 6 mL dry acetonitrile. Separately, 298 mg DMT-dT-3'-succinate TEA salt (Hongene Biotech), 168 mg HBTU and 74.2 mg diisopropylethylamine were dissolved in 5 mL of dry acetonitrile, and the resulting solution was allowed to stand at room temperature for 15 minutes. The polymer solution and the DMT-dT-3'-succinate solution were combined and stirred overnight at room temperature. The mixture was precipitated by diethyl ether to give the first dT conjugate with DMT. To the dry precipitate was added 1.356 mL trichloroacetic acid (TCA) (600 mg/mL in DCM) and 324 mg triethylsilane (TES) while stirring. After approximately 10 minutes, the reaction mixture precipitated by diethyl ether to give polymer (1a)-dT conjugate 2.04 g (Yield: 96%).

Example 3. Synthesis of Polymer (2)-DMT-dT-3'-Succinate Conjugate

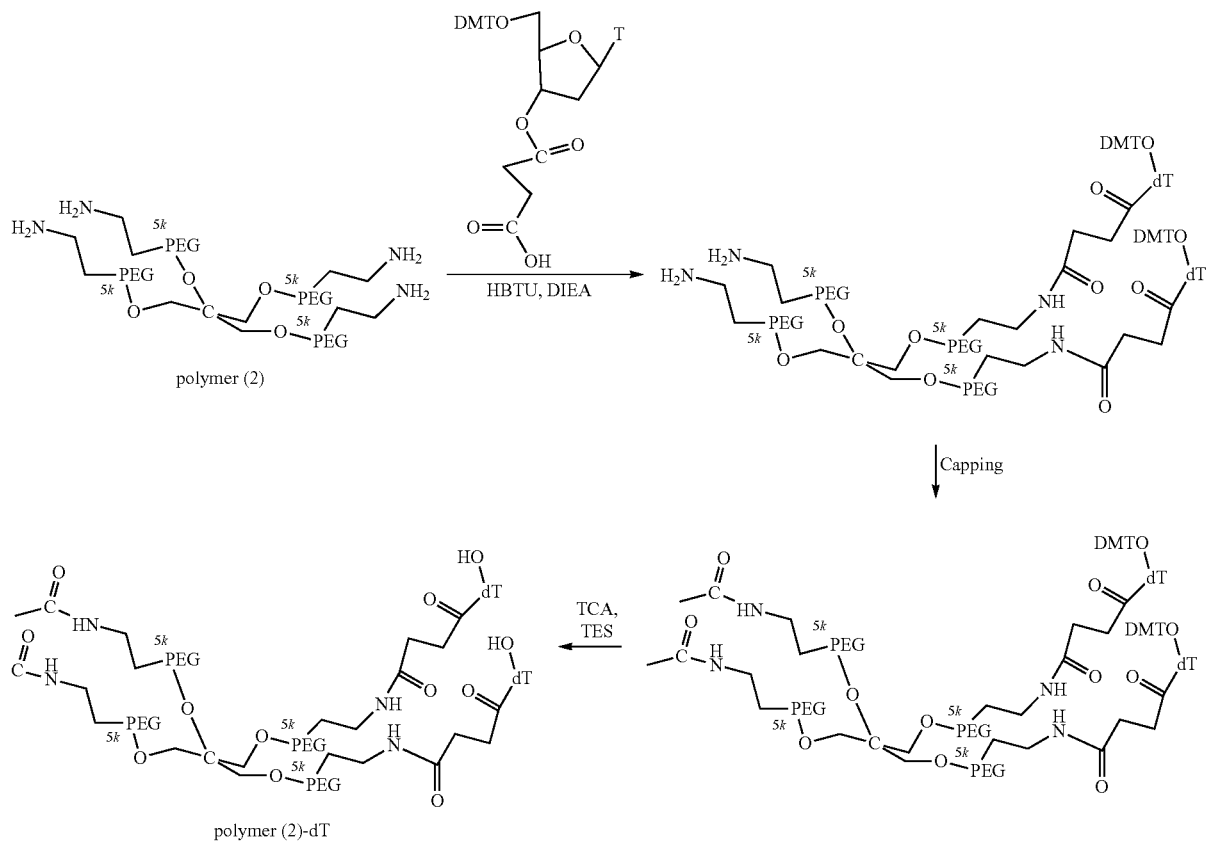

Commercially available 4-pendant PEG (2 g) where each pendant arm has an average molecular weight of about 5 kDa was dissolved in 6 mL anhydrous acetonitrile. In a separate vessel, 149 mg DMT-dT-3'-succinate TEA salt, 168 mg HBTU and 74.2 mg diisopropylethylamine in 5 mL of anhydrous acetonitrile were combined, mixed, and allowed to stand for 15 mins. The solution of 4-pendant PEG and the solution of DMT-dT-3'-succinate were then combined and stirred overnight at room temperature. The mixture was poured into diethyl ether with stirring to precipitate the first dT conjugate with DMT. The dry precipitate was added into 5 mL of nucleotides capping solution (1:1 ratio of Capping reagents A, Sigma Aldrich and 1-methylimidazole/tetrahydrofuran, applied biosystem) and the mixture was stirred for 1 hour. The reaction mixture was poured into diethyl ether with stirring to precipitate polymer (2)-dT conjugate with 5' DMT. To the above-mentioned precipitate was added 1.356 mL Trichloroacetic acid (TCA)(600 mg/mL in DCM) and 324 mg triethyl silane (TES) with constant stirring for 10 minutes. The reaction mixture was poured into stirring diethyl ether to precipitate 2.03 g (98.5% yield) polymer (2)-dT conjugate after drying under reduced pressure.

Example 4. Direct Conjugation of Eight DMT-dT-3'-Succinate Units onto Polymer (1a)

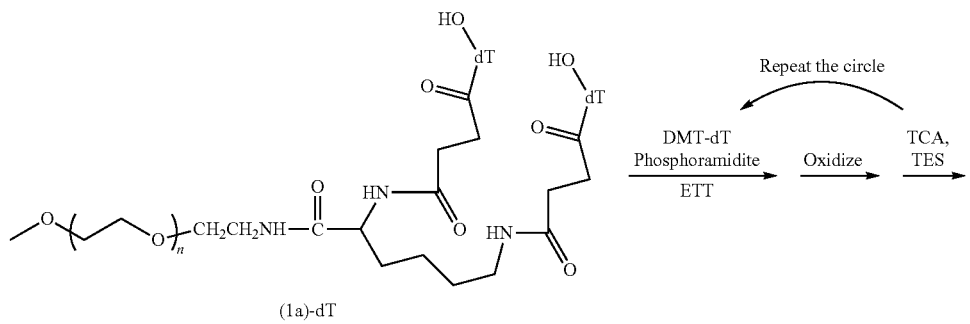

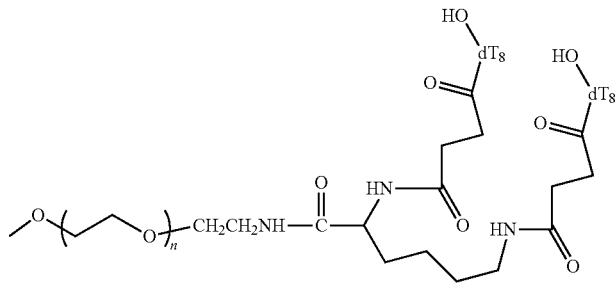

1.02 g polymer (1a)-dT conjugate, wherein polymer (1a) had an average molecular weight of approximately 20 KDa was dissolved in a mixture of ETT activator (5-(Ethylthio)-1H-tetrazole, 250 mM in 4.76 mL of anhydrous acetonitrile, Sigma Aldrich), and 248 mg DMT-dT phosphoramidite (Hongene Biotech) in a 100 mL round bottom flask. After 60 minutes of constant magnetic stirring, 158 mg m-CPBA (3-Chloroperbenzoic acid, Sigma Aldrich) was added as a powder. After 10 minutes of constant stirring, 2.04 mL of trichloroacetic acid (TCA, 600 mg/mL in DCM) and 0.706 mL TES were added. After 10 minutes of constant stirring, the reaction mixture was poured into isopropanol with stirring. The precipitate was washed by diethyl ether for 2 times to give 1.024 g polymer (1a)-2dT (Yield: 97.4%). The above-mentioned procedure was repeated six additional times, to give polymer (1a)-8dT exhibited 82.9% full product purity (FLP) after nucleotides cleavage (Yield: 77.2%). HPLC results are provided in FIG. 1 and showed relative amounts of oligonucleotide after cleavage from polymer support.

Example 5. Direct Conjugation of Eight DMT-dT-3'-Succinate Units onto Polymer (2)

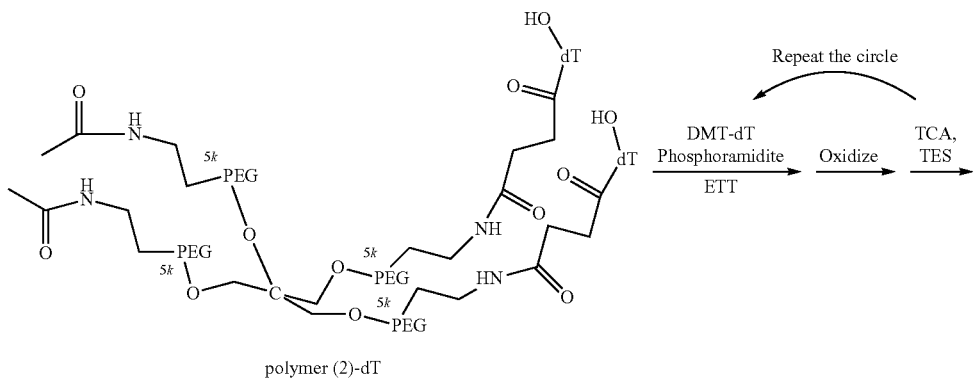

polymer (2)-dT

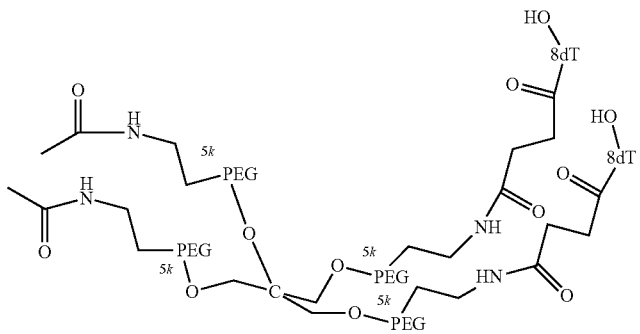

Figure 2:
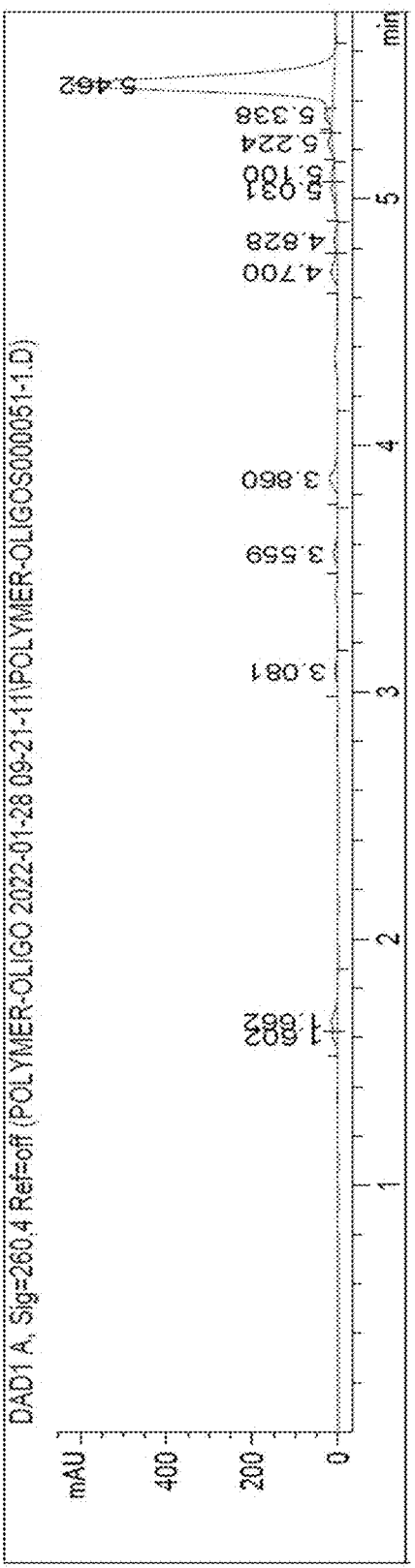
FIG. 2 is an HPLC profile of an eight dT oligonucleotide using polymer (2) by the liquid phase method disclosed herein according to an embodiment of the present application.

2.03 g polymer (2)-dT conjugate was dissolved into ETT activator (250 mM in 9.52 mL of anhydrous acetonitrile) and 496 mg DMT-dT phosphoramidite was added in a 100 mL round bottom flask with magnetic stirrer bar. After 60 minutes of constant magnetic stirring, 317 mg mCPBA was added as a powder. After 10 minutes of constant magnetic stirring, 4.08 mL of TCA (600 mg/mL in DCM) and 1.417 mL TES were added. After 10 minutes of constant magnetic stirring, the reaction mixture was poured into isopropanol with stirring. The precipitate was washed by diethyl ether for 2 times to give 1.93 g polymer (2)-2dT (Yield: 90.8%). The above procedure was repeated six additional times to give polymer (2)-8dT in 81.6% FLP after nucleotides cleavage (Yield: 82.9%). HPLC results are provided in FIG. 2 and showed relative amounts of oligonucleotide after cleavage from polymer support.

Example 6. Full Product Purity (% FLP) of Mononucleotides and Oligonucleotides The full length product purity (FLP) of dT's after cleavage from the polymer support can be found in Table 1. As can be seen, both Polymer (1a) and (2) show efficient nucleotides synthesis efficiency with high FLP >80% as long as eight nucleotides length. However, as small impurities may be trapped during the precipitation, the FLP cannot be used to precisely calculate the coupling efficiency especially with long dT's sequence synthesized.

TABLE 1

Full length product purity (% FLP) of mononucleotides and oligonucleotides after cleavage from polymer support

| Polymer structure | One dT | Two dT's | Three dT's | Four dT's | Five dT's | Six dT's | Seven dT's | Eight dT's |
|---|---|---|---|---|---|---|---|---|
| 1a | 98.7% | 95.7% | 92.4% | 89.7% | 84.1% | 83.5% | 82.3% | 82.9% |
| 2 | — | 90.1% | — | 84.6% | 85.0% | 81.2% | 83.7% | 81.6% |

Example 7. Direct Conjugation of Eight DMT-dN-3'-Succinate Units onto Polymer (1a)

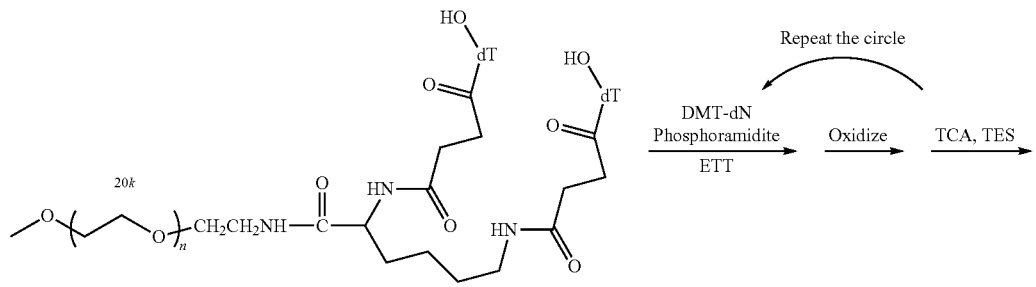

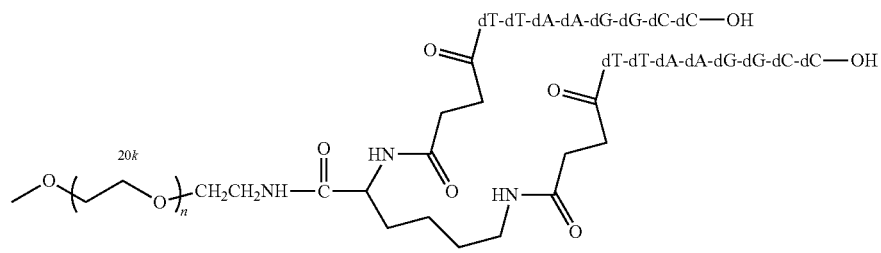

Figure 3:
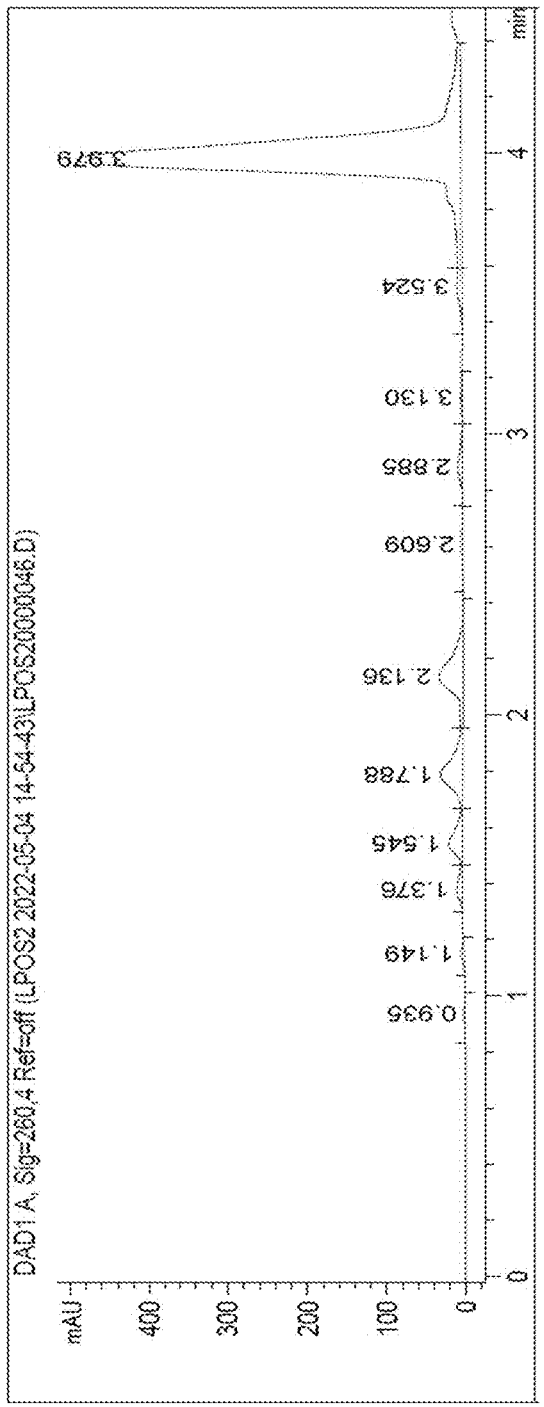
FIG. 3 is an HPLC profile of a dT-dT-dA-dA-dG-dG-dC-dC oligonucleotide synthesized with polymer (1a) having an average molecular weight of about 20 kDa by the liquid phase method disclosed herein according to an embodiment of the present application.

Polymer (1a)-dT conjugate (0.85 g) having an average molecular weight of approximately 20 kDa was dissolved in a mixture of ETT activator (5-(ethylthio)-1H-tetrazole in anhydrous acetonitrile), and DMT-dT phosphoramidite (Hongene Biotech) in a manner analogous to that described in Example 4 to give polymer (1a)-2dT. This procedure was repeated six additional times with other nucleotides to prepare the sequence polymer (1a)-dT-dT-dA-dA-dG-dG-dC-dC-OH, which exhibited 82% full product purity (FLP) after nucleotides cleavage (Yield: 88.9%). HPLC results are provided in FIG. 3 and showed relative amounts of oligonucleotide after cleavage from polymer support.

Example 8. Direct Conjugation of Eight DMT-dT-3'-Succinate Units onto Polymer (1b)

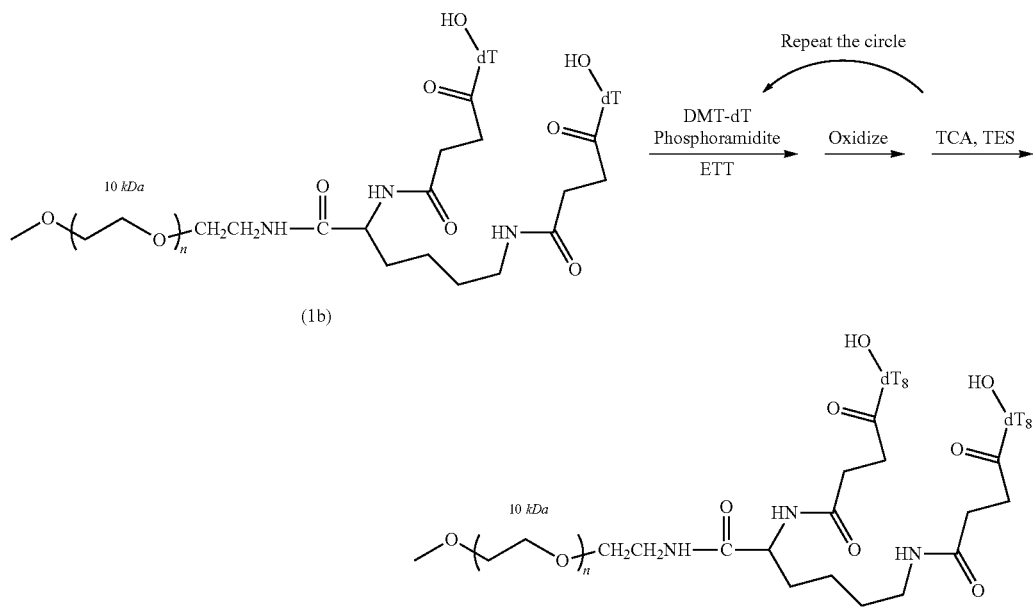

Figure 4:
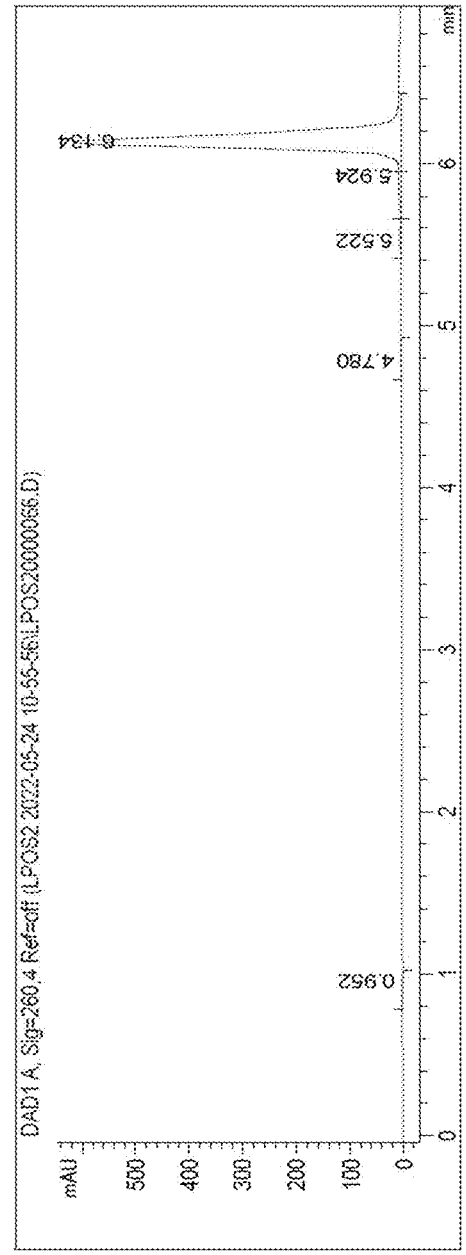
FIG. 4 is an HPLC profile of an eight dT oligonucleotide conjugate synthesized with polymer (1b) having an average molecular weight of 10 kDa by the liquid phase method disclosed herein according to an embodiment of the present application.

Polymer (1b)-dT conjugate having an average molecular weight of approximately 10 kDa was dissolved in a mixture of ETT activator (5-(ethylthio)-1H-tetrazole, 250 mM in 4.76 mL of anhydrous acetonitrile, Sigma Aldrich), and 248 mg DMT-dT phosphoramidite (Hongene Biotech) in a 100 mL round bottom flask. After 60 minutes of constant magnetic stirring, 158 mg m-CPBA (3-Chloroperbenzoic acid, Sigma Aldrich) was added as a powder. After 10 minutes of constant stirring, 2.04 mL of trichloroacetic acid (TCA, 600 mg/mL in DCM) and 0.706 mL TES were added. After 10 minutes of constant stirring, the reaction mixture was poured into isopropanol with stirring. The precipitate was washed by diethyl ether for 2 times to give 1.024 g polymer (1b)-2dT. The above-mentioned procedure was repeated six additional times, to give polymer (1b)-8dT exhibited 98.3% full length product purity after nucleotides cleavage (Yield: 92.8%). HPLC results are provided in FIG. 4 and showed relative amounts of oligonucleotide after cleavage from polymer support.

Example 9. Direct Conjugation of DMT-Nucleotide-3'-Succinate Units onto Polymer (1c)

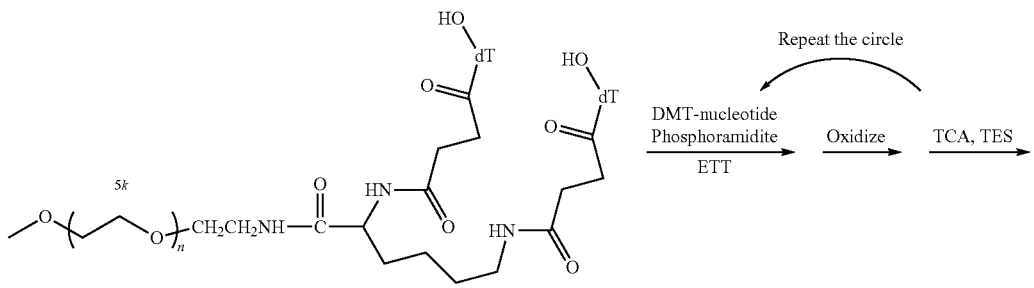

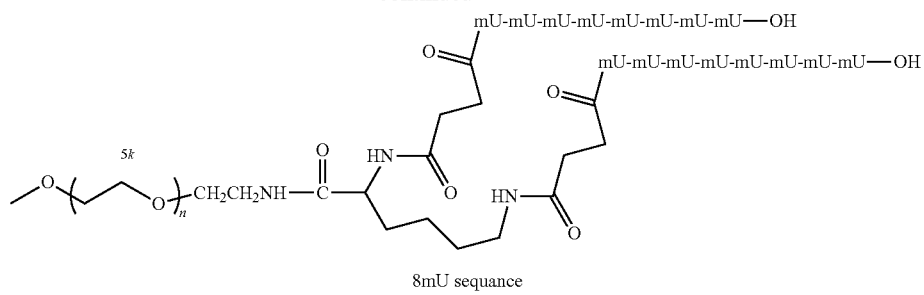

8mU sequance

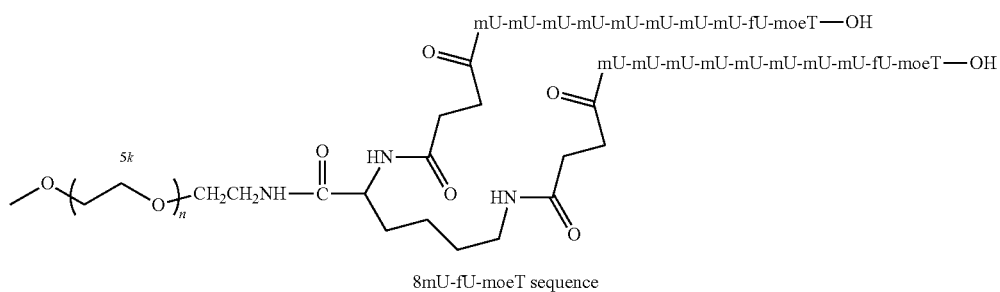

8mU-fU-moeT sequence

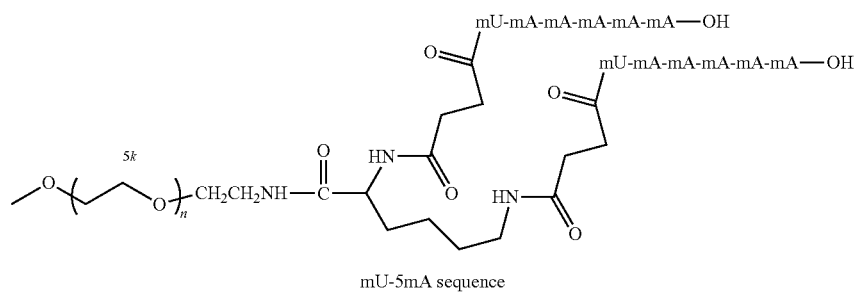

mU-5mA sequence

Polymer (1c)-dU conjugate having an average molecular weight of approximately 5 kDa was dissolved in a mixture of ETT activator (5-(ethylthio)-1H-tetrazole in anhydrous acetonitrile), and DMT-mU (i.e., DNT-2'-OMe-U) or DMT-mA (i.e., DMT-2'-OMe-A) phosphoramidite (Hongene Biotech) in a manner analogous to that described in Example 4 to give polymer (1c)-2mU or polymer (1c)-2mUmA This procedure was repeated as necessary with other nucleotides (e.g., 2'-OMe-U (mU), 2'-fluoro-U) (fU), 2'-OCH$_2$CH$_2$OCH$_3$-T (moeT) to prepare the sequences polymer (1c)-mU-mU-mU-mU-mU-mU-mU-mU, which exhibited 93.6% full product purity (FLP) after nucleotide cleavage; sequences polymer (1c)-mU-mU-mU-mU-mU-mU-mU-mU-fU-moeT, which exhibited 90.4% full length product (FLP) purity after nucleotide cleavage; and sequences polymer (1c)-mU-mA-mA-mA-mA-mA, which exhibited 92.8% full length product purity after nucleotides cleavage.

Example 10. General Procedure for the Synthesis of Polymer (3a)

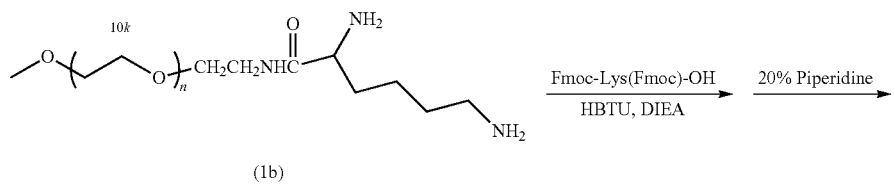

(1b)

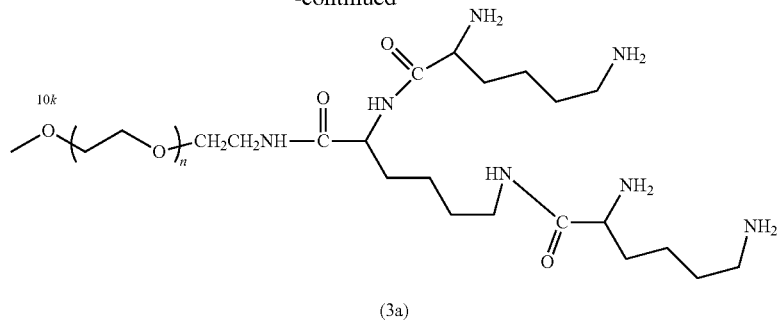

(3a)

An aliquot of polymer (1b), Fmoc-Lys(Fmoc)-OH, (2-(1H-benzotriazol-1-yl)-1,1,3,3-tetramethyluronium hexafluorophosphate (HBTU), and diisopropylethylamine were dissolved in dry acetonitrile. The reaction mixture was stirred for 2 h. The mixture was then added into stirring diethyl ether to precipitate the intermediate Lys-modified product. To the dry precipitate was added 20 mL 20% piperidine in dimethylformamide (DMF) and stirred for 1 hour to remove the Fmoc group, resulting in polymer (3a) that was isolated by precipitation in diethyl ether. Polymer (3b) was prepared following similar procedure from polymer (1c) having a molecular weight of approximately 5 kDa PEG.

Example 11. Direct Conjugation of DMT-Nucleotide-3'-Succinate Units onto Polymer (3a)

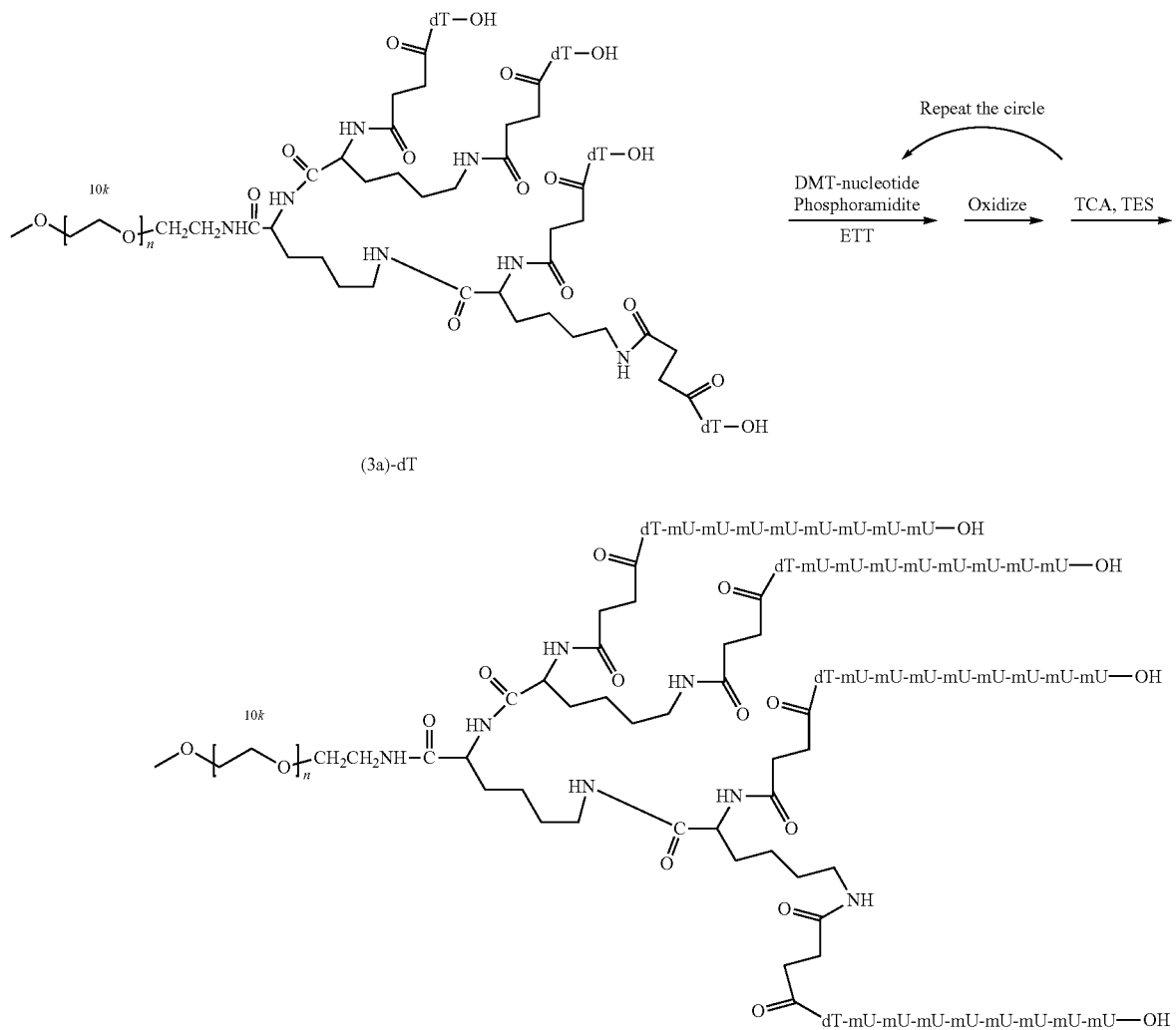

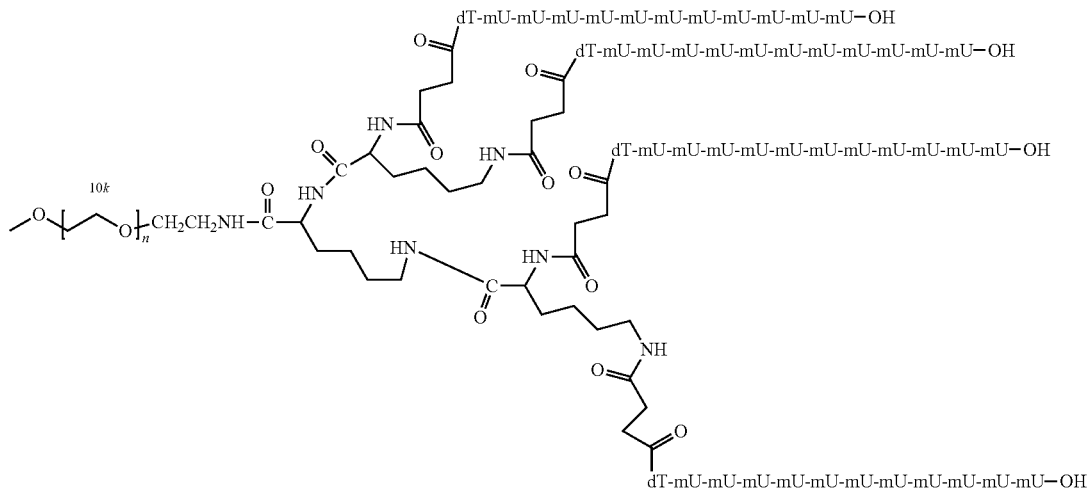

Figure 5:
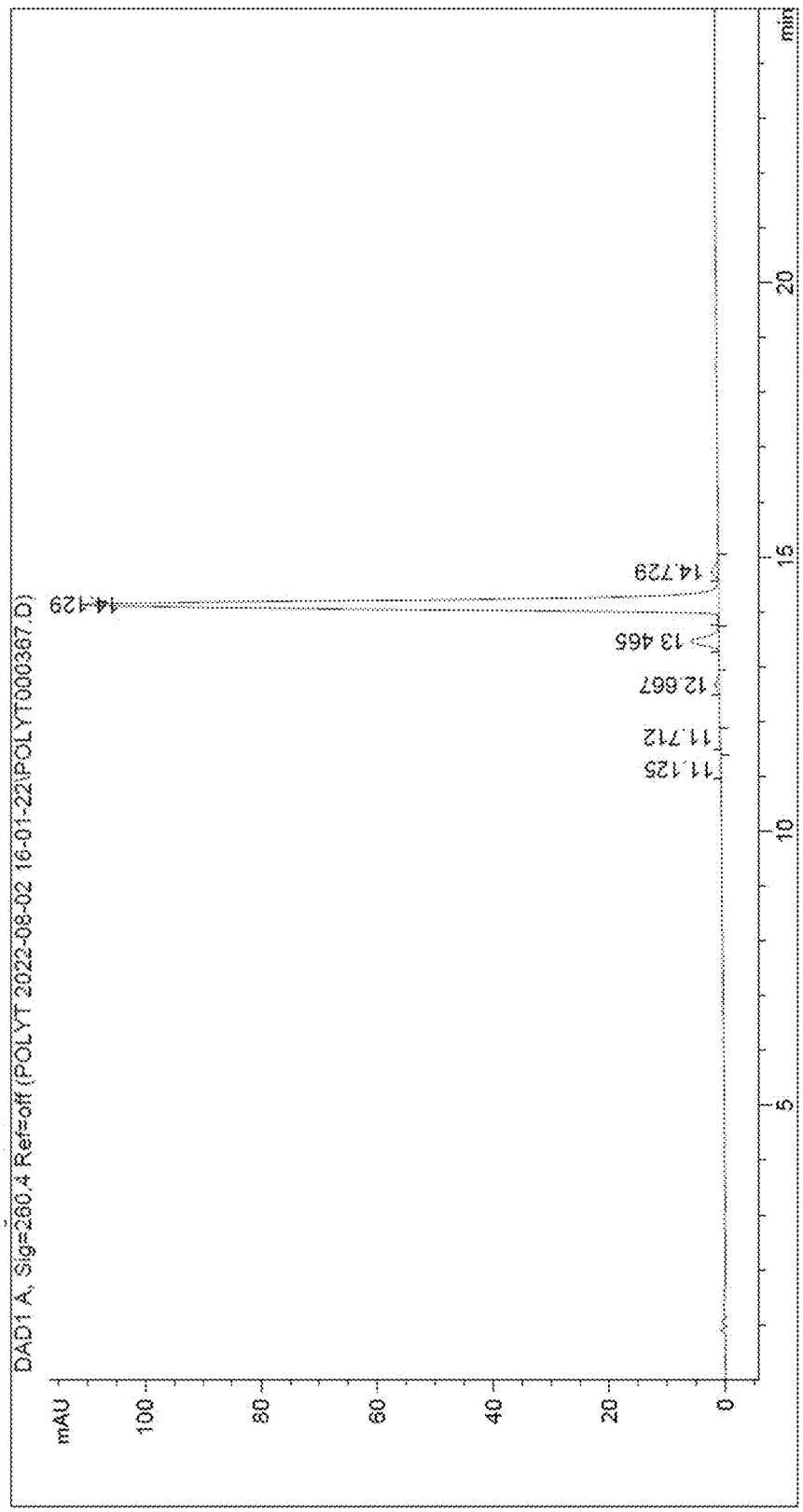
FIG. 5 is an HPLC profile of an dT-mU-mU-mU-mU-mU-mU-mU-mU oligonucleotide conjugate synthesized with polymer (3a) having an average molecular weight of 10 kDa by the liquid phase method disclosed herein according to an embodiment of the present application.

Polymer (3a)-dT conjugate having an average molecular weight of approximately 10 kDa was dissolved in a mixture of ETT activator (5-(ethylthio)-1H-tetrazole, 250 mM in 4.76 mL of anhydrous acetonitrile, Sigma Aldrich), and DMT-mU (i.e., DMT-2'-OMe-U) or DMT-U phosphoramidite (Hongene Biotech) in a 100 mL round bottom flask. After 60 minutes of constant magnetic stirring, 158 mg m-CPBA (3-Chloroperbenzoic acid, Sigma Aldrich) was added as a powder. After 10 minutes of constant stirring, 2.04 mL of trichloroacetic acid (TCA, 600 mg/mL in DCM) and 0.706 mL TES were added. After 10 minutes of constant stirring, the reaction mixture was poured into isopropanol with stirring. The precipitate was washed by diethyl ether for 2 times to give polymer (3a)-dT-mU-mU-mU-mU-mU-mU-mU-mU, which exhibited 94% full product purity (FLP) after nucleotide cleavage as shown in FIG. 5; and polymer (3a)-dT-mU-mU-mU-mU-mU-mU-mU-mU-mU-mU, which exhibited 88-90% full length product (FLP) purity after nucleotide cleavage.

Example 12. Elongation of Nucleotide Chain Polymer (3b)-9dT

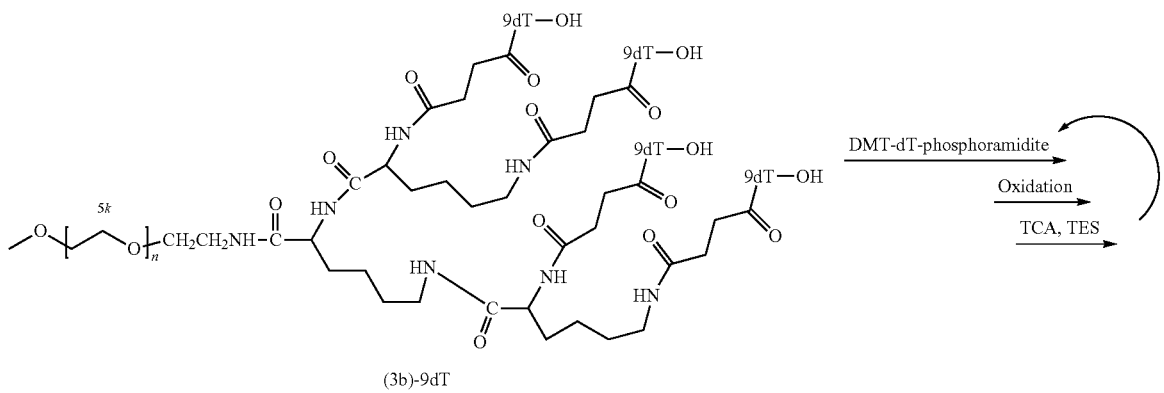

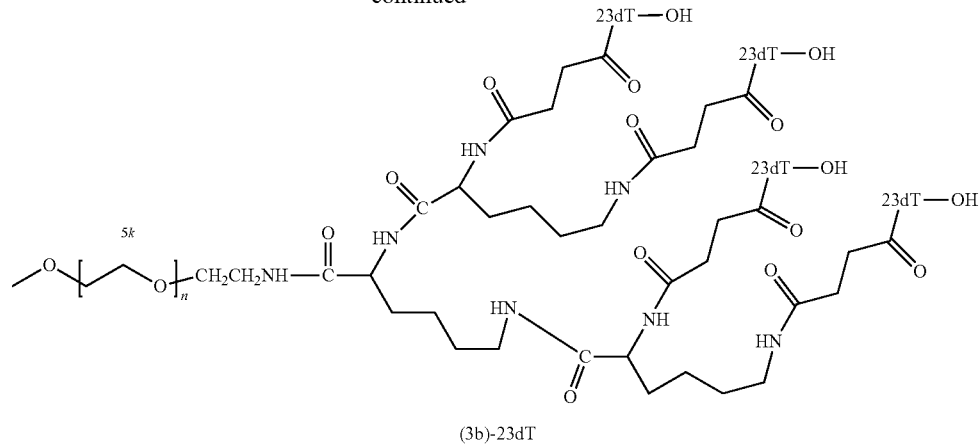

(3b)-23dT

Figure 6A:
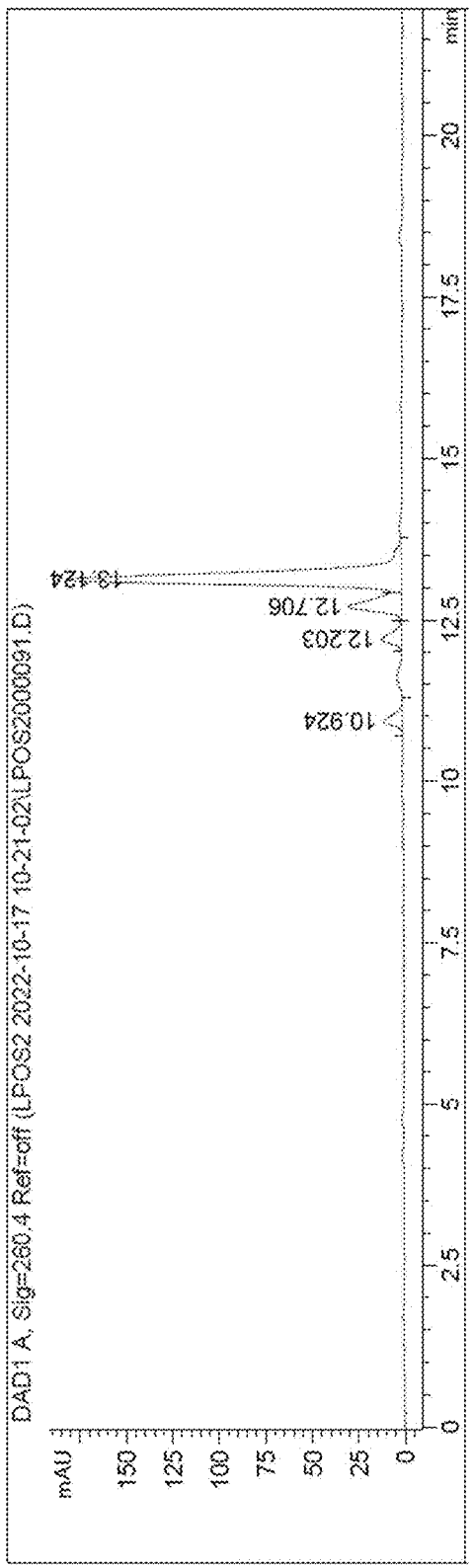
FIG. 6A is an HPLC profile of a 9dT oligonucleotide conjugate synthesized with polymer (3b) having an average molecular weight of 5 kDa by the liquid phase method disclosed herein according to an embodiment of the present application.
Figure 6B:
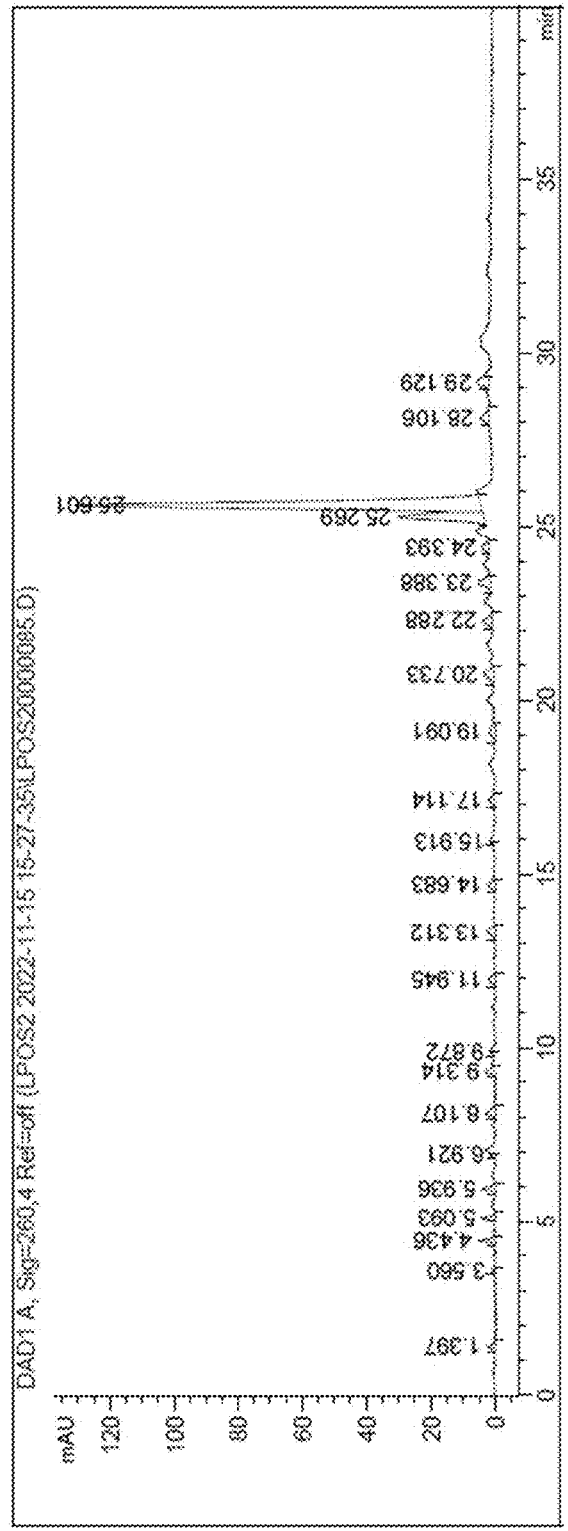
FIG. 6B is an HPLC profile of a oligonucleotide conjugate synthesized with polymer (3b) having an average molecular weight of 5 kDa by the liquid phase method disclosed herein according to an embodiment of the present application

Polymer (3b)-9dT conjugate having an average molecular weight of approximately 5 kDa PEG and having a 76.1% full product purity (FLP) (FIG. 6A), which was prepared using methods described in Examples 4 and 11, was dissolved in a mixture of ETT activator (5-(ethylthio)-1H-tetrazole in anhydrous acetonitrile), and DMT-dT phosphoramidite (Hongene Biotech) in a manner analogous to that described in Examples 4 and 11 to give polymer (3b)-10dT. This procedure was repeated 13 additional times with other nucleotides to prepare the sequence polymer (3b)-23dT which exhibited 63.2% full product purity (FLP) after nucleotide cleavage (FIG. 6B). The coupling reaction utilized an ACN/DCM mixture to improve polymer solubility.

Example 13. Preparation of Sulfurized Polymer (3b)-dT(S)dT(S)dT(S)dT(S)dT(S)dT(S)dT(S)dT

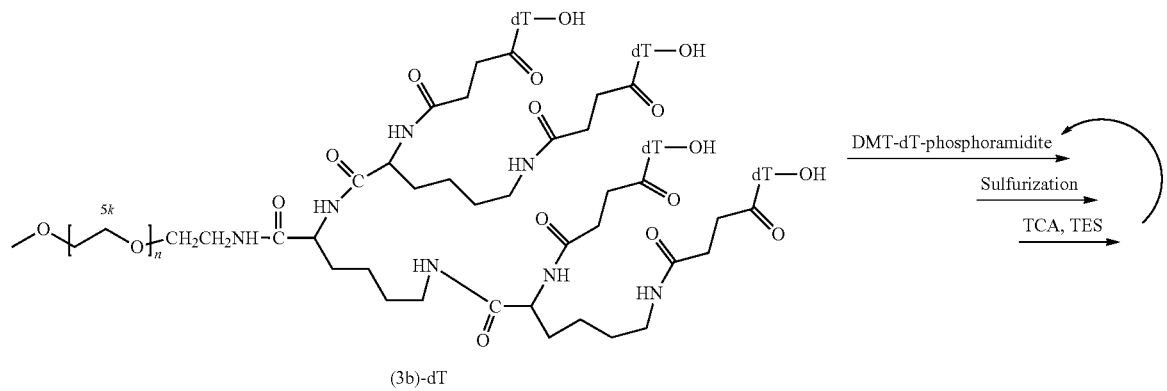

(3b)-dT

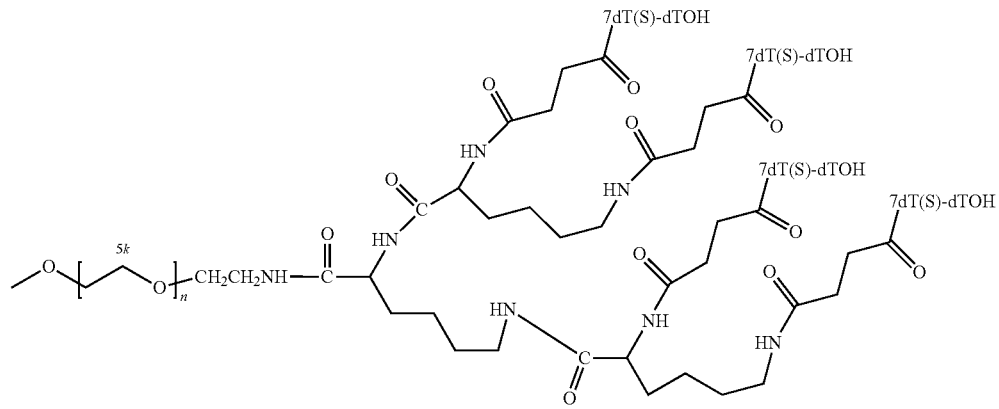

Figure 7:
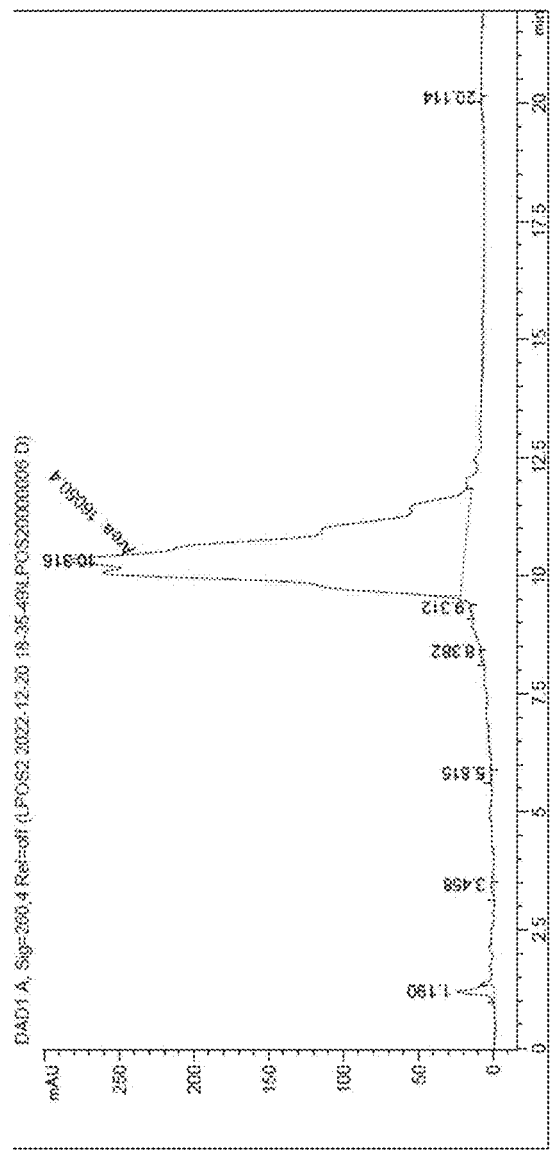
FIG. 7 is an HPLC profile of a dT(S)dT(S)dT(S)dT(S)dT (S)dT(S)dT(S)dT oligonucleotide conjugate synthesized with polymer (3b) having an average molecular weight of 5 kDa by the liquid phase method disclosed herein according to an embodiment of the present application.

Polymer (3b)-dT conjugate (223 mg) having an average molecular weight of approximately 5 kDa was dissolved in a mixture of ETT activator (5-(ethylthio)-1H-tetrazole, 250 mM in anhydrous acetonitrile, 2.05 mL, Sigma Aldrich), and 168 mg DMT-dT phosphoramidite (Hongene Biotech). After 90 minutes of constant shaking, 37 μL isopropanol was added. After 60 minutes of constant shaking, excess xanthane hydride (45 mg) was added, and the mixture was kept shaking for an additional 60 minutes. Excess trichloroacetic acid (600 mg/mL in DCM, 1.53 mL) and TES (527 μL) were added. After 10 minutes of constant shaking, the reaction mixture was poured onto isopropanol with stirring. The precipitate was washed with diethyl ether 2 times to give polymer (3b)-dT(S)dT. The (S) denotes a thiophosphate bond (P=S) in the oligonucleotide backbone. The above-mentioned procedure was repeated six additional times, to give polymer (3b)-dT(S)dT(S)dT(S)dT(S)dT(S)dT(S)dT(S)dT which exhibited 97.0% full product purity (FLP) after nucleotide cleavage (FIG. 7).

Example 14. Preparation of Polymer (1b)-dTdTdT(S)dT(S)dT(S)dT(S)dT(S)dT

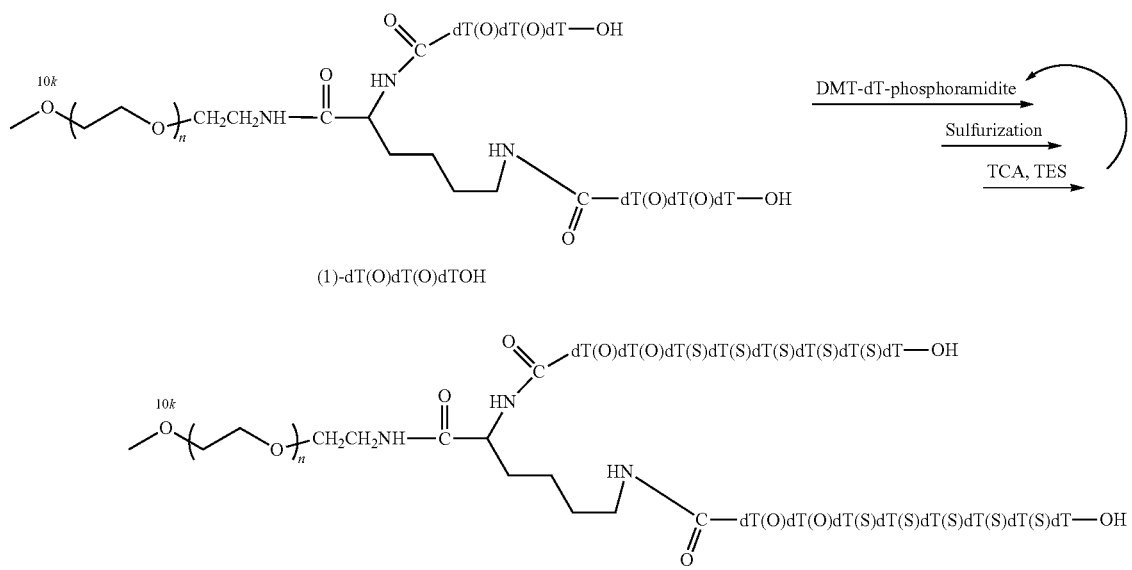

Figure 8:
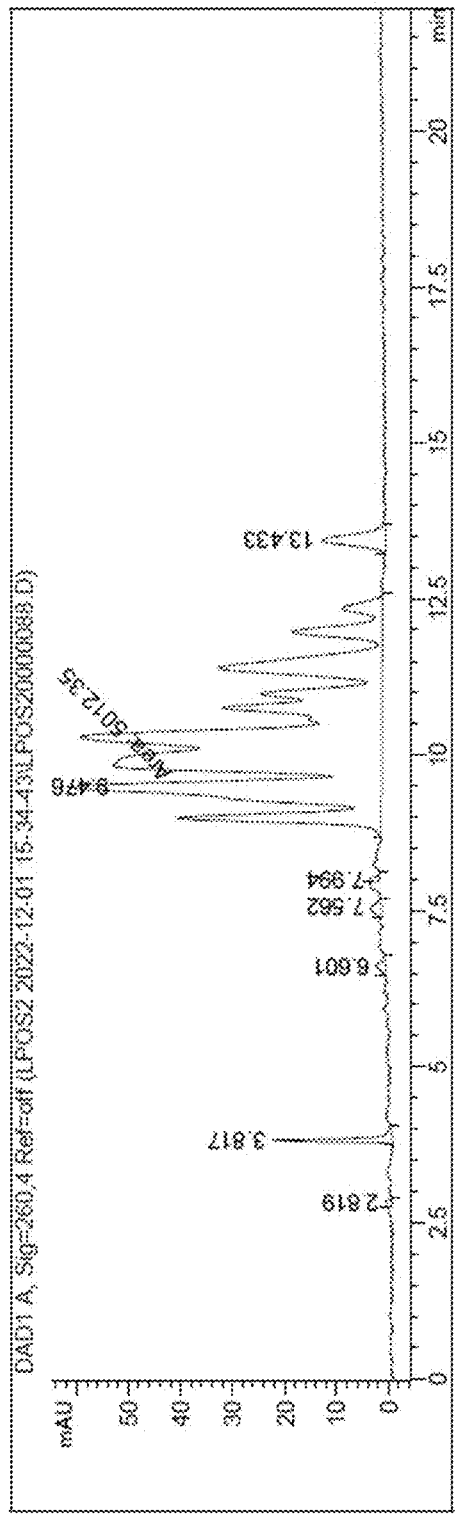
FIG. 8 is an HPLC profile of a dTdTdT(S)dT(S)dT(S)dT (S)dT(S)dT oligonucleotide conjugate synthesized with polymer (1b) having an average molecular weight of 10 kDa by the liquid phase method disclosed herein according to an embodiment of the present application.

Polymer (1b)-3dT conjugate (154 mg) having an average molecular weight of approximately 10 kDa, which was prepared according to methods described in Example 4, was treated in a manner analogous to that described in Example 13, to give Polymer (1b)-dTdTdT(S)dT. The procedure was repeated four additional times, to give polymer (1b)-dTdTdT(S)dT(S)dT(S)dT(S)dT(S)dT, which exhibited 96.3% full product purity (FLP) after nucleotide cleavage (FIG. 8).

Example 15. Mixed Backbone Oligonucleotide Study

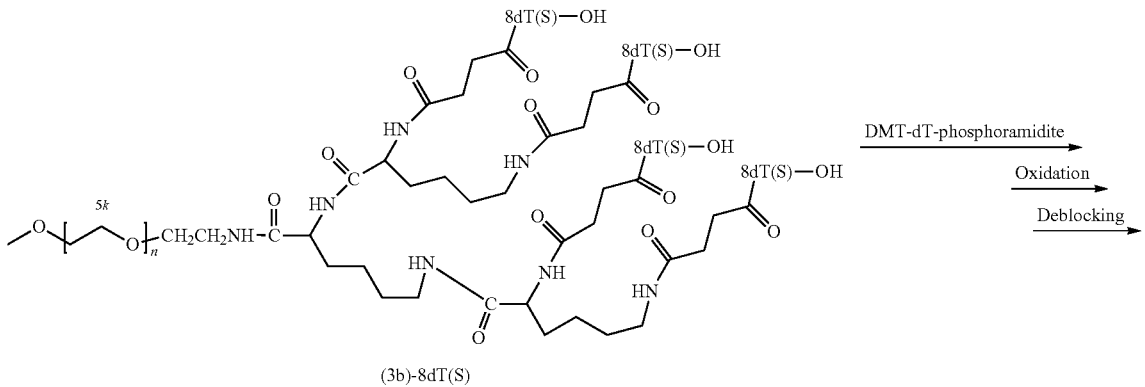

-continued

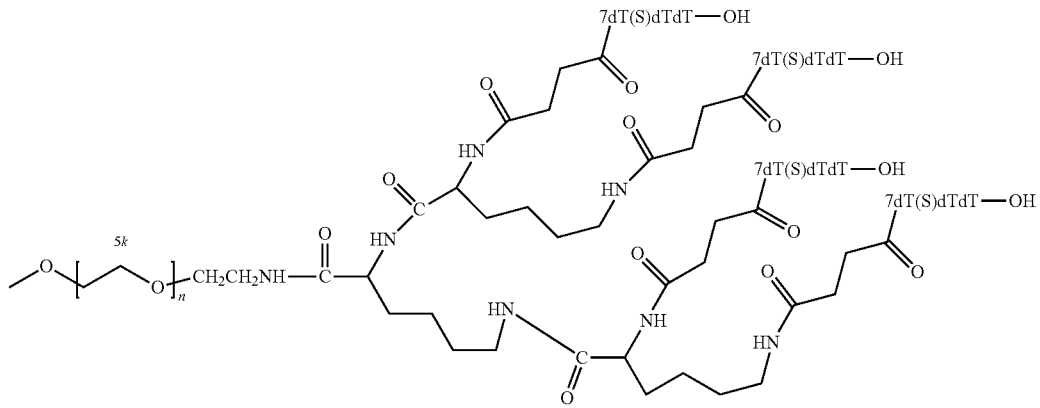

Figure 9A:
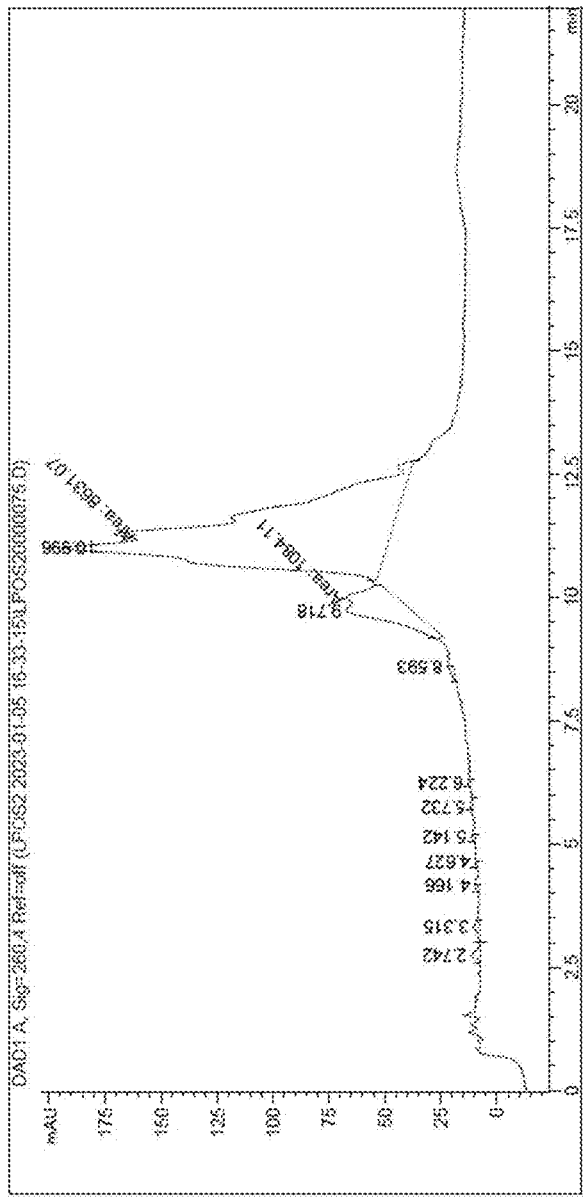
FIG. 9A is an HPLC profile of an 7dT(S)dTdT-OH oligonucleotide conjugate synthesized with polymer (1c) having an average molecular weight of 5 kDa using m-CPBA as the oxidant by the liquid phase method disclosed herein according to an embodiment of the present application.
Figure 9B:
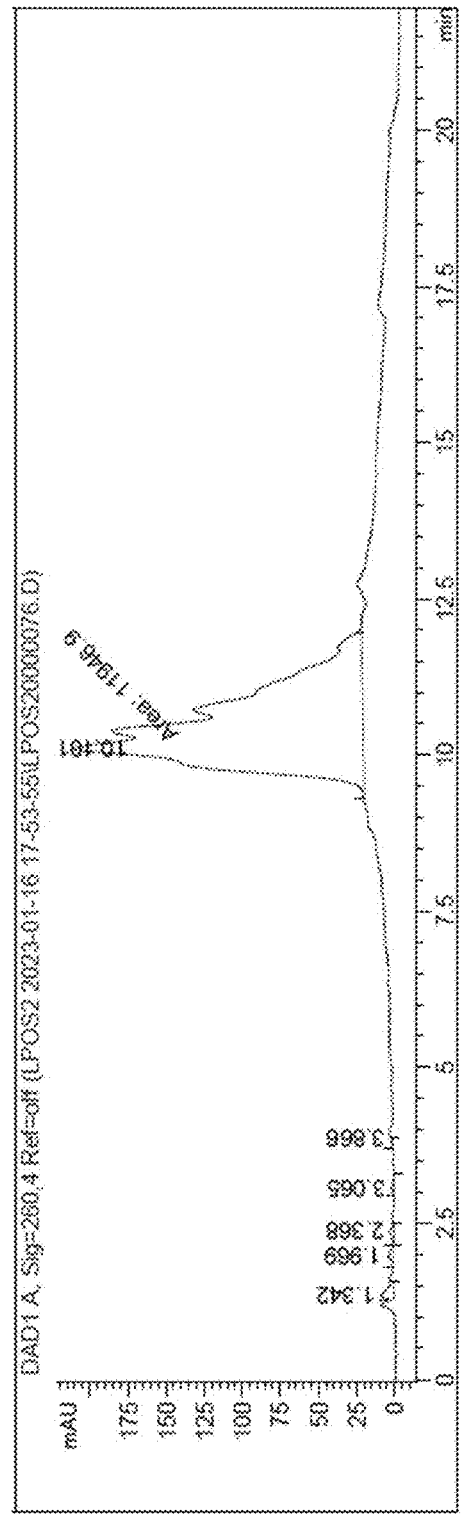
FIG. 9B is an HPLC profile of an 7dT(S)dTdT-OH oligonucleotide conjugate synthesized with polymer (1c) having an average molecular weight of 5 kDa using tBuOOH as the oxidant by the liquid phase method disclosed herein according to an embodiment of the present application.

Polymer (3b)-8dT(S) conjugate (FLP 97.0%) having a molecular weight of approximately 5 kDa was dissolved in a mixture of ETT activator (5-(ethylthio)-1H-tetrazole in anhydrous acetonitrile), and DMT-dT phosphoramidite (Hongene Biotech) in a manner analogous to that described in Example 4. However, reactions were performed using either m-chloroperoxybenzoic acid (m-CPBA) or tBuOOH as the oxidizing agent to give polymer (3b)-7dT(S)dT(O) dT-OH. HPLC results are provided in FIGS. 9A and 9B respectively, which showed m-CPBA acid induced obvious desulfurization but no obvious desulfurization observed for tBuOOH using as oxidation agent.

Example 16. Synthesis of Polymer (1b)-dT-8mU(VP)mU

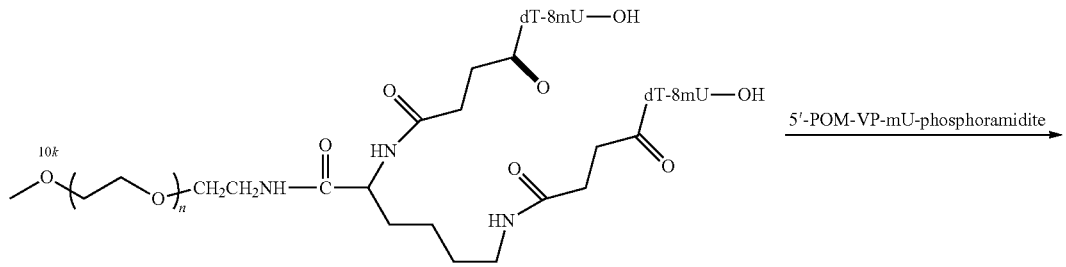

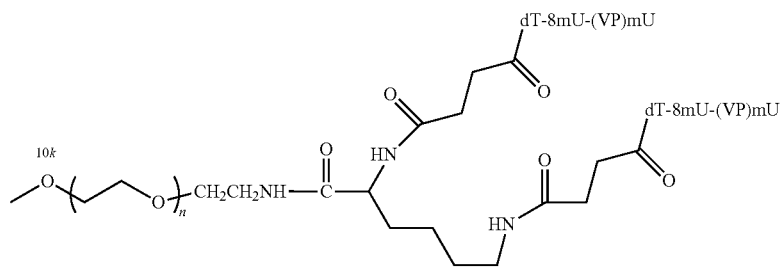

Figure 10:
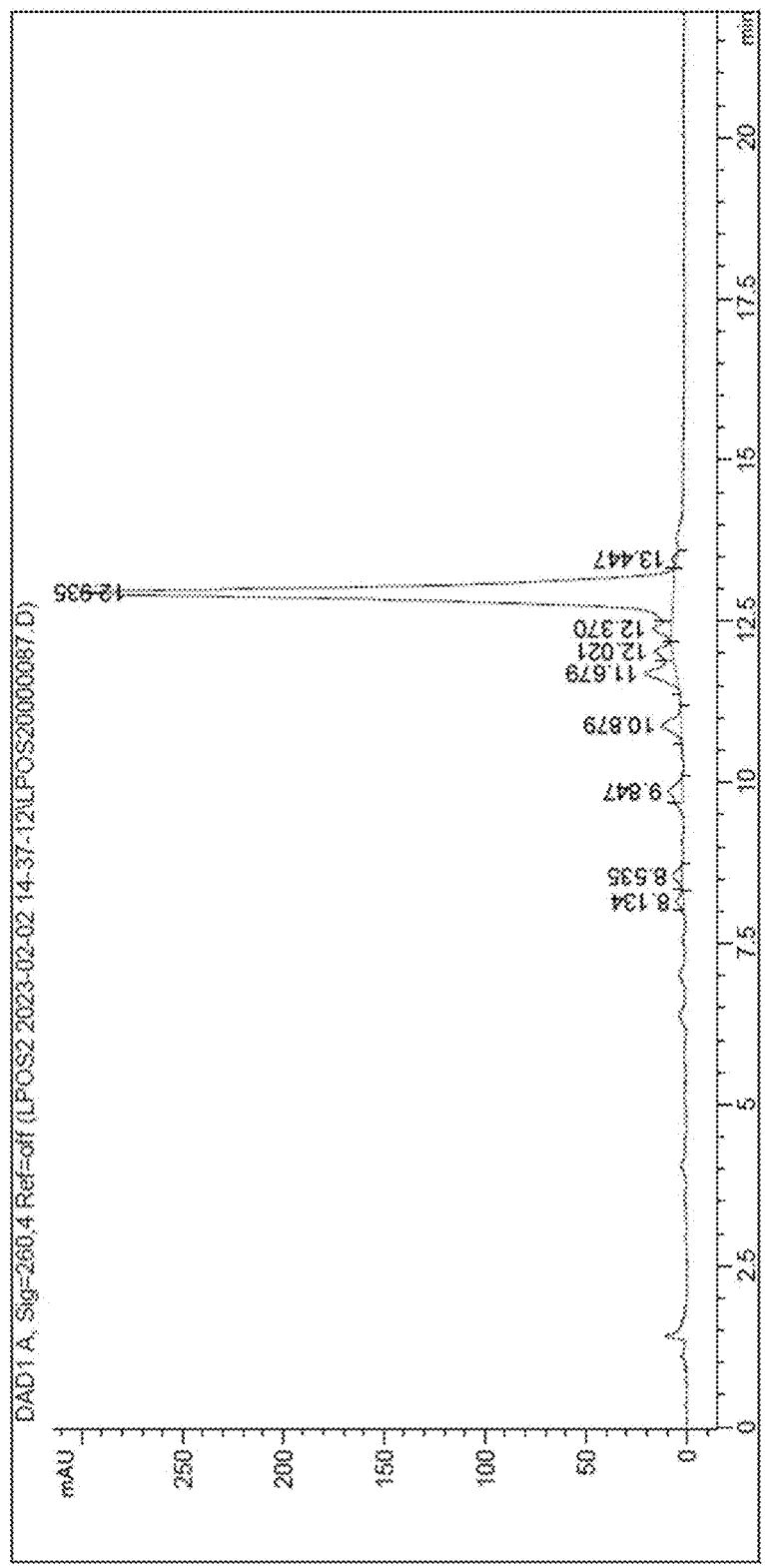
FIG. 10 is an HPLC profile of an dT-8mU(VP)mU oligonucleotide conjugate synthesized with polymer (1b) having an average molecular weight of 10 kDa by the liquid phase method disclosed herein according to an embodiment of the present application.

Polymer (1b)-dT-8mU conjugate having a molecular weight of approximately 10 kDa was dissolved in a mixture of ETT activator (5-(ethylthio)-1H-tetrazole in anhydrous acetonitrile), and 3 eq 5'-POM-VP-mU (i.e., 5'-[O,O-bis(pivaloyloxymethyl))-vinyl phosphonate, 2'-OMe-U phosphoramidite) (Hongene Biotech) in a manner analogous to that described in Example 4 without the deblocking step to give polymer (1b)-dT-8mU-VPmU which exhibited 83.0% full product purity (FLP) after nucleotide cleavage (FIG. 10). MS: 1599 [M-2H/2]-2; 1066 [M-3H/3]-3.

Example 17. Synthesis of Polymer (1c)-8dT-(VP)mA

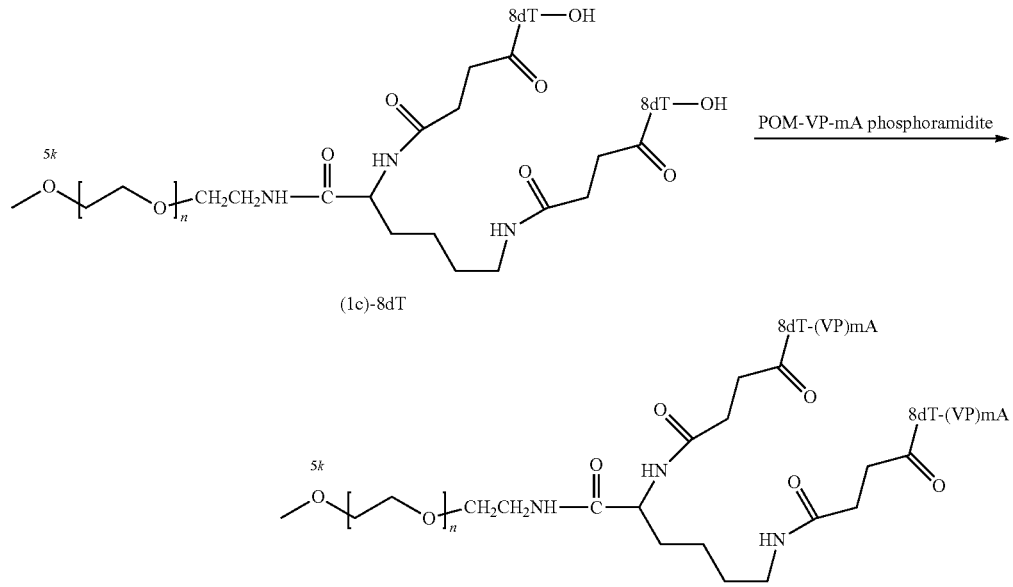

Figure 11:
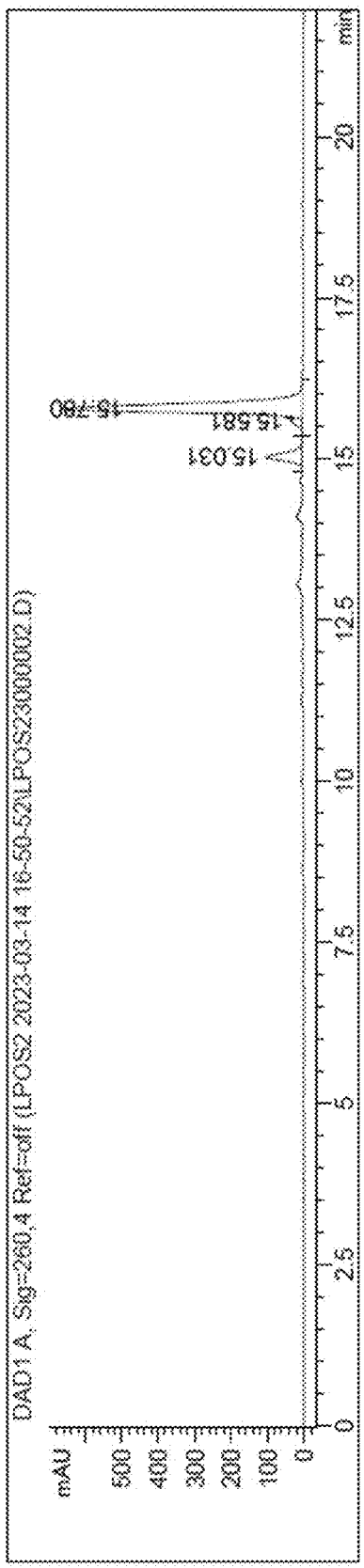
FIG. 11 is an HPLC profile of an 8dT-VPmA oligonucleotide conjugate synthesized with polymer (1c) having an average molecular weight of 5 kDa by the liquid phase method disclosed herein according to an embodiment of the present application.

Polymer (1)-8dT (FLP: 86%) conjugate having a molecular weight of approximately 5 kDa was dissolved in a mixture of ETT activator (5-(ethylthio)-1H-tetrazole in anhydrous acetonitrile), and 3 eq. 5'-POM-VP-mA (Hongene Biotech) in a manner analogous to that described in Example 4 without deblocking step to give polymer (1c)-8dT-VPmA which exhibited 82.0% full product purity (FLP) after nucleotides cleavage (FIG. 11). The result was confirmed by HPLC and LC/MS.

Example 18. Synthesis of Polymer (1c)-dTdT(S)dT

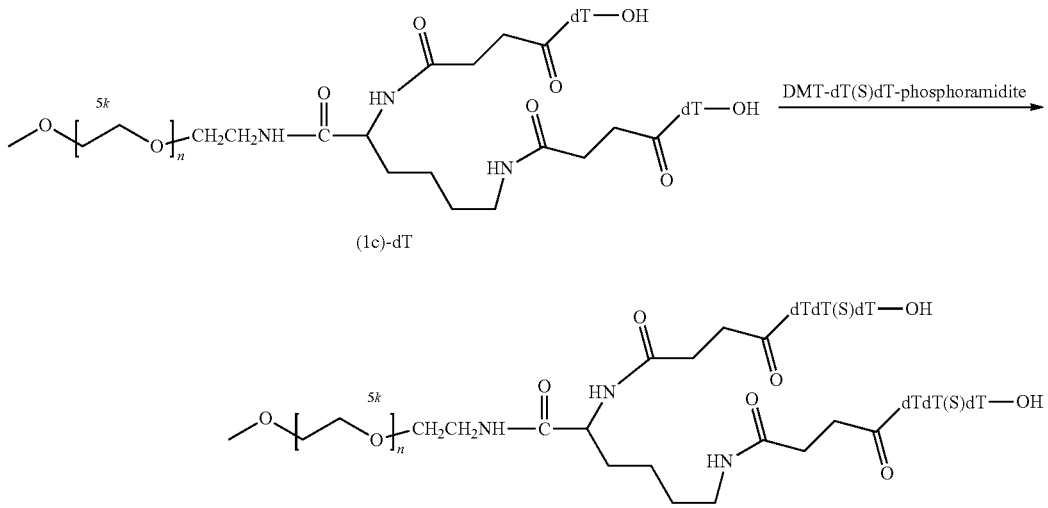

Figure 12:
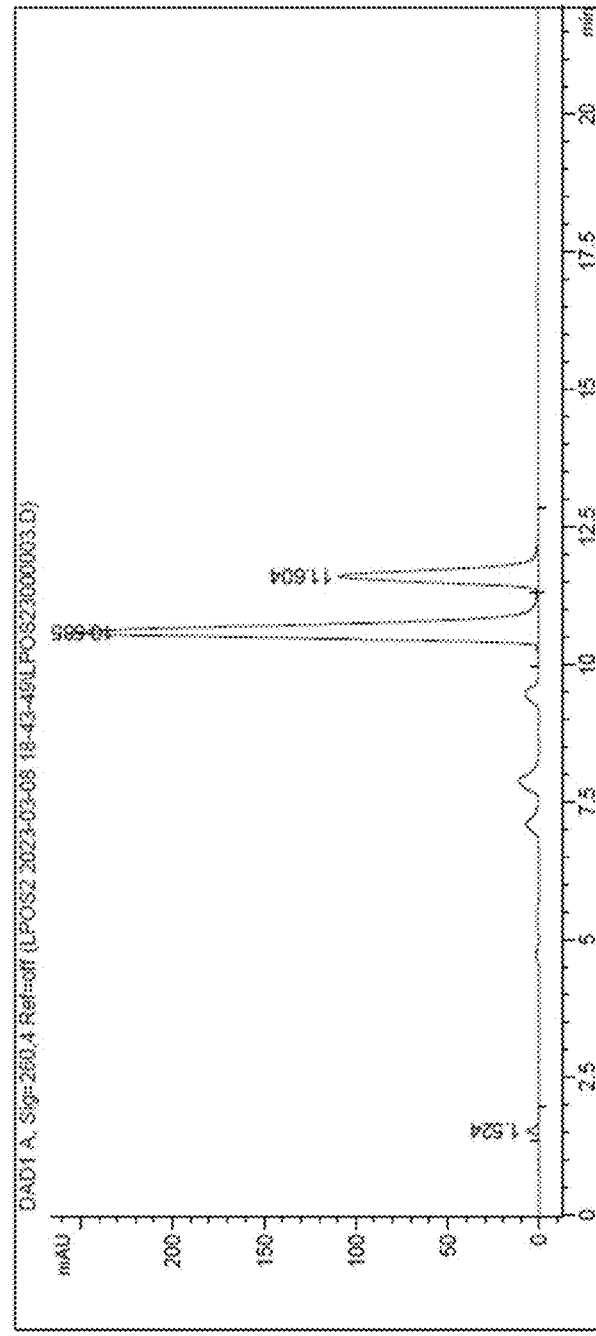
FIG. 12 is an HPLC profile of an dTdTdT(S)dT(S)dT(S) dT(S)dT(S)dT oligonucleotide conjugate synthesized with polymer (3b) having an average molecular weight of 5 kDa by the liquid phase method disclosed herein according to an embodiment of the present application.

Polymer (1c)-dT conjugate having a molecular weight of approximately 5 kDa was dissolved in a mixture of ETT activator (5-(ethylthio)-1H-tetrazole in anhydrous acetonitrile, 319 μL), and 1.03 eq DMT-dT(S)dT-phosphoramidite (Hongene Biotech) in a manner analogous to that described in Example 15 using tBuOOH as oxidation agent to give polymer (1c)-dTdT(S)dT, which exhibited 91.9% full product purity (FLP) after nucleotides cleavage (FIG. 12). Even the use of a slight excess of 1 molar equivalent of DMT-dT(P=S)dT-phosphoramidite, the conversion was up to 99.2%.

Example 19. Synthesis of DPEG-OH Anchors for Oligonucleotide Synthesis

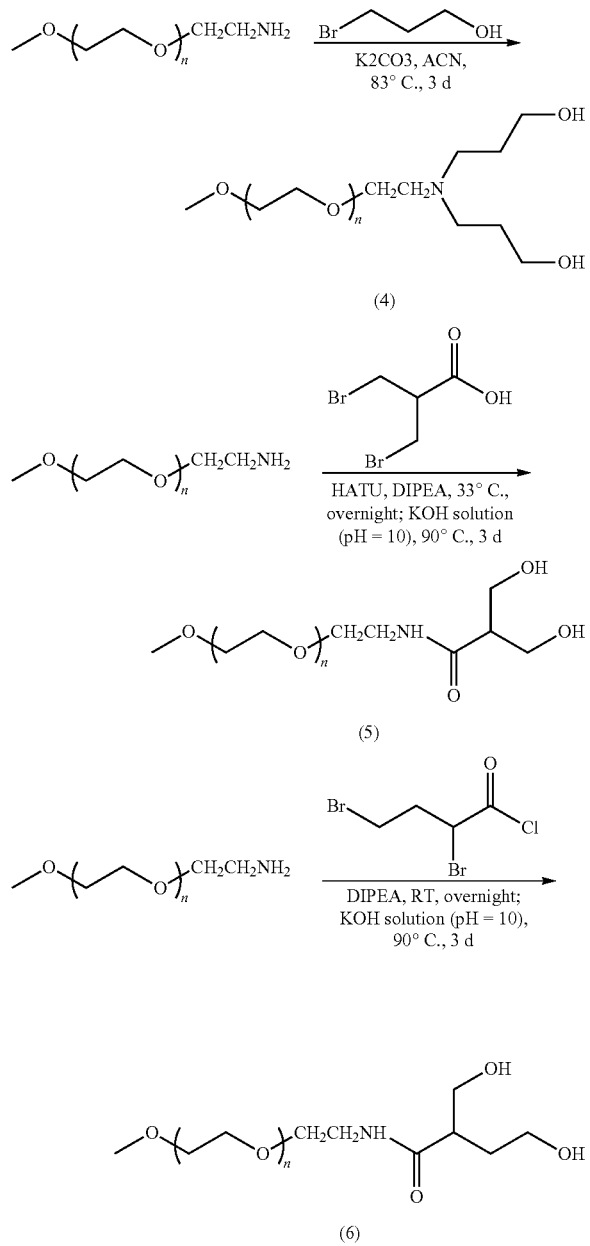

Synthesis of polymer (4): Commercially available PEG with an amine terminal (600 mg, 0.12 mmol) was stirred with 3-Bromo-1-propanol (133.4 mg, 0.96 mmol) and potassium carbonate (132.7 mg, 0.96 mmol) in 5 mL of ACN at 83° C. for a duration of 3 days. The completion of the reaction was confirmed using a ninhydrin test. The reaction mixture was filtered, and polymer (4) was obtained by subjecting the reaction mixture to three rounds of MTBE precipitation, with DCM being used as the resuspension solvent.

Synthesis of polymer (5): Commercially available PEG with an amine terminal (5 g, 1 mmol) was stirred with 3-Bromo-2-(bromomethyl)propionic acid (737.7 mg, 3.0 mmol), Hexafluorophosphate azabenzotriazole tetramethyl uronium (HATU, 1.25 g, 3.3 mmol), and N,N-Diisopropylethylamine (DIPEA, 775.4 mg, 6.0 mmol) in 50 mL of DMF at 33° C. overnight. The completion of the reaction was confirmed using a ninhydrin test. The intermediate product was obtained by pouring the reaction mixture into cold MBTE and drying the resulting solid under vacuum. The hydrolysis of halide was achieved in basic aqueous solution (pH=10) at 90° C. for 3 days. Following hydrolysis, the water was removed by lyophilization. The remaining solid was resuspended in DCM and the supernatant was then obtained by filtration. Polymer (5) was obtained by MTBE precipitation.

Synthesis of polymer (6): Commercially available PEG with an amine terminal (5 g, 1 mmol) was stirred with 2,4-Dibromobutyryl chloride (881 mg, 3 mmol) and DIPEA (775.4 mg, 6.0 mmol) in 50 mL of DMF at room temperature for overnight. The intermediate product was obtained by pouring the reaction mixture into cold MBTE and drying the resulting solid under vacuum. The hydrolysis of halide was achieved in basic aqueous solution (pH=10) at 90° C. for 3 days. Following hydrolysis, the water was removed by lyophilization. The remaining solid was resuspended in DCM and the supernatant was then obtained by filtration. Polymer (6) was obtained by MTBE precipitation.

Figure 13A:
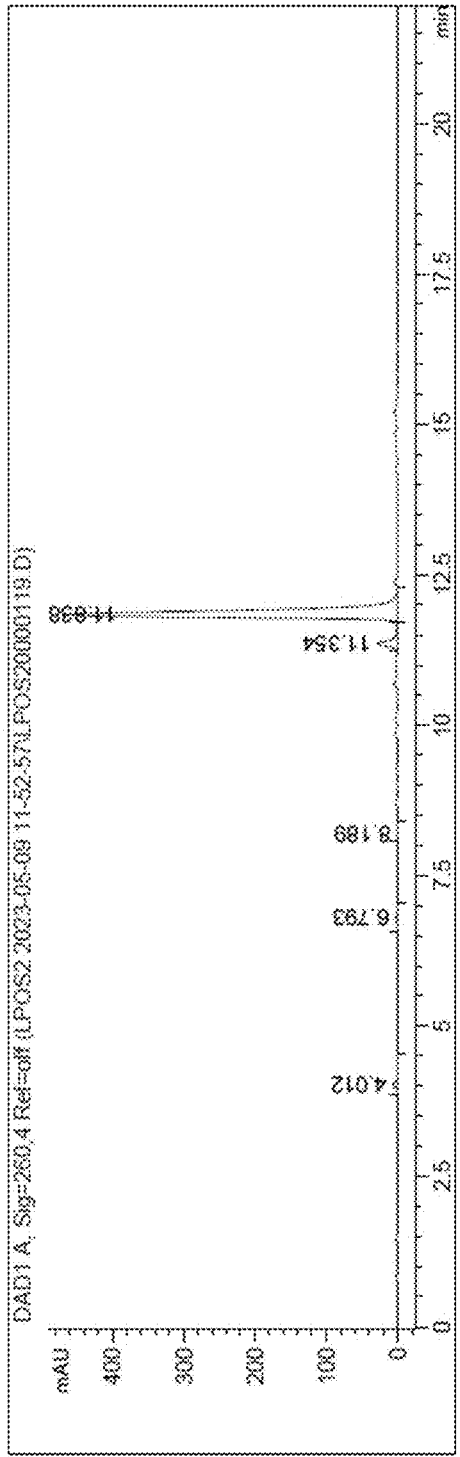
FIG. 13A is an HPLC profile of a polymer (4)-8dT-oligonucleotide conjugate by the liquid phase method disclosed herein according to an embodiment of the present application.
Figure 13B:
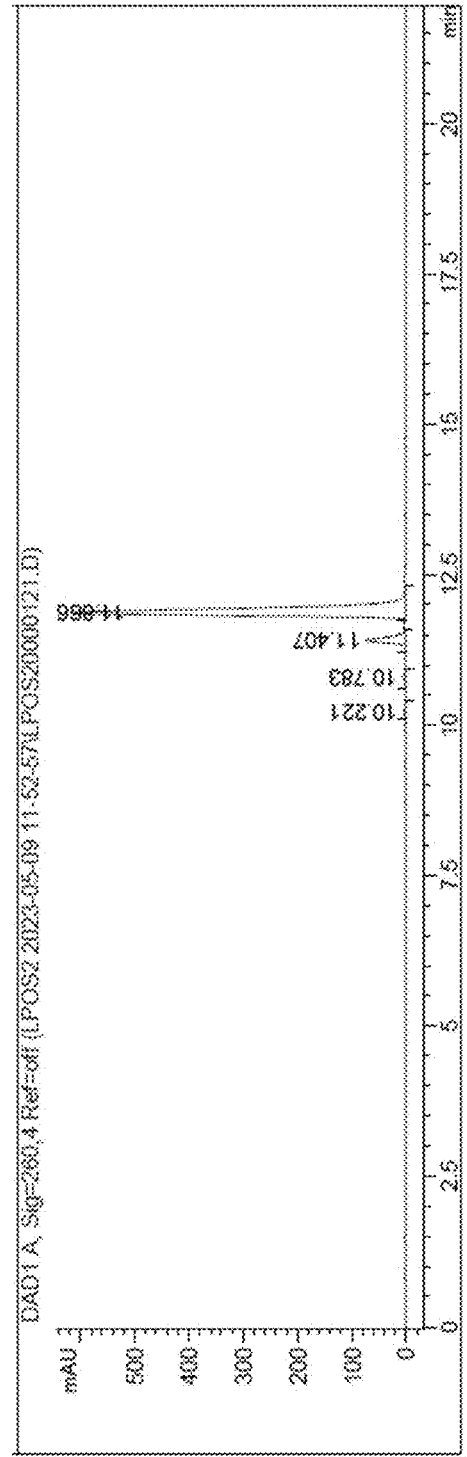
FIG. 13B is a HPLC profile of a polymer (6)-8dT-oligonucleotide conjugate by the liquid phase method disclosed herein according to an embodiment of the present application.

Example 20. Conjugation of Succinate dT to DPEG-OH Anchors and Elongation of Nucleotide Chain Polymer (4), (5), or (6) and 5'-O-(4,4'-dimethoxytrityl)-thymidine-3'-O-succinate, triethylamine salt (305.6 mg, 0.41 mmol) was dissolved in 3 mL of anhydrous DCM along with N-methylimidazole (NMI, 67.28 mg, 0.82 mmol), under argon. To this solution, 2,6-dichlorobenzoyl chloride (DcbCl, 85.81 mg, 0.41 mmol) was added and the mixture was stirred for 20 minutes to activate the succinate. The activated succinate solution was then slowly added dropwise to polymer 4, 5, or 6 (0.2 mmol) over a period of 40 minutes, and the reaction was allowed to continue at room temperature overnight. Then, to deblock the trityl group on the base, trichloroacetic acid (TCA, 600 mg/mL in DCM, 7.7 mmol) was added to the solution, followed by the addition of triethylsilane (TES, 4.6 mmol) as the scavenger reagent. The product was obtained by two rounds of IPA precipitation and MBTE wash, followed by vacuum drying. Further conjugation of more bases to polymer (4), (5), or (6)-dT anchors was carried out following procedures analogous to those described in Example 4. Oligonucleotides composed of 8 thymidines were synthesized using polymer (4), (5), or (6) as the starting material. The product obtained from polymers (4) and (6) were characterized by HPLC (FIG. 13A and FIG. 13B respectively). The yields and full product purity of 8dT oligonucleotide after cleavage is provided below in Table 2.

TABLE 2

Oligonucleotides synthesis summary after cleavage from polymer support

| Polymer Anchor | 8-dT Overall yield | FLP | DMT loading of PEG-1 dT | Yield for first 3 cycles (2 dT/3 dT/4 dT) |
|---|---|---|---|---|
| 4 | 69.8% (8 dT) | 90.2% | 382 μmole/g | 94.1%/90.5%/93.8% |
| 5 | 27.1% (5 dT) | n/a | 204 μmole/g | n/a |
| 6 | 68.0% (8 dT) | 89.9% | 244 μmole/g | 93.8%/92.2%/94.5% |

Example 21. Synthesis of DPEG-OH Anchor for Oligonucleotide Synthesis

Example 22. Conjugation of Succinate dT to DPEG-OH Anchor (7) and Elongation of Nucleotide Chain To conjugate the first thymidine base to polymer (7), 5'—O-(4,4'-dimethoxytrityl)-thymidine-3'-O-succinate, triethylamine salt (305.6 mg, 0.41 mmol) was dissolved in 3 mL of anhydrous DCM along with N-methylimidazole (NMI, 67.28 mg, 0.82 mmol), under argon. To this solution, 2,6-dichlorobenzoyl chloride (DcbCl, 85.81 mg, 0.41 mmol) was added and the mixture was stirred for 20 minutes to activate the succinate. The activated succinate solution was then slowly added dropwise to polymer 7 (0.2 mmol) over a period of 40 minutes, and the reaction was allowed to continue at room temperature overnight. Then, to deblock the trityl group on the base, trichloroacetic acid (TCA, 600 mg/mL in DCM, 7.7 mmol) was added to the solution, followed by the addition of triethylsilane (TES, 4.6 mmol) as the scavenger reagent. The product was obtained by two rounds of IPA precipitation and MBTE wash, followed by vacuum drying.

Further conjugation of more bases to polymer (7)-dT anchors was carried out following procedures analogous to those described in Example 4. Oligonucleotides composed of 8 thymidines were synthesized using polymer (7) as the starting material. The final oligonucleotide product was

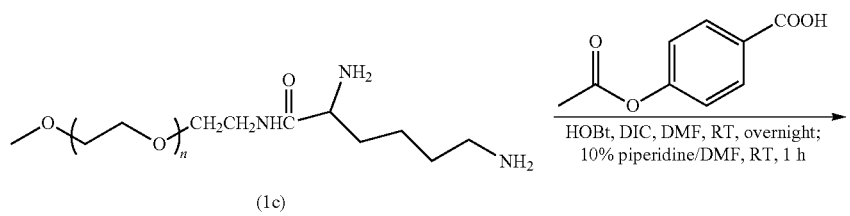

(1c)

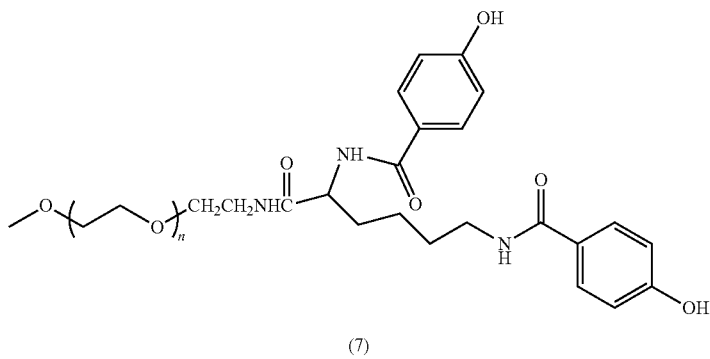

(7)

Figure 13C:
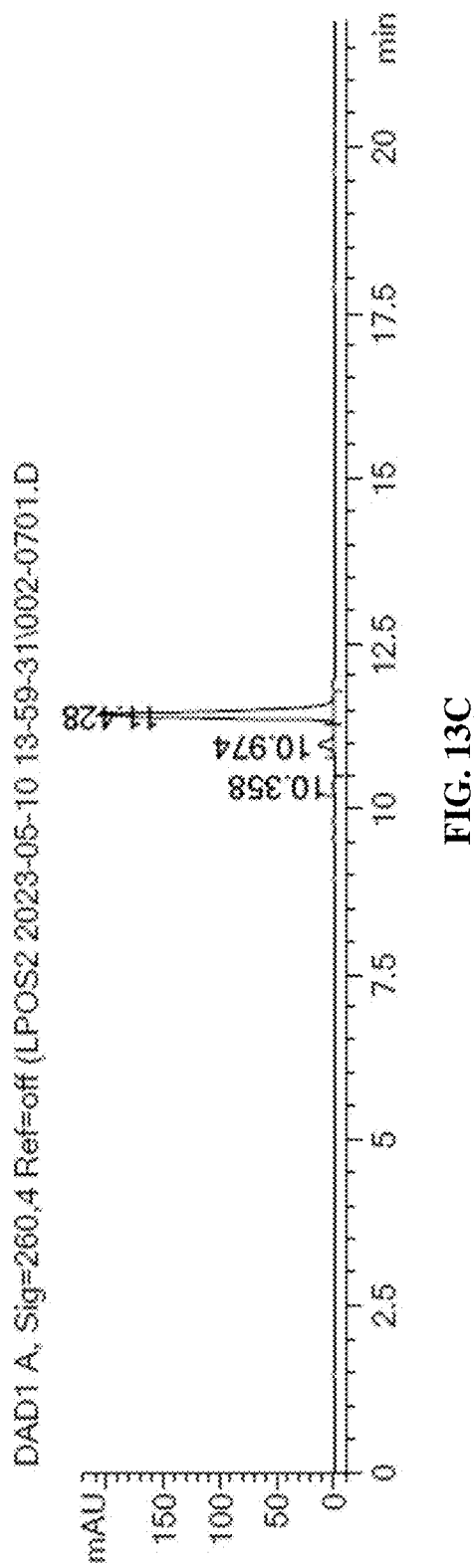
FIG. 13C is a HPLC profile of a polymer (7)-8dT-oligonucleotide conjugate by the liquid phase method disclosed herein according to an embodiment of the present application.

4-Acetoxybenzoic acid (216.2 mg, 1.2 mmol) was first preactivated by 1-Hydroxybenzotriazole (HOBt, 162.4 mg, 1.2 mmol) and N,N'-Diisopropylcarbodiimide (DIC, 166.58 mg, 1.32 mmol) in 5 mL of DMF for 10 minutes. This solution was then added to DPEG-diamine polymer (1c) (600 mg, 0.24 mmol) and stirred at room temperature overnight. The reaction was halted by IPA precipitation, followed by a wash with MTBE. To obtain the final product, 5 mL of a 10% piperidine/DMF solution was added to the precipitate and stirred for 1 hour at room temperature. Polymer (7) was obtained by two rounds of MTBE precipitation, followed by vacuum drying.

cleaved from the anchor using a 1:1 v/v mixture of $NH_4OH$ and methylamine) and characterized by HPLC (FIG. 13C) The product was recovered in 81.8% overall yield and exhibited 93.2% full product purity.

The LOPS polymer anchors having terminal hydroxy groups were observed to have comparable and/or higher loading, FLP and yield, as compared to LPOS polymer anchors with terminal —$NH_2$ groups. In addition, the asymmetric polymer anchors such as polymers (4) and (7) resulted in lower impurity levels based on HPLC results and were relative easier for precipitation during oligo synthesis.

What is claimed is:

1. A polymer for liquid phase oligonucleotide synthesis, having the structure of Formula (I):

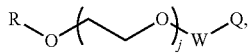

wherein:
R is H, or unsubstituted or substituted $C_1$-$C_6$ alkyl;
W is $C_1$-$C_{20}$ alkylene, a 2 to 20 membered heteroalkylene, or a bond;
Q is

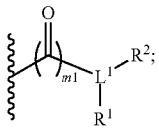

$L^1$ is $C_1$-$C_{20}$ alkylene, 2 to 20 membered heteroalkylene, optionally substituted phenylene, optionally substituted 5 to 6 membered heteroarylene, or optionally substituted $C_3$-$C_{10}$ cycloalkylene, or $C_1$-$C_{20}$ alkylene or 2 to 20 membered heteroalkylene in which one or more methylene repeating units is each independently replaced by a group selected from the group consisting of optionally substituted phenylene, optionally substituted 5 to 6 membered heteroarylene, optionally substituted $C_3$-$C_{10}$ cycloalkylene, —C(=O)—, —CH=CH—, and —C≡C—;
each of $R^1$ and $R^2$ is independently —$OR^3$ or —$N^{R4a}R^{4b}$;
$R^3$ is H, a hydroxy protecting group, or

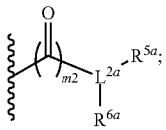

each $R^{4a}$ and $R^{4b}$ is independently H, —C(=O)($C_1$-$C_6$ alkyl), —C(=O) phenyl, an amino protecting group, or

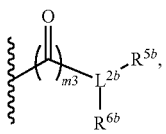

or $R^{4a}$ and $R^{4b}$ taken together is a divalent amino protecting group;
each of $L^{2a}$ and $L^{2b}$ is independently $C_1$-$C_{20}$ alkylene, 2 to 20 membered heteroalkylene, optionally substituted phenylene, optionally substituted 5 to 6 membered heteroarylene, or optionally substituted $C_3$-$C_{10}$ cycloalkylene, or $C_1$-$C_{20}$ alkylene or 2 to 20 membered heteroalkylene in which one or more methylene repeating units is each independently replaced by a group selected from the group consisting of optionally substituted phenylene, optionally substituted 5 to 6 membered heteroarylene, optionally substituted $C_3$-$C_{10}$ cycloalkylene, —C(=O)—, —CH=CH—, and —C≡C—;

each of $R^{5a}$, $R^{5b}$, $R^{6a}$ and $R^{6b}$ is independently H, —$OR^7$ or —$NR^{8a}R^{8b}$;
each of $R^7$ is independently H, a hydroxy protecting group, or

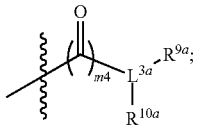

each of $R^{8a}$ and $R^{8b}$ is independently H, —C(=O)($C_1$-$C_6$ alkyl), —C(=O) phenyl, an amino protecting group, or

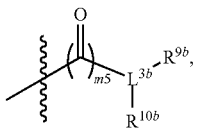

or $R^{8a}$ and $R^{8b}$ taken together is a divalent amino protecting group;
each of $L^{3a}$ and $L^{3b}$ is independently $C_1$-$C_{20}$ alkylene, 2 to 20 membered heteroalkylene, optionally substituted phenylene, optionally substituted 5 to 6 membered heteroarylene, or optionally substituted $C_3$-$C_{10}$ cycloalkylene, or $C_1$-$C_{20}$ alkylene or 2 to 20 membered heteroalkylene in which one or more methylene repeating units is each independently replaced by a group selected from the group consisting of optionally substituted phenylene, optionally substituted 5 to 6 membered heteroarylene, optionally substituted $C_3$-$C_{10}$ cycloalkylene, —C(=O)—, —CH=CH—, and —C≡C—;
each of $R^{9a}$, $R^{9b}$, $R^{10a}$ and $R^{10b}$ is independently H, —$OR^{11}$ or —$NR^{12a}R^{12b}$;
each of $R^{11}$ is independently H, a hydroxy protecting group, or

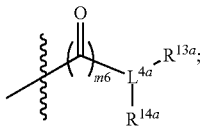

each of $R^{12a}$ and $R^{12b}$ is independently H, —C(=O)($C_1$-$C_6$ alkyl), —C(=O) phenyl, an amino protecting group, or

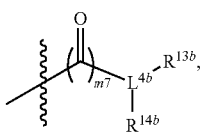

or $R^{12a}$ and $R^{12b}$ taken together is a divalent amino protecting group;
each of $L^{4a}$ and $L^{4b}$ is independently $C_1$-$C_{20}$ alkylene, 2 to 20 membered heteroalkylene, optionally substituted phenylene, optionally substituted 5 to 6 membered heteroarylene, or optionally substituted $C_3$-$C_{10}$ cycloalkylene, or $C_1$-$C_{20}$ alkylene or 2 to 20 membered heteroalkylene in which one or more methylene repeating units is each independently replaced by a group selected from the group consisting of optionally substituted phenylene, optionally substituted 5 to 6 membered heteroarylene, optionally substituted $C_3$-$C_{10}$ cycloalkylene, —C(=O)—, —CH=CH—, and —C≡C—:

each of $R^{13a}$, $R^{13b}$, $R^{14a}$ and $R^{14b}$ is independently H, —OH, protected hydroxy, —NH$_2$, —NH (optionally substituted $C_1$-$C_6$ alkyl), or protected amino;

each of m1, m2, m3, m4, m5, m6 and m7 is independently 0 or 1; and j is an integer from 150 to 1500.

2. The polymer of claim 1, wherein R is methyl.

3. The polymer of claim 1, wherein W is —CH$_2$CH$_2$NH—, —CH$_2$CH$_2$O—, or —CH$_2$CH$_2$—.

4. The polymer of claim 1, wherein $L^1$ is a $C_2$-$C_{10}$ alkylene linker or wherein $L^1$ is 3 to 12 membered heteroalkylene containing one, two or three heteroatoms selected from N, O and S.

5. The polymer of claim 1, wherein Q is selected from the group consisting of

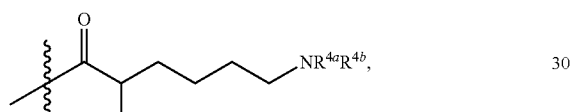

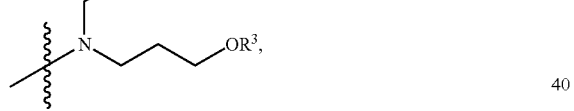

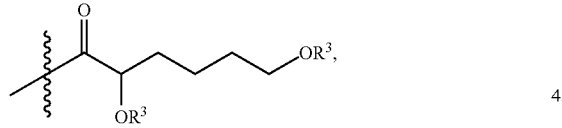

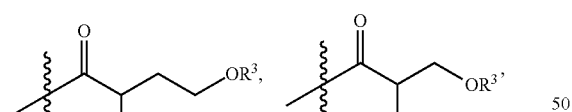

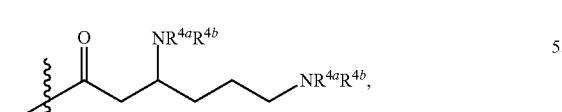

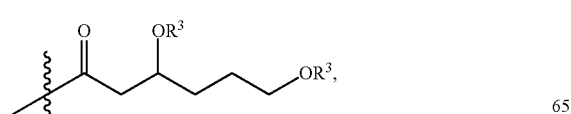

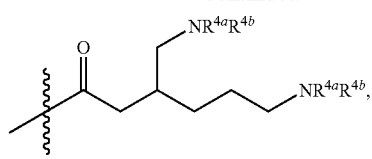

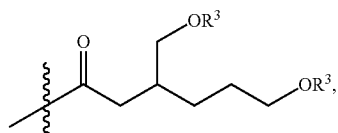

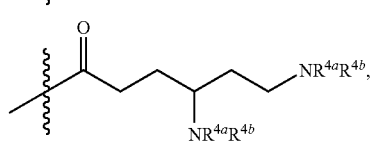

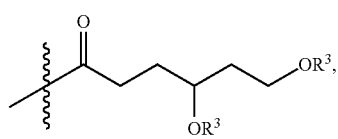

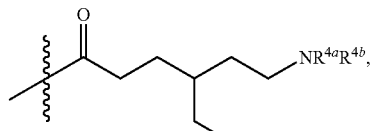

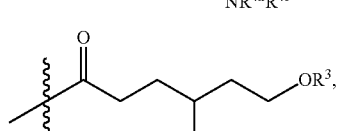

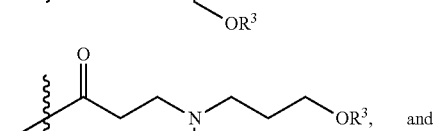, and

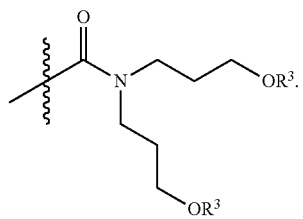

6. The polymer of claim 1, wherein each $R^3$ is independently H or hydroxy protecting group.

7. The polymer of claim 1, wherein one $R^3$ is H or a hydroxy protecting group, and the other $R^3$ is

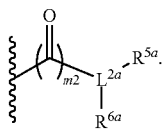

8. The polymer of claim 1, wherein each $R^{4a}$ is H, each $R^{4b}$ is independently H, —C(=O)($C_1$-$C_6$ alkyl), —C(=O) phenyl, an amino protecting group, or

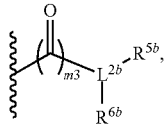

or the hydrogen in —NHR$^{4b}$ is absent, and $R^{4b}$ is a divalent amino protecting group.

9. The polymer of claim 8, wherein each $R^{4b}$ is independently H, —C(=O)CH$_3$, or an amino protecting group.

10. The polymer of claim 8, wherein one $R^{4b}$ is H or an amino protecting group, and the other $R^{4b}$ is

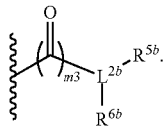

11. The polymer of claim 8, wherein each of $R^3$ is independently

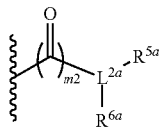

and each of $R^{4b}$ is independently

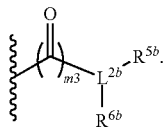

12. The polymer of claim 11, wherein each of m2 and m3 is 1.

13. The polymer of claim 12, wherein each of $L^{2a}$ and $L^{2b}$ is independently optionally substituted phenylene, $C_2$-$C_6$ alkylene, or 3 to 12 membered heteroalkylene comprising one, two or three heteroatoms selected from N, O and S; or $C_2$-$C_6$ alkylene or 3 to 12 membered heteroalkylene, wherein one methylene unit of the $C_2$-$C_6$ alkylene or 3 to 12 membered heteroalkylene is replaced by an optionally substituted phenylene.

14. The polymer of claim 1, wherein each $R^{8a}$ is H, and each of $R^{5a}$, $R^{5b}$, $R^{6a}$ and $R^{6b}$ is independently H, —OR$^7$ or —NHR$^{8b}$, each $R^{8b}$ is independently H, —C(=O)($C_1$-$C_6$ alkyl), —C(=O) phenyl, an amino protecting group, or

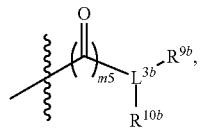

or the hydrogen in —NHR$^{8b}$ is absent, and $R^{8b}$ is a divalent amino protecting group.

15. The polymer of claim 14, wherein each of $R^{5a}$, $R^{5b}$, $R^{6a}$ and $R^{6b}$ is independently H, —OH, a protected hydroxy, —NH$_2$, —NHC(=O)CH$_3$, or a protected amino.

16. The polymer of claim 14, wherein at least one of $R^{5a}$, $R^{5b}$, $R^{6a}$ and $R^{6b}$ is independently —OR$^7$ or —NHR$^{8b}$, at least one of $R^7$ is

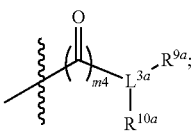

and at least one of $R^{8b}$ is

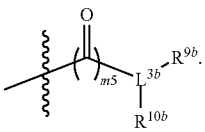

17. The polymer of claim 14, wherein each one of $R^{5a}$, $R^{5b}$, $R^{6a}$ and $R^{6b}$ is independently —OR$^7$ or —NHR$^{8b}$, each of $R^7$ is independently

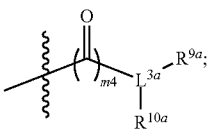

and each $R^{8b}$ is independently

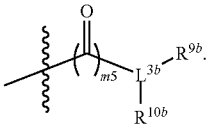

18. The polymer of claim 16, wherein each of m4 and m5 is 1.

19. The polymer of claim 16, wherein each of $L^{3a}$ and $L^{3b}$ is independently optionally substituted phenylene, $C_2$-$C_6$ alkylene or 3 to 12 membered heteroalkylene comprising one, two or three heteroatoms selected from N, O and S; or $C_2$-$C_6$ alkylene or 3 to 12 membered heteroalkylene, wherein one methylene unit of the $C_2$-$C_6$ alkylene or 3 to 12 membered heteroalkylene is replaced by an optionally substituted phenylene.

20. The polymer of claim 1, wherein each $R^{12a}$ is H, and each of $R^{9a}$, $R^{9b}$, $R^{10a}$ and $R^{10b}$ is independently H, —$OR^{11}$ or —$NHR^{12b}$, each $R^{12b}$ is independently H, —C(=O)($C_1$-$C_6$ alkyl), —C(=O) phenyl, an amino protecting group, or

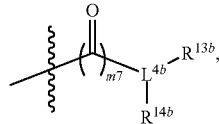

or the hydrogen in —$NHR^{12b}$ is absent, and $R^{12b}$ is a divalent amino protecting group.

21. The polymer of claim 20, wherein each of $R^{9a}$, $R^{9b}$, $R^{10a}$ and $R^{10b}$ is independently H, —OH, a protected hydroxy, —$NH_2$, —NHC(=O)$CH_3$, or a protected amino.

22. The polymer of claim 20, wherein at least one of $R^{9a}$, $R^{9b}$, $R^{10a}$ and $R_{10b}$ is independently —$OR^{11}$ or —$NHR^{12b}$, at least one of $R^{11}$ is

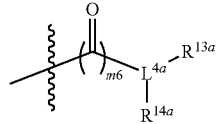

and at least one $R^{12b}$ is

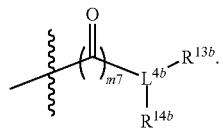

23. The polymer of claim 20, wherein each of $R^{9a}$, $R^{9b}$, $R^{10a}$ and $R^{10b}$ is independently —$OR^{11}$ or —$NHR^{12b}$, each of $R^{11}$ is

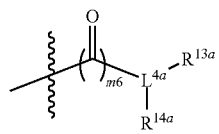

and each $R^{12b}$ is

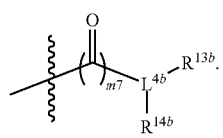

24. The polymer of claim 22, wherein each of m6 and m7 is 1.

25. The polymer of claim 22, wherein each of $L^{4a}$ and $L^{4b}$ is independently $C_2$-$C_6$ alkylene or 3 to 12 membered heteroalkylene comprising one, two or three heteroatoms selected from N, O and S.

26. The polymer of claim 22, wherein each of $R^{13a}$, $R^{13b}$, $R^{14a}$ and $R^{14b}$ is independently H, —OH, protected hydroxy, —$NH_2$, —NHC(=O)$CH_3$, or a protected amino.

27. The polymer of claim 1, having a structure of Formula (Ia):

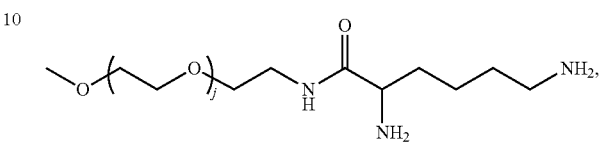

wherein j is 150 to 500.

28. The polymer of claim 1, having the structure of Formula (Ib), (Ib-1), (Ic) or (Ic-1):

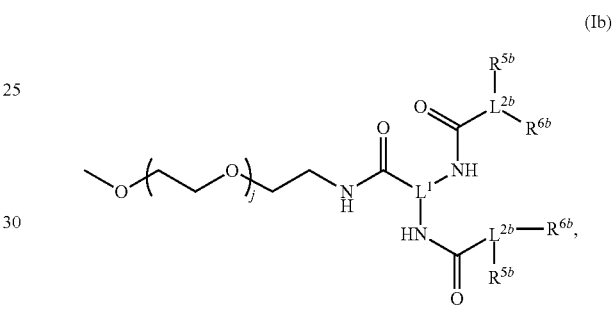

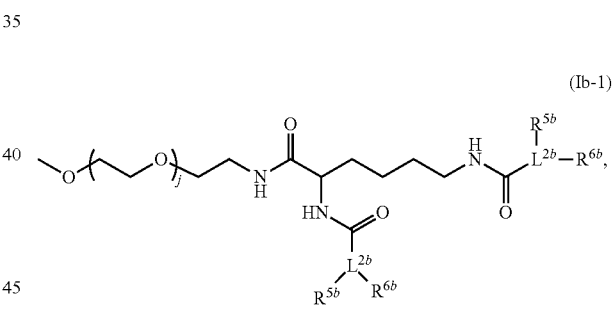

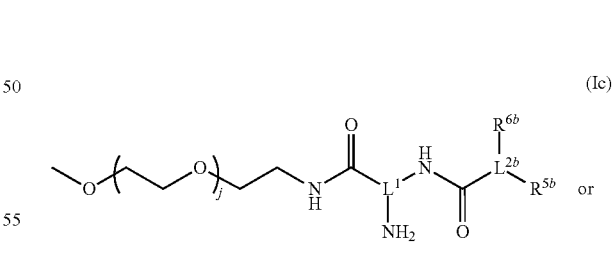

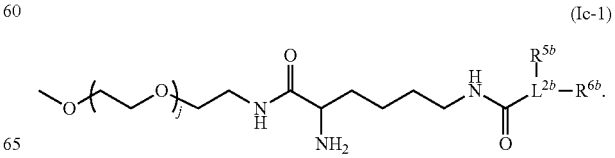

29. The polymer of claim 28, wherein the structure of Formula (Ib-1) has the structure of Formula (Ib-2) or (Ib-3):

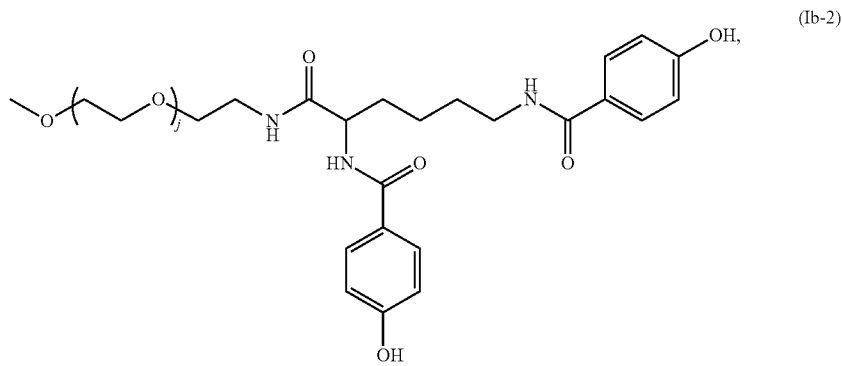

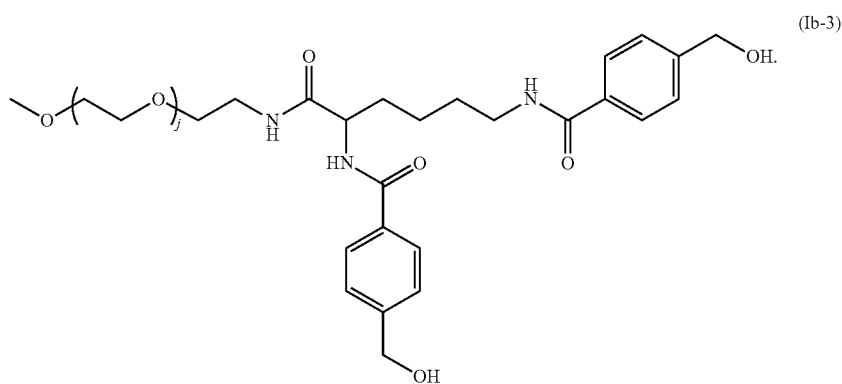

30. The polymer of claim 28, wherein the structure of Formula (Ib-1) has the structure of Formula (Ib-4):

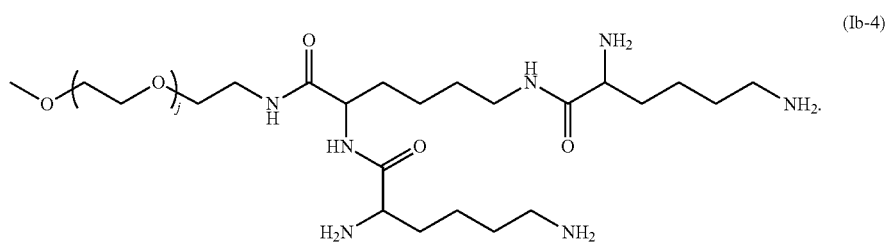

31. The polymer of claim 28, wherein each of $R^{5b}$ and $R^{6b}$ is independently —$NH_2$ or —NHAc, or each of $R^{5b}$ and $R^{6b}$ is —OH.

32. The polymer of claim 1, wherein the structure of Formula (I) has the structure of Formula (Id), (Ie), or (If):

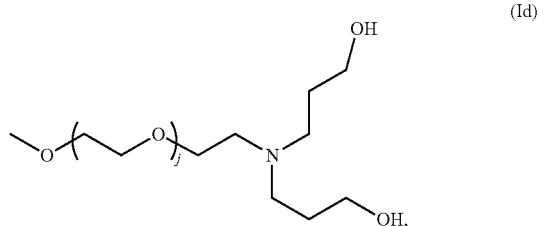

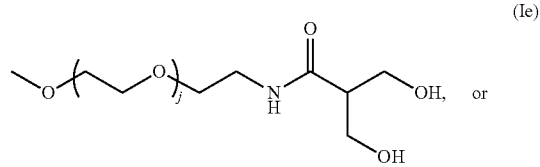

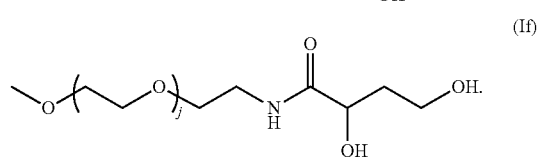

33. The polymer of claim 1, wherein j is an integer from 200 to 500.

34. The polymer of claim 1, wherein the polymer has an average molecular weight of from about 10 kDa to about 30 kDa.

35. The polymer of claim 28, wherein each of $R^{5b}$ and $R^{6b}$ is independently —$NR^{8a}R^{8b}$.

36. The polymer of claim 35, wherein $R^{8a}$ is H and each $R^{8b}$ is independently

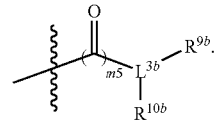

37. The polymer of claim 36, wherein each of $R^{9b}$ and $R^{10b}$ is independently —$NR^{12a}R^{12b}$.

38. The polymer of claim 37, wherein $R^{12a}$ is H and each $R^{12b}$ is independently H or an amino protecting group, or $R^{12a}$ and $R^{12b}$ taken together is a divalent amino protecting group.

* * * * *